United States Patent
Fyfe et al.

(10) Patent No.: US 7,582,632 B2
(45) Date of Patent: Sep. 1, 2009

(54) TRI(CYCLO) SUBSTITUTED AMIDE COMPOUNDS

(75) Inventors: Matthew Colin Thor Fyfe, Oxford (GB); Lisa Sarah Gardner, Oxford (GB); Maseo Nawano, Todu (JP); Martin James Procter, Oxford (GB); Chrystelle Marie Rasamison, Oxford (GB); Karen Lesley Schofield, Oxford (GB); Vilasben Kanji Shah, Oxford (GB); Kosuke Yasuda, Todu (JP)

(73) Assignee: Prosidion Limited, Oxford (GB)

( * ) Notice: Subject to any disclaimer, the term of this patent is extended or adjusted under 35 U.S.C. 154(b) by 0 days.

(21) Appl. No.: 11/735,685

(22) Filed: Apr. 16, 2007

(65) Prior Publication Data

US 2007/0281946 A1 Dec. 6, 2007

Related U.S. Application Data

(62) Division of application No. 10/776,584, filed on Feb. 10, 2004, now Pat. No. 7,214,681.

(60) Provisional application No. 60/446,683, filed on Feb. 11, 2003, provisional application No. 60/494,434, filed on Aug. 11, 2003, provisional application No. 60/512,800, filed on Oct. 20, 2003.

(51) Int. Cl.
*A61K 31/4433* (2006.01)
*A61P 3/00* (2006.01)
*C07D 405/12* (2006.01)
*C07D 413/12* (2006.01)
*C07D 417/12* (2006.01)

(52) U.S. Cl. .................... 514/252.01; 514/255.02; 514/256; 514/336; 514/371; 514/380; 544/238; 544/329; 544/336; 546/282.1; 548/195; 548/246; 548/365.7

(58) Field of Classification Search .................... None
See application file for complete search history.

(56) References Cited

U.S. PATENT DOCUMENTS

| | | | |
|---|---|---|---|
| 4,046,768 A | 9/1977 | Krenzer et al. | |
| 6,320,050 B1 | 11/2001 | Bizzaro et al. | |
| 6,353,111 B1 | 3/2002 | Corbett et al. | |
| 6,369,232 B1 | 4/2002 | Siddori et al. | |
| 6,384,220 B2 | 5/2002 | Corbett et al. | |
| 6,388,071 B2 | 5/2002 | Mahaney et al. | |
| 6,388,088 B1 | 5/2002 | Sidduri et al. | |
| 6,433,188 B1 | 8/2002 | Corbett et al. | |
| 6,441,180 B1 | 8/2002 | Sidduri et al. | |
| 6,441,184 B1 | 8/2002 | Corbett et al. | |
| 6,448,399 B1 | 9/2002 | Corbett et al. | |
| 6,482,951 B2 | 11/2002 | Guertin et al. | |
| 6,486,184 B2 | 11/2002 | Kester et al. | |
| 6,489,485 B2 | 12/2002 | Bizzarro et al. | |
| 6,610,846 B1 | 8/2003 | Bizzaro et al. | |

2003/0219887 A1 11/2003 Corbett et al.

FOREIGN PATENT DOCUMENTS

| | | |
|---|---|---|
| WO | WO 00/58293 | 10/2000 |
| WO | WO 01/12189 | 2/2001 |
| WO | WO 01/44216 | 6/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/08209 | 1/2002 |
| WO | WO 02/14312 | 2/2002 |
| WO | WO 02/46173 | 6/2002 |
| WO | WO 02/48106 | 6/2002 |
| WO | WO 03/000262 | 1/2003 |
| WO | WO 03/000267 | 1/2003 |
| WO | WO 03/015774 | 2/2003 |
| WO | WO 03/047626 | 6/2003 |
| WO | WO 03/055482 | 7/2003 |
| WO | WO 03/080585 | 10/2003 |
| WO | WO 03/095438 | 11/2003 |
| WO | WO 03/097824 | 11/2003 |
| WO | WO 2004/050645 | 6/2004 |

OTHER PUBLICATIONS

Haruo Saikachi and Akira Tanaka: Synthesis of Derivatives. XXVII. Preparation of 2-Phenyl-3-(5-nitro-2-furyl)acrylic Acid, 2-Phenyl-5-(5-nitro-2-furyl)-2,4-pentadienoic Acid, and their Amides (Pharmaceutical Institute, Medical Facility, University of Kyushu). 1-6.
Albert Kascheres, Juan L. Reyes R., and Suzana M. Fonseca, Reaction of Diphenylclopropenone with 2-Aminothiazoles and Related Compounds, Heterocycles, vol. 22, No. 11, 1984, 2529-2534.
Albert Kascheres, and J. Augusto R. Rodrigues, Reaction of Diphenylclopropenone with 2-Aminopyridines. Synthetic and Mechanistic Implications. J. Org. Chem., vol. 40, No. 10, 1975, pp. 1440-1443.
R.L. Printz et al., Ann. Rev. Nutrition, 13:463-496(1993).
Y. Liang et al., Biochem. J., 309:167-173(1995).
H.B.T. Christesen et al., Diabetes, 51:1240-1246 (2002).
Printout of Delphion Abstract for WO 03/97824.
Printout of Delphion Abstract for WO 03/080585.

(Continued)

*Primary Examiner*—Kamal A Saeed
(74) *Attorney, Agent, or Firm*—James B. Myers

(57) ABSTRACT

Compounds of Formula (I):

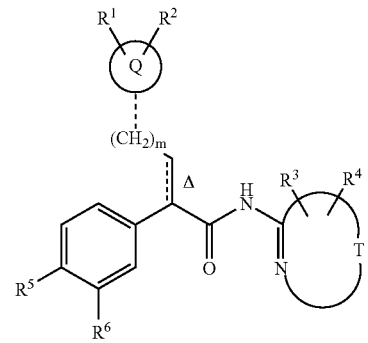

or pharmaceutically acceptable salts thereof, are useful in the prophylactic and therapeutic treatment of hyperglycemia and diabetes.

22 Claims, No Drawings

OTHER PUBLICATIONS

Database Caplus Chemical Abstracts Service, Columbus, Ohio, US; XP002284124 retrieved from STN Database accession No. 1964:4864.

Database Caplus Chemical Abstracts Service, Columbus, Ohio, US; XP002284125 retrieved from STN Database accession No. 1958:25545.

Chemical Abstracts, vol. 55, No. 8, Apr. 17, 1961, Columbus, Ohio, US; Saikachi H et al: "Syntheses of furan derivatives. XXVII. 2-Phenyl-3-(5-nitro-2-furyl)acrylic acid, 2-phenyl-5-(5-nitro-2-furyl)-2,4-pentadienoic acid, an their amides" col. 7380 XP002284123.

Database Chemcats Chemical Abstracts Service, Columbus, Ohio, US; XP002284126 retrieved from STN Database accession No. 2002:273644.

TRI(CYCLO) SUBSTITUTED AMIDE COMPOUNDS

This application is a divisional of U.S. application Ser. No. 10/776,584 filed on Feb. 10, 2004, now U.S. Pat. No. 7,214,681, which in turn claims benefit of U.S. provisional Application Nos. 60/446,683, filed Feb. 11, 2003; 60/494,434, filed on 11 Aug. 2003; and 60/512,800, filed 20 Oct. 2003, each of which is hereby incorporated by reference.

BACKGROUND OF THE INVENTION

The present invention is directed to tri(cyclo) substituted amide compounds. In particular, the present invention is directed to amide compounds substituted i) at the carbonyl carbon with an ethyl/ethenyl attached to a phenyl ring and an aryl/heteroaryl/heterocyclic ring, and ii) at the amino with a nitrogen bearing heteroaryl ring, which are modulators of glucokinase and are useful in the prophylactic or therapeutic treatment of hyperglycemia and type II diabetes.

Glucokinase ("GK") is believed to be important in the body's regulation of its plasma glucose level. GK, found principally in the liver and pancreas, is one of four hexokinases that catalyze the initial metabolism of glucose. The GK pathway is saturated at higher glucose levels than the other hexokinase pathways (See R. L. Printz, et al., *Annu. Rev. Nutr.*, 13:463-496 (1993)). GK is critical to maintaining the glucose balance in mammals. Animals that do not express GK die soon after birth with diabetes, while animals that overexpress GK have improved glucose tolerance. Activation of GK can lead to hyperinsulinemic hypoglycemia. (See, for example, H. B. T. Christesen et al., *Diabetes*, 51:1240-1246 (2002)). Additionally, type II maturity-onset diabetes of the young is caused by the loss of function mutations in the GK gene, suggesting that GK operates as a glucose sensor in humans. (Y. Liang et al., *Biochem. J.* 309:167-173 (1995)). Thus, compounds that activate GK increase the sensitivity of the GK sensory system and would be useful in the treatment of hyperglycemia—particularly the hyperglycemia associated with type II diabetes. It is therefore desirable to provide novel compounds that activate GK to treat diabetes.

International Patent Publication No. WO2001044216 and U.S. Pat. No. 6,353,111 describe (E)-2,3-disubstituted-N-heteroarylacrylamides as GK activators. International Patent Publication No. WO2002014312 and U.S. Pat. Nos. 6,369,232, 6,388,088, and 6,441,180 describe tetrazolylphenylacetamide GK activators. International Patent Publication No. WO2000058293, European Patent Application No. EP 1169312 and U.S. Pat. No. 6,320,050 describe arylcycloalkylpropionamide GK activators. International Patent Publication No. 2002008209 and U.S. Pat. No. 6,486,184 describe alpha-acyl and alpha-heteroatom-substituted benzene acetamide GK activators as anti-diabetic agents. International Patent Publication No. WO2001083478 describes hydantoin-containing GK activators. International Patent Publication No. WO2001083465 and U.S. Pat. No. 6,388,071 describe alkynylphenyl heteroaromatic GK activators. International Patent Publication No. WO2001085707 and U.S. Pat. No. 6,489,485 describe para-amine substituted phenylamide GK activators. International Patent Publication No. WO2002046173 and U.S. Pat. Nos. 6,433,188, 6,441,184, and 6,448,399 describe fused heteroaromatic GK activators. International Patent Publication No. WO2002048106 and U.S. Pat. No. 6,482,951 describe isoindolin-1-one GK activators. International Patent Publication No. WO2001085706 describes substituted phenylacetamide GK activators for treating type II diabetes. U.S. Pat. No. 6,384,220 describes para-aryl or heteroaryl substituted phenyl GK activators. French Patent No. 2,834,295 describes methods for the purification and crystal structure of human GK. International Patent Publication No. WO2003095438, published after the priority date of the present application, describes N-heteroaryl phenylacetamides and related compounds as GK activators for the treatment of type II diabetes. U.S. Pat. No. 6,610,846 describes the preparation of cycloalkylheteroaryl propionamides as GK activators. International Patent Publication No. WO2003000262 describes vinyl phenyl GK activators. International Patent Publication No. WO2003000267 describes aminonicotinate derivatives as GK modulators. International Patent Publication No. WO2003015774, published after the priority date of the present application, describes compounds as GK modulators. International Patent Publication No. WO2003047626, published after the priority date of the present application, describes the use of a GK activator in combination with a glucagon antagonist for treating type II diabetes. International Patent Publication No. WO2003055482, published after the priority date of the present application, describes amide derivatives as GK activators. International Patent Publication No. WO2003080585, published after the priority date of the present application, describes aminobenzamide derivatives with GK activity for the treatment of diabetes and obesity. International Patent Publication No. WO2003097824, published after the priority date of the present application, describes human liver GK crystals and their used for structure-based drug design. International Patent Publication No. WO2004002481, published after the priority date of the present application, discloses arylcarbonyl derivatives as GK activators.

SUMMARY OF THE INVENTION

Compounds represented by Formula (I):

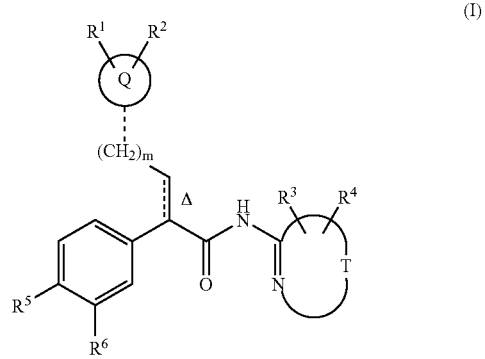

or pharmaceutically acceptable salts thereof, are useful in the prophylactic or therapeutic treatment of hyperglycemia and type II diabetes.

DETAILED DESCRIPTION OF THE INVENTION

The present invention is directed to a compound of Formula (I):

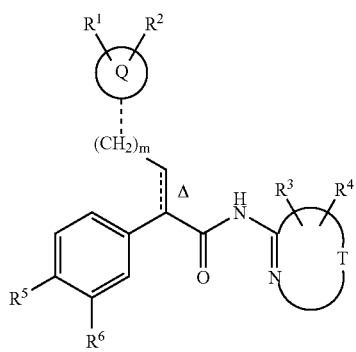

or a pharmaceutically acceptable salt thereof, wherein:

Q is an aryl, a 5- or 6-membered heteroaryl, or a 4-8-membered heterocyclic ring;

T together with the —N=C— to which it is attached forms a heteroaryl ring, or a heterocyclic ring where the N=C bond is the only site of unsaturation;

$R^1$ and $R^2$ each independently are hydrogen, hydroxy, halogen, cyano, nitro, vinyl, ethynyl, methoxy, $OCF_nH_{3-n}$, —N($C_{0-4}$alkyl)($C_{0-4}$alkyl), CHO, or $C_{1-2}$alkyl optionally substituted with 1-5 independent halogen, hydroxy, cyano, methoxy, —N($C_{0-2}$alkyl)($C_{0-2}$alkyl), $SOCH_3$, or $SO_2CH_3$ substituents; or $R^1$ and $R^2$ together form a carbocyclic or heterocyclic ring; or $R^1$ and $R^2$ may be taken together to represent an oxygen atom attached to the ring via a double bond;

$R^3$ and $R^4$ each independently are hydrogen, halogen, $OCF_nH_{3-n}$, methoxy, $CO_2R^{77}$, cyano, nitro, CHO, $CONR^{99}R^{100}$, $CON(OCH_3)CH_3$, or $C_{1-2}$alkyl, heteroaryl, or $C_{3-7}$cycloalkyl optionally substituted with 1-5 independent halogen, hydroxy, cyano, methoxy, —$NHCO_2CH_3$, or —N($C_{0-2}$alkyl)($C_{0-2}$alkyl) substituents; or $R^3$ and $R^4$ together form a 5-8-membered aromatic, heteroaromatic, carbocyclic, or heterocyclic ring;

$R^5$ and $R^6$ each independently are hydrogen, hydroxy, halogen, cyano, nitro, $CO_2R^7$, CHO, $COR^8$, $C(OH)R^7R^8$, $C(=NOR^7)R^8$, $CONR^9R^{10}$, $SR^7$, $SOR^8$, $SO_2R^8$, $SO_2NR^9R^{10}$, $CH_2NR^9R^{10}$, $NR^9R^{10}$, $N(C_{0-4}alkyl)SO_2R^8$, $NHCOR^7$, or $C_{1-4}$alkyl group, $C_{2-4}$alkenyl group, $C_{2-4}$alkynyl group, $C_{1-4}$alkoxy group, aryl group, or heteroaryl group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $CF_nH_{3-n}$, aryl, heteroaryl, —$COC_{1-2}$alkyl, —$CON(C_{0-2}$alkyl)($C_{0-2}$alkyl), $SCH_3$, $SOCH_3$, $SO_2CH_3$, or —$SO_2N(C_{0-2}$alkyl)($C_{0-2}$alkyl) substituents; or $R^5$ and $R^6$ together form a 5-8-membered carbocyclic or heterocyclic ring;

$R^7$ and $R^{77}$ each independently are hydrogen, or $C_{1-4}$alkyl group, $C_{2-4}$alkenyl group, $C_{2-4}$alkynyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $C_{3-7}$cycloalkyl, 4-7-membered heterocyclic ring, $CF_nH_{3-n}$, aryl, heteroaryl, $CO_2H$, —$COC_{1-2}$alkyl, —$CON(C_{0-2}$alkyl)($C_{0-2}$alkyl), $SOCH_3$, $SO_2CH_3$, or —$SO_2N(C_{0-2}$alkyl)($C_{0-2}$alkyl) substituents;

$R^8$ is $C_{1-4}$alkyl group, $C_{2-4}$alkenyl group, $C_{2-4}$alkynyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $C_{3-7}$cycloalkyl, 4-7-membered heterocyclic ring, $CF_nH_{3-n}$, aryl, heteroaryl, $CO_2H$, $COC_{1-2}$alkyl, —$CON(C_{0-2}$alkyl)($C_{0-2}$alkyl), $SOCH_3$, $SO_2CH_3$, or —$SO_2N(C_{0-2}$alkyl)($C_{0-2}$alkyl) substituents;

$R^9$, $R^{10}$, $R^{99}$, $R^{100}$ each independently are hydrogen, or $C_{1-4}$alkyl group, $C_{3-7}$cycloalkyl group, aryl group, heteroaryl group, or 4-7-heterocyclic group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $C_{3-7}$cycloalkyl, 4-7-membered heterocyclic ring, $CF_nH_{3-n}$, aryl, heteroaryl, $COC_{1-2}$alkyl, —$CON(C_{0-2}$alkyl)($C_{0-2}$alkyl), $SOCH_3$, $SO_2CH_3$, or —$SO_2N(C_{0-2}$alkyl)($C_{0-2}$alkyl) substituents; or $R^9$ and $R^{10}$ or $R^{99}$ and $R^{100}$ together form a 6-8-membered heterobicyclic ring system or a 4-8-membered heterocyclic ring which optionally is substituted with 1-2 independent $C_{1-2}$alkyl, $CH_2OCH_3$, $COC_{0-2}$alkyl, hydroxy, or $SO_2CH_3$ substituents;

n is 1, 2 or 3;

m is 0 or 1; and the dotted line together with the solid line forms an optional double bond, and Δ indicates that the double bond has the (E)-configuration.

If the dotted line together with the solid line forms a single bond, the carbon atom linking the aryl ring and Q-bearing sidechain to the carbonyl carbon is a chiral centre. Accordingly, the compound may be present either as a racemate, or as a single enantiomer in the (R)- or (S)-configuration. The (R)-enantiomers are preferred.

A particular group of compounds which may be mentioned are compounds of Formula (I), or pharmaceutically acceptable salts thereof, provided that when Q is an unsubstituted 5- or 6-membered heterocyclic ring containing one heteroatom selected from O, S and S=O;

T completes a 5- or 6-membered heteroaryl ring which is unsubstituted or monosubstituted by halogen, methoxy, $CO_2$—$C_{0-4}$alkyl, cyano, nitro, $CONH_2$, CONH—$C_{1-4}$alkyl, perfluoro$C_{1-2}$alkyl, or $C_{1-2}$alkyl optionally monosubstituted with methoxy or —NH($C_{0-2}$alkyl);

$R^5$ and $R^6$ each independently are hydrogen, hydroxy, halogen, cyano, nitro, $CO_2$—$C_{1-4}$alkyl, S—$C_{1-4}$alkyl, S-perfluoro$C_{1-4}$alkyl, SO—$C_{1-4}$alkyl, $SO_2$—$C_{1-4}$alkyl, $SO_2$-perfluoro$C_{1-4}$alkyl, $SO_2NH_2$, $NH_2$, $C_{1-4}$alkyl, perfluoro$C_{1-4}$alkyl, $C_{1-4}$alkoxy or perfluoro$C_{1-4}$alkoxy; and m is 0;

then the dotted line together with the solid line must form a double bond.

In the first aspect, the present invention is directed to a compound represented by Formula (Ia):

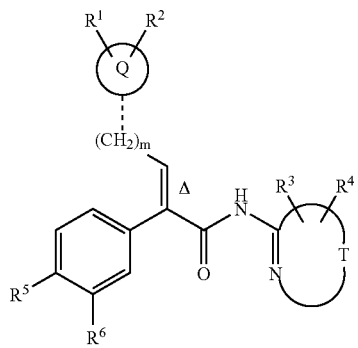

(Ia)

or a pharmaceutically acceptable salt thereof, wherein Q, T, $R^1$-$R^6$, m, and $\Delta$ are as defined above in Formula (I).

In an embodiment of the first aspect, the present invention is directed to a compound represented by Formula (Ia), or a pharmaceutically acceptable salt thereof, wherein: Q is an aryl.

In another embodiment of the first aspect, the present invention is directed to a compound represented by Formula (Ia), or a pharmaceutically acceptable salt thereof, wherein Q is a 5- or 6-membered heteroaryl ring.

In another embodiment of the first aspect, the present invention is directed to a compound represented by Formula (Ia), or a pharmaceutically acceptable salt thereof, wherein Q is a thienyl, furyl, thiazolyl, or pyridyl ring.

In another embodiment of the first aspect, the present invention is directed to a compound represented by Formula (Ia), or a pharmaceutically acceptable salt thereof, wherein Q is a 4-8-membered heterocyclic ring.

In another embodiment of the first aspect, the present invention is directed to a compound represented by Formula (Ia), or a pharmaceutically acceptable salt thereof, wherein Q is tetrahydropyranyl, piperidinyl, tetrahydrothiopyranyl, 1-oxo-tetrahydrothiopyranyl or 1,1-dioxo-tetrahydrothiopyranyl.

In the second aspect, the present invention is directed to a compound represented by Formula (Ib):

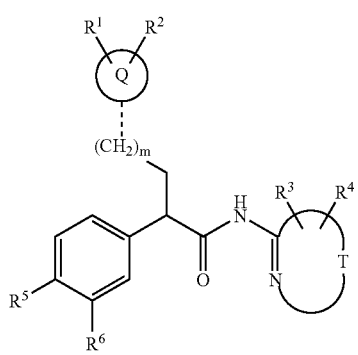

(Ib)

or a pharmaceutically acceptable salt thereof, wherein Q, T, $R^1$-$R^6$ and m are as defined above in Formula (I).

In an embodiment of the second aspect, the present invention is directed to a compound represented by Formula (Ib), or a pharmaceutically acceptable salt thereof, wherein: Q is a 5- or 6-membered heteroaryl ring.

In another embodiment of the second aspect, the present invention is directed to a compound represented by Formula (Ib), or a pharmaceutically acceptable salt thereof, wherein: Q is a thienyl, furyl, thiazolyl, or pyridyl ring.

In another embodiment of the second aspect, the present invention is directed to a compound represented by Formula (Ib), or a pharmaceutically acceptable salt thereof, wherein: Q is a 4-8-membered heterocyclic ring.

In another embodiment of the second aspect, the present invention is directed to a compound represented by Formula (Ib), or a pharmaceutically acceptable salt thereof, wherein: Q is tetrahydropyranyl, piperidinyl, tetrahydrothiopyranyl, 1-oxo-tetrahydrothiopyranyl, or 1,1-dioxo-tetrahydrothiopyranyl.

The molecular weight of the compounds of formula (I) is preferably less than 800, more preferably less than 600, most preferably less than 500.

In the present invention, Q is preferably 2-furyl, 2-thienyl, tetrahydropyranyl, tetrahydrothiopyranyl, 1-oxo-tetrahydrothiopyranyl, or 1,1-dioxo-tetrahydrothiopyranyl; more preferably 4-tetrahydropyranyl or 4-tetrahydrothiopyranyl; most preferably 4-tetrahydropyranyl.

When Q is a heteroaryl or heterocyclic group it is preferably linked to the —$(CH_2)_m$— group through a carbon atom.

When Q is a heteroaryl group it preferably does not have a substituent $R^1$ or $R^2$ other than hydrogen at a position adjacent to point of attachment to the —$(CH_2)_m$— group.

In the present invention, the group of formula

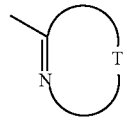

is preferably a monocyclic heteroaryl group. More preferably it is thiazolyl, thiadiazolyl, oxazolyl, isoxazolyl, pyrimidinyl, pyrazinyl, or pyridyl; more preferably 2-thiazolyl, 5-[1,2,4]thiadiazolyl, 2-[1,3,4]thiadiazolyl, 4-pyrimidinyl, 2-pyrazinyl, 3-isoxazolyl, or 2-pyridyl; even more preferably 2-thiazolyl, 5-[1,2,4]thiadiazolyl, 4-pyrimidinyl, 2-pyrazinyl, or 2-pyridyl; most preferably 2-thiazolyl, 2-pyrazinyl, or 2-pyridyl.

More preferably the group of formula

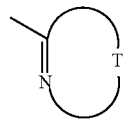

is 2-thiazolyl, or 2-pyrazinyl.

Most preferably the group of formula

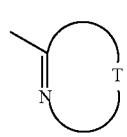

is 2-thiazolyl and $R^3$ is 5-fluoro and $R^4$ is hydrogen; or 2-pyrazinyl and $R^3$ and $R^4$ are hydrogen; especially preferred is 2-thiazolyl where $R^3$ is 5-fluoro and $R^4$ is hydrogen.

In the present invention, $R^1$ and $R^2$ are preferably hydrogen.

In the present invention $R^3$ and $R^4$ are preferably independently selected from hydrogen, halogen, and methyl, more preferably $R^3$ and $R^4$ are independently selected from hydrogen, fluoro, and methyl.

In the present invention, $R^3$ is preferably hydrogen or halogen; more preferably hydrogen, fluoro, chloro or bromo; even more preferably hydrogen, fluoro, or chloro; most preferably hydrogen or fluoro.

In the present invention, $R^4$ is preferably hydrogen, halogen, or methyl; more preferably hydrogen or methyl.

In the present invention, $R^5$ and $R^6$ are preferably not both hydrogen.

In the present invention, $R^5$ is preferably $CF_3$, $SOR^8$, $SO_2R^8$, $SO_2NR^9R^{10}$, $NHSO_2R^8$, or triazolyl; more preferably $SOR^8$, $SO_2R^8$, or $SO_2NR^9R^{10}$; most preferably $SO_2R^8$ or $SO_2NR^9R^{10}$, especially $SO_2R^8$.

In particular $R^5$ is $SO_2C_{3-4}$cycloalkyl, especially $SO_2$cyclopropyl.

In the present invention, $R^6$ is preferably hydrogen, chloro, fluoro, or trifluoromethyl; more preferably hydrogen.

In the present invention, $R^7$, $R^{77}$, and $R^8$ are preferably $C_{1-4}$alkyl, $C_{3-7}$cycloalkyl, heteroaryl, or 4-7-membered heterocyclic group; more preferably $C_{1-3}$alkyl, 4-6-membered heterocyclic group, or $C_{3-5}$cycloalkyl; most preferably methyl, ethyl, n-propyl, cyclopropyl, cyclobutyl, oxetanyl, or tetrahydrofuryl, and especially methyl, ethyl, n-propyl, cyclopropyl, or cyclobutyl.

When the dotted line together with the solid line forms a double bond $R^8$ is preferably $C_{1-3}$alkyl, or $C_{3-4}$cycloalkyl.

When the dotted line together with the solid line forms a single bond $R^8$ is preferably $C_{3-4}$cycloalkyl, especially cyclopropyl.

When $R^5$ and/or $R^6$ are $CO_2R^7$ or $SR^7$, $R^7$ is preferably not hydrogen.

In the present invention, $R^9$ and $R^{10}$ are preferably independently $C_{0-4}$alkyl e.g. one of $R^9$ and $R^{10}$ is hydrogen and the other is ethyl, or combine to form a 4-8-membered heterocyclic ring. $R^9$ and $R^{10}$ are preferably not both hydrogen.

In the present invention, $R^{99}$ and $R^{100}$ are preferably $C_{0-4}$alkyl.

In the present invention, m is preferably 0.

In the present invention, n is preferably 2 or 3.

A preferred group of compounds are compounds of Formula (I), or pharmaceutically acceptable salts thereof, wherein:

Q is 4-tetrahydropyranyl;

T together with the —N=C— to which it is attached forms a 2-pyrazinyl or 2-thiazolyl ring;

$R^1$ and $R^2$ are hydrogen;

$R^3$ and $R^4$ each independently are hydrogen or fluoro;

$R^5$ is $SO_2R^8$, or $SO_2NR^9R^{10}$;

$R^6$ is hydrogen;

$R^8$ is a $C_{3-5}$cycloalkyl group or a 4-6-membered heterocyclic group, and, in addition, when the dotted line together with the solid line forms a double bond $R^8$ may be a $C_{1-3}$alkyl group;

$R^9$ and $R^{10}$ are independently $C_{0-4}$alkyl, provided that $R^9$ and $R^{10}$ are not both hydrogen;

m is 0; and the dotted line together with the solid line forms an optional double bond, and Δ indicates that the double bond has the (E)-configuration.

A more preferred group of compounds are compounds of Formula (I), or pharmaceutically acceptable salts thereof, wherein:

Q is 4-tetrahydropyranyl;

T together with the —N=C— to which it is attached forms a 2-pyrazinyl or 2-thiazolyl ring;

$R^1$ and $R^2$ are hydrogen;

$R^3$ and $R^4$ each independently are hydrogen or fluoro;

$R^5$ is $SO_2R^8$;

$R^6$ is hydrogen;

$R^8$ is a $C_{3-5}$cycloalkyl group and, in addition, when the dotted line together with the solid line forms a double bond $R^8$ may be a $C_{1-3}$alkyl group;

m is 0; and the dotted line together with the solid line forms an optional double bond, and Δ indicates that the double bond has the (E)-configuration.

Specific compounds of the invention which may be mentioned are those described in the Examples, in particular Examples 1 to 201, and pharmaceutically acceptable salts thereof.

Specific compounds of the invention which may be mentioned are:

(2R)-2-(4-Cyclopropanesulfonylphenyl)-N-(5-fluorothiazol-2-yl)-3-(tetrahydropyran-4-yl)propionamide;

(2R)-2-(4-Cyclopropanesulfonylphenyl)-N-pyrazin-2-yl-3-(tetrahydropyran-4-yl)propionamide;

(2R)-2-(4-Cyclobutanesulfonylphenyl)-N-pyrazin-2-yl-3-(tetrahydropyran-4-yl)propionamide;

(2R)-2-(4-Cyclobutanesulfonylphenyl)-N-(5-fluorothiazol-2-yl)-3-(tetrahydropyran-4-yl)propionamide; and (E)-N-(5-Fluorothiazol-2-yl)-2-(4-methanesulfonylphenyl)-3-(tetrahydropyran-4-yl)acrylamide;

or a pharmaceutically acceptable salt thereof.

In particular the compounds:

(2R)-2-(4-Cyclopropanesulfonylphenyl)-N-(5-fluorothiazol-2-yl)-3-(tetrahydropyran-4-yl)propionamide;

(2R)-2-(4-Cyclopropanesulfonylphenyl)-N-pyrazin-2-yl-3-(tetrahydropyran-4-yl)propionamide; and (E)-N-(5-Fluorothiazol-2-yl)-2-(4-methanesulfonylphenyl)-3-(tetrahydropyran-4-yl)acrylamide;

or a pharmaceutically acceptable salt thereof.

While the preferred groups for each variable have generally been listed above separately for each variable, preferred compounds of this invention include those in which several or each variable in Formula (I) is selected from the preferred, more preferred, most preferred, especially or particularly listed groups for each variable. Therefore, this invention is intended to include all combinations of preferred, more preferred, most preferred, especially and particularly listed groups.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl" and "carbocyclic ring" mean carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "aryl" includes, for example, phenyl and naphthyl.

Unless otherwise stated, the term "heterocyclic ring" includes 4-8-membered saturated rings containing one or two heteroatoms chosen from oxygen, sulfur, and nitrogen. The heteroatoms are not directly attached to one another. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,3]dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

Unless otherwise stated, the term "heteroaryl" includes 5- or 6-membered heteroaryl rings containing 1-4 heteroatoms chosen from oxygen, sulfur, and nitrogen. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, and triazinyl.

The above formulas are shown without a definitive stereochemistry at certain positions. The present invention includes all stereoisomers (e.g. geometric isomers, optical isomers, diastereoisomers, etc.) and pharmaceutically acceptable salts thereof, except where specifically drawn or stated otherwise. Further, mixtures of stereoisomers as well as isolated specific stereoisomers are also included, except where specifically drawn or stated otherwise. During the course of the synthetic procedures used to prepare such compounds, or in using racemization or epimerization procedures known to those skilled in the art, the products of such procedures can be a mixture of stereoisomers. When a tautomer of the compound of the above formulas exists, the present invention includes any possible tautomers and pharmaceutically acceptable salts thereof, and mixtures thereof, except where specifically drawn or stated otherwise. When the compound of the above formulas and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

Since the compounds of Formula (I) are intended for pharmaceutical use they are preferably provided in substantially pure form, for example at least 60% pure, more suitably at least 75% pure, especially at least 98% pure (% are on a weight for weight basis).

The invention also encompasses a pharmaceutical composition that is comprised of a compound of Formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of Formula (I) as described above, or a pharmaceutically acceptable salt thereof.

Moreover, within this preferred embodiment, the invention encompasses a pharmaceutical composition for the prophylaxis or treatment of hyperglycemia and diabetes by the activation of GK, comprising a pharmaceutically acceptable carrier and a non-toxic therapeutically effective amount of compound of Formula (I) as described above, or a pharmaceutically acceptable salt thereof.

The invention also provides the use of a compound of Formula (I), or a pharmaceutically acceptable salt thereof as a pharmaceutical.

The compounds and compositions of the present invention are effective for treating hyperglycemia in mammals such as, for example, humans.

The invention also provides a method of prophylactic or therapeutic treatment of a condition where activation of GK is desirable comprising a step of administering an effective amount of a compound of Formula (I), or a pharmaceutically acceptable salt thereof.

The invention also provides a method of prophylactic or therapeutic treatment of hyperglycemia or diabetes comprising a step of administering an effective amount of a compound of Formula (I), or a pharmaceutically acceptable salt thereof.

The invention also provides a method of prevention of diabetes in a human demonstrating pre-diabetic hyperglycemia or impaired glucose tolerance comprising a step of administering an effective prophylactic amount of a compound of Formula (I), or a pharmaceutically acceptable salt thereof.

The invention also provides the use of a compound of Formula (I), or a pharmaceutically acceptable salt thereof, as a GK activator.

The invention also provides the use of a compound of Formula (I), or a pharmaceutically acceptable salt thereof, for the prophylactic or therapeutic treatment of hyperglycemia or diabetes.

The invention also provides the use of a compound of Formula (I), or a pharmaceutically acceptable salt thereof, for the prevention of diabetes in a human demonstrating pre-diabetic hyperglycemia or impaired glucose tolerance.

The invention also provides the use of a compound of Formula (I), or a pharmaceutically acceptable salt thereof, in the manufacture of a medicament for the activation of GK.

The invention also provides the use of a compound of Formula (I), or a pharmaceutically acceptable salt thereof, in the manufacture of a medicament for the prophylactic or therapeutic treatment of hyperglycemia or diabetes.

The invention also provides the use of a compound of Formula (I), or a pharmaceutically acceptable salt thereof, in the manufacture of a medicament for the prevention of diabetes in a human demonstrating pre-diabetic hyperglycemia or impaired glucose tolerance.

The compounds and compositions of the present invention may be optionally employed in combination with one or more other anti-diabetic agents or anti-hyperglycemic agents, which include, for example, sulfonylureas (e.g. glyburide, glimepiride, glipyride, glipizide, chlorpropamide, gliclazide, glisoxepid, acetohexamide, glibornuride, tolbutamide, tolazamide, carbutamide, gliquidone, glyhexamide, phenbutamide, tolcyclamide, etc.), biguanides (e.g. metformin, pheniformin, buformin, etc.), glucagon antagonists (e.g. a peptide or non-peptide glucagon antagonist), glucosidase inhibitors (e.g. acarbose, miglitol, etc.), insulin secetagogues, insulin sensitizers (e.g. troglitazone, rosiglitazone, pioglitazone, etc.) and the like; or anti-obesity agents (e.g. sibutramine, orlistat, etc.) and the like. The compounds and compositions of the present invention and the other anti-diabetic agents or anti-hyperglycemic agents may be administered simultaneously, sequentially or separately.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthetic amines. Other pharmaceutically acceptable organic non-toxic bases from which salts can be formed include, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, methanesulfonic, and tartaric acids.

The pharmaceutical compositions of the present invention comprise a compound of Formula (I), or a pharmaceutically acceptable salt thereof, as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, as well as administration through inhaling, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The pharmaceutical compositions according to the invention are preferably adapted for oral administration.

In practice, the compounds of Formula (I), or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound of Formula (I), or a pharmaceutically acceptable salt thereof. The compounds of Formula (I), or pharmaceutically acceptable salts thereof, can also be included in pharmaceutical compositions in combination with one or more other therapeutically active compounds.

The pharmaceutical compositions of this invention include a pharmaceutically acceptable liposomal formulation containing a compound of Formula (I) or a pharmaceutically acceptable salt thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound of Formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

Pharmaceutical compositions of this invention can be in a form suitable for inhaled administration. Such administration can be in forms and utilizing carriers described in, for example, 1) *Particulate Interaction in Dry Powder Formula-*

*tions for Inhalation*, Xian Zeng et al, 2000, Taylor and Francis, 2) *Pharmaceutical Inhalation Aerosol Technology*, Anthony Hickey, 1992, Marcel Dekker, 3) *Respiratory Drug Delivery*, 1990, Editor: P. R. Byron, CRC Press.

In addition to the aforementioned carrier ingredients, the pharmaceutical compositions described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of Formula (I), or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 10 g per patient per day. For example, diabetes may be effectively treated by the administration of from about 0.01 to 100 mg of the compound per kilogram of body weight per day, or alternatively about 0.5 mg to about 7 g per patient per day.

It is understood, however, that the specific dose level for any particular patient will depend upon a variety of factors including the age, body weight, general health, sex, diet, time of administration, route of administration, rate of excretion, drug combination and the severity of the disease in the particular diabetic patient undergoing therapy. Further, it is understood that the compounds and salts thereof of this invention can be administered at subtherapeutic levels prophylactically in anticipation of a hyperglycemic condition.

The compounds of Formula (I) may exhibit advantageous properties compared to known glucokinase activators, e.g. as illustrated in the assays described herein. In particular compounds of the invention may exhibit improved values for $K_m$, $V_{max}$, $EC_{50}$, maximum activation (glucose concentration=5 mM), and/or maximum blood glucose reduction on basal blood glucose levels (e.g. in C57BL/6J mice), or other advantageous pharmacological properties, compared to known GK activators

EXPERIMENTAL

In accordance with this invention, the compounds of Formula (Ia) can be prepared following the protocol illustrated in Scheme 1 below:

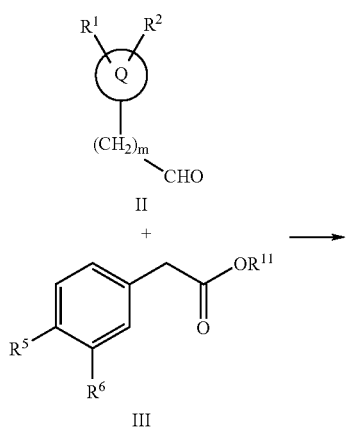

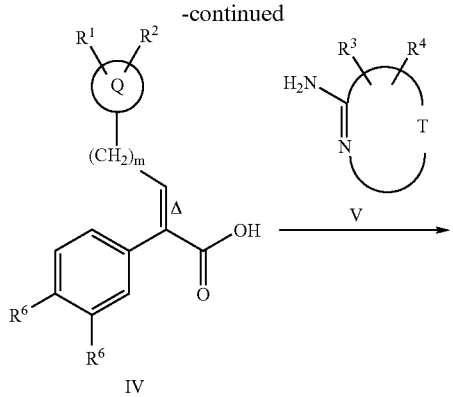

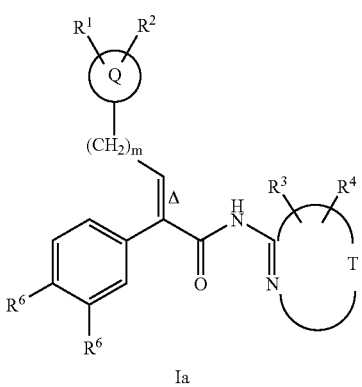

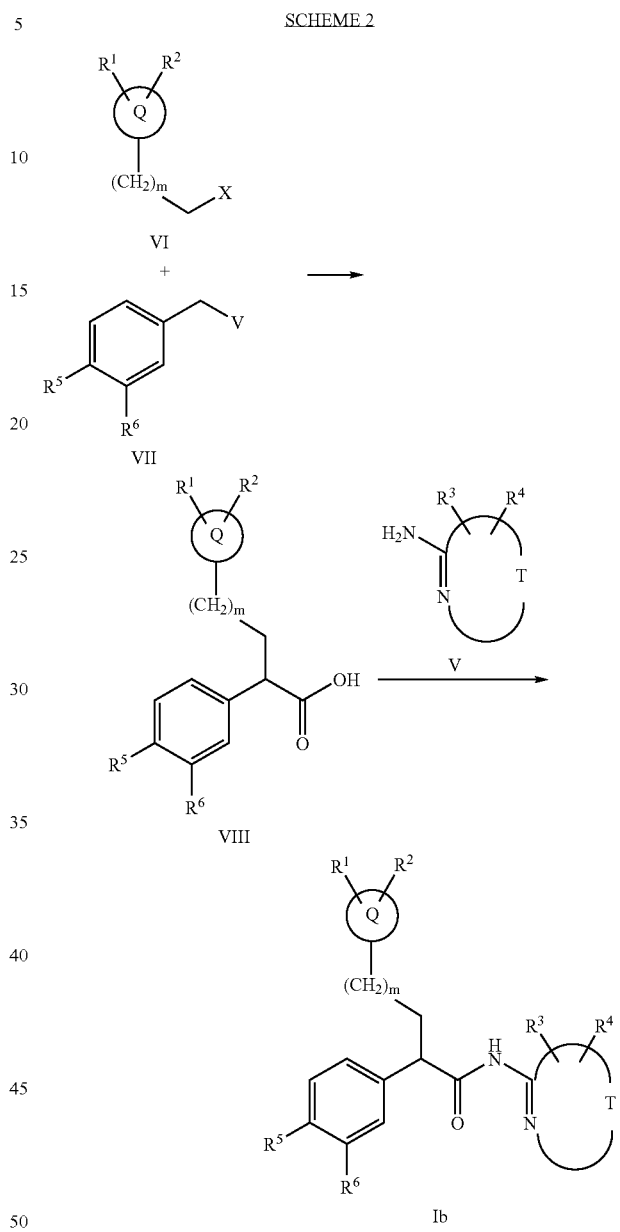

The compounds of Formula (Ib) can be made by the route displayed in Scheme 2 below:

wherein Q, T, $R^1$-$R^6$, m and Δ are as described above, and $R^{11}$ is $C_{0-4}$alkyl.

The aldehydes II and phenylacetic acids or esters III are commercially available or are readily prepared using known techniques. When Q represents an aromatic or heteroaromatic ring, IV may be prepared by the Perkin reaction (G. Karminski-Zamola et al., *Tetrahedron* 1982, 38, 1329-1335). In this reaction, II is condensed with the phenylacetic acid III ($R^{11}$=$C_0$alkyl) in the presence of a carboxylic acid anhydride, e.g. acetic anhydride, and a tertiary amine base, e.g. triethylamine, at reflux to give the acrylic acid IV. Alternatively, IV may be prepared through the condensation of II and III ($R^{11}$=$C_0$alkyl) under the influence of an amine base, such as piperidine, in toluene under reflux (D. Deschenes et al., WO 01/46151). When Q is a heterocyclic ring, the α-carbanion of the phenylacetic ester III ($R^{11}$=$C_{1-4}$alkyl), generated at −78° C. in, for example, tetrahydrofuran, by a strong base, e.g. lithium diisopropylamide, may be condensed with II to give an α,β-unsaturated ester (T. Severin et al. *Chem. Ber.* 1985, 118, 4760-4773) that may be saponified using, for example, sodium hydroxide (W. L. Corbett et al., WO 01/44216), to produce IV.

The α,β-unsaturated carboxylic acids IV may be condensed with heteroaromatic amines V, many of which are commercially available, using a variety of coupling conditions, e.g. polymer supported carbodiimide-1-hydroxybenzotriazole in N,N-dimethylformamide at 20° C. (for representative procedures, see http://www.argotech.com/PDF/resins/ps_carbodiimide.pdf and available from Argonaut Technologies, Inc., Foster City, Calif.), to give (Ia).

wherein Q, T, $R^1$-$R^6$ and m are as described above, V is $CO_2R^{11}$ or $CO_2CH_2Ph$, and X is chloro, bromo, iodo, or —$OSO_2R^{12}$; wherein $R^{11}$ is as described above and $R^{12}$ is $C_{1-4}$alkyl, optionally substituted with one or more fluorines, or optionally substituted aryl.

The halides and sulfonate esters VI are commercially available or are readily prepared using known techniques. These alkylating agents may be reacted with the dianions of the phenylacetic acids VII, generated at −78° C. in tetrahydrofuran with ≧2 equivalents of a strong base, such as lithium diisopropylamide, to generate VIII directly (F. T. Bizzarro et al., WO 00/58293). Alternatively, the α-carbanion of phenylacetic ester VII, generated at −78° C. in tetrahydrofuran by a strong base, such as lithium bis(trimethylsilyl)amide (L. Snyder et al., *J. Org. Chem.* 1994, 59, 7033-7037), can be alkylated by VI to give α-substituted esters. Saponification of these esters, employing, for example, sodium hydroxide in aqueous methanol at 20° C. to reflux, leads to the carboxylic acids VIII.

The carboxylic acids VIII may be condensed with heteroaromatic amines V using a variety of coupling conditions, e.g. polymer supported carbodiimide-1-hydroxybenzotriazole in N,N-dimethylformamide at 20° C. (for representative procedures, see http://www.argotech.com/PDF/resins/ps_carbodiimide.pdf and available from Argonaut Technologies, Inc., Foster City, Calif.), to give amides (Ib).

The compound of Formula (Ib) has an asymmetric carbon atom which interlinks the amide carbonyl carbon, the aryl ring, and the Q-containing sidechain. In accordance with this invention, the preferred stereoconfiguration at the asymmetric centre is (R).

If one desires to isolate the pure (R)- or (S)-stereoisomers of the compound of Formula (Ib), it is possible to resolve a racemic mixture of the chiral carboxylic acid precursor VIII by any conventional chemical means and then condense the enantiopure carboxylic acids with an amine of formula V using a reagent that causes negligible racemisation. By way of illustration, racemic VIII can be condensed with a chiral oxazolidinone derivative (see, for instance, F. T. Bizzarro et al. WO 00/58293) to generate a mixture of diastereoisomeric imides that are separable by any conventional method, e.g. column chromatography. Hydrolysis of the pure imides affords the stereopure (R)- and (S)-carboxylic acids that can then be condensed with heterocyclic amines V, employing a reagent that minimises racemisation of the chiral centre, e.g. benzotriazol-1-yloxytris(pyrrolidino)phosphonium hexafluorophosphate (J. Coste et al. *Tetrahedron Lett.* 1990, 31, 205-208), to furnish enantiopure (R)- or (S)-amides of Formula (Ib). Alternatively, a racemic mixture of amides of Formula (Ib) can be separated by means of chiral high performance liquid chromatography employing a chiral stationary phase which can be purchased from, for example, Daicel Chemical Industries, Ltd, Tokyo, Japan.

Further details for the preparation of the compounds of Formula (I) are found in the examples.

The compounds of Formula (I) may be prepared singly or as compound libraries comprising at least 2, for example 5 to 1,000, compounds and more preferably 10 to 100 compounds of Formula (I). Compound libraries may be prepared by a combinatorial "split and mix" approach or by multiple parallel synthesis using either solution or solid phase chemistry, using procedures known to those skilled in the art.

During the synthesis of the compounds of Formula (I), labile functional groups in the intermediate compounds, e.g. hydroxy, carboxy and amino groups, may be protected. The protecting groups may be removed at any stage in the synthesis of the compounds of Formula (I) or may be present on the final compound of Formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York, 2nd edition.

Any novel intermediates as defined above are also included within the scope of the invention.

According to a further aspect of the invention there is provided a compound of Formula (IV) and the use of such compounds in the synthesis of GK activators:

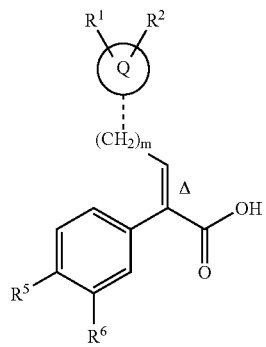

wherein Q, $R^1$, $R^2$, $R^5$, $R^6$, m and Δ are as described for Formula (I).

Preferred compounds of formula (IV) are those wherein:
Q is 4-tetrahydropyranyl;
$R^1$ and $R^2$ are hydrogen;
$R^5$ is $SO_2R^8$, or $SO_2NR^9R^{10}$;
$R^6$ is hydrogen;
$R^8$ is a $C_{1-3}$alkyl group, a $C_{3-5}$cycloalkyl group or a 4-6-membered heterocyclic group;
$R^9$ and $R^{10}$ are independently $C_{0-4}$alkyl, provided that $R^9$ and $R^{10}$ are not both hydrogen;
m is 0; and
Δ indicates that the double bond has the (E)-configuration.

According to a further aspect of the invention there is provided a compound of Formula (VIII) and the use of such compounds in the synthesis of GK activators:

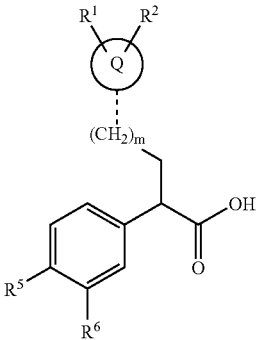

wherein Q, $R^1$, $R^2$, $R^5$, $R^6$ and m are as described for Formula (I).

Preferred compounds of formula (VIII) are those wherein:
Q is 4-tetrahydropyranyl;
$R^1$ and $R^2$ are hydrogen;
$R^5$ is $SO_2R^8$, or $SO_2NR^9R^{10}$;
$R^6$ is hydrogen;
$R^8$ is a $C_{3-5}$cycloalkyl group or a 4-6-membered heterocyclic group;
$R^9$ and $R^{10}$ are independently $C_{0-4}$alkyl, provided that $R^9$ and $R^{10}$ are not both hydrogen; and
m is 0.

The preferences for the various substituent groups in the compounds of Formulae (IV) and (VIII) are as described above for the compounds of Formula (I).

Specific compounds of Formulae (IV) and (VIII) include those described in the Preparations.

According to a further aspect of the invention there is also provided 5-fluorothiazol-2-ylamine or an amide or acid addition salt thereof. In particular the invention provides the amides and acid addition salts of this compound. Suitable acid addition salts include those formed with inorganic and organic acids. Such acids include, for example, acetic, trifluoroacetic, benzenesulfonic, benzoic, camphorsulfonic, citric, ethanesulfonic, fumaric, gluconic, glutamic, hydrobromic, hydrochloric, hydrofluoric isethionic, lactic, maleic, mandelic, methanesulfonic, mucic, nitric, pamoic, pantothenic, phosphoric, succinic, sulfuric, tartaric, p-toluenesulfonic acid, triflic and the like. Particularly preferred are the hydrohalide salts especially the hydrochloride. The amides and acid addition salts of 5-fluorothiazol-2-ylamine may be useful as intermediates for the synthesis of compounds of Formula (I) or may themselves act as GK activators and hence be of use in the prophylactic or therapeutic treatment of hyperglycemia and type II diabetes.

All publications, including, but not limited to, patents and patent application cited in this specification, are herein incorporated by reference as if each individual publication were specifically and individually indicated to be incorporated by reference herein as fully set forth.

Materials and Methods

Microwave reactions were performed in a CEM Explorer system at 100 W. Column chromatography was carried out on $SiO_2$ (40-63 mesh) unless specified otherwise. LCMS data were obtained employing one of two methods: Method A: Waters Symmetry 3.5μ $C_{18}$ column (2.1×30.0 mm, flow rate=0.8 mL/min) eluting with a (5% MeCN in $H_2O$)-MeCN solution containing 0.1% $HCO_2H$ over 6 min and UV detection at 220 nm. Gradient information: 0.0-1.2 min: 100% (5% MeCN in $H_2O$); 1.2-3.8 min: Ramp up to 10% (5% MeCN in $H_2O$)-90% MeCN; 3.8-4.4 min: Hold at 10% (5% MeCN in $H_2O$)-90% MeCN; 4.4-5.5 min: Ramp up to 100% MeCN; 5.5-6.0 min: Return to 100% (5% MeCN in $H_2O$). Method B: Phenomenex Mercury Luna 3μ $C_{18}$ column (2.0×10.0 mm, flow rate=1.5 mL/min), eluting with a (5% MeCN in $H_2O$)-MeCN solution (4:1 to 1:4) containing 0.1% $HCO_2H$ over 2.95 min, & employing diode array detection. The mass spectra for both Methods A and B were obtained employing an electrospray ionisation source in either the positive ($ES^+$) ion or negative ion ($ES^-$) mode. Atmospheric Pressure Chemical Ionisation (APCI) spectra were obtained on a FinniganMat SSQ 7000C instrument. The syntheses of the following compounds have been reported previously: 2-Amino-5-chloro-4-methylthiazole: S. Kyoichi et al. EP 412404; 2-Amino-5-formylthiazole: M. D. Frishberg U.S. Pat. No. 4,225,719; 5-Amino-[1,2,4]thiadiazole hydrochloride: Y. Yoshida et al. Bioorg. Med. Chem. 2000, 8, 2317-2335; 2-Chloromethylthiophene: G. Norcini et al. U.S. Pat. No. 5,716,943; Ethyl(4-mercaptophenyl)acetate: F. Gadient Ger. Offen. 2442979; Ethyl 4-(methylsulfanylphenyl)acetate: M. Kiuchi et al. J. Med. Chem. 2000, 43, 2946-2961; Ethyl(4-propylsulfanylphenyl)acetate: N. P. Buu-Hoi et al. Chim. Ther. 1967, 2, 39-48; Ethyl(4-[1,2,3]triazol-1-ylphenyl)acetate: G. Biagi et al. Farmaco Ed. Sci. 1988, 43, 597-611; Ethyl(4-[1,2,4]triazol-1-ylphenyl)acetate: M. Artico et al. Eur. J. Med. Chem. 1992, 27, 219-228; (3-Fluoro-4-methylsulfanylphenyl)acetic acid: L. B. Snyder and Z. Zheng WO 00/10566; 4-Iodomethyltetrahydropyran: D. J. Anderson et al. WO 95/30670; 4-Iodotetrahydropyran: Heuberger and Owen J. Chem. Soc. 1952, 910-913; Methyl(3-bromo-4-methylsulfanylphenyl)acetate: F. T. Bizzarro et al. WO 00/58293; Methyl 4-tert-butoxycarbonylmethylbenzoate: F. Agnelli and G. A. Sulikowski Tetrahedron Lett. 1998, 39, 8807-8810; (4-Methylsulfanylmethylphenyl)acetic acid: T. Tanaka et. al. JP 54079247; (3R)-3-(Tosyloxy)tetrahydrofuran: A. Bouzide et al. Tetrahedron Lett. 2001, 42, 8781-8783; (3S)-3-(Tosyloxy)tetrahydrofuran: F. J. A. Hundscheid et al. Tetrahedron 1987, 43, 5073-5088; 3-(Tosyloxy)oxetane: K. Baum et al. J. Org. Chem. 1983, 48, 2953-2956. (E)-2-Phenyl-3-thiophen-2-yl acrylic acid was purchased from Maybridge (Tintagel, UK).

Abbreviations and acronyms: Ac; Acetyl; i-Am. Isopentyl; ATP: Adenosine 5'-triphosphate; BOP: Benzotriazol-1-yloxytris(dimethylamino)phosphonium hexafluorophosphate; n-Bu: n-Butyl; t-Bu: tert-Butyl; Bz: Benzoyl; dba: dibenzylideneacetone; DIPEA: N,N-Diisopropylethylamine; DMAc: N,N-Dimethylacetamide; DME: 1,2-Dimethoxyethane; DMF: N,N-Dimethylformamide; DMPU: 1,3-Dimethyl-3,4,5,6-tetrahydro-2(1H)-pyrimidinone; DMSO: Dimethylsulfoxide; DPEPhos: Bis(2-diphenylphosphinophenyl)ether; EDCI: 1-(3-Dimethylaminopropyl)-3-ethylcarbodiimide hydrochloride; Et: Ethyl; FA: Fold activation; GK: Glucokinase; Glc: Glucose; G6P: Glucose-6-phosphate; G6PDH: Glucose-6-phosphate dehydrogenase; GST-GK: Glutathione S-transferase-Glucokinase fusion protein; HATU: O-(7-Azabenzotriazol-1-yl)-N,N,N',N'-tetramethyluronium hexafluorophosphate; HOBt: 1-Hydroxybenzotriazole; IH: Isohexane; i-Pr: Isopropyl; LDA: Lithium diisopropylamide; LHMDS: Lithium bis(trimethylsilyl)amide; mCPBA: 3-Chloroperoxybenzoic acid; Me: Methyl; mp: Melting point; NADP(H): β-Nicotinamide adenine dinucleotide phosphate (reduced); NBS: N-Bromosuccinimide; Ph: Phenyl; PS: Polymer supported; $R_F$: Retention factor; RT: Retention time; $RT^A$: Retention time with Method A; $RT^B$: Retention time with Method B; RP-HPLC: Reverse phase-high performance liquid chromatography; TBA-OX: Tetrabutylammonium oxone; TFA: Trifluoroacetic acid; TFAA: Trifluoroacetic anhydride; TFFH: Fluoro-N,N,N',N'-tetramethylformamidinium hexafluorophosphate; THF: Tetrahydrofuran.

Preparation 1: (E)-2-(4-Methanesulfonylphenyl)-3-thiophen-3-ylacrylic acid

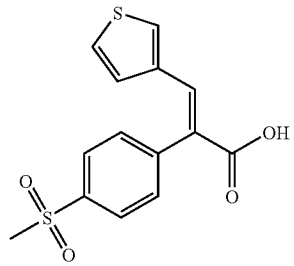

A mixture of 3-thiophenecarboxaldehyde (1.40 mL, 15.0 mmol), (4-methanesulfonylphenyl)acetic acid (3.23 g, 15.0 mmol), and piperidine (0.45 mL, 4.5 mmol) in PhMe (21 mL) was heated under reflux with stirring for 16 h. On cooling, the PhMe was decanted off from the oily solid that had settled at the bottom of the reaction vessel. This solid was partitioned between 1M HCl (60 mL) and EtOAc (400 mL), then the aqueous phase was extracted further with EtOAc (60 mL).

The combined organic layers were washed with H₂O (60 mL), before being shaken with saturated aqueous Na₂CO₃ (100 mL). The resulting emulsion was filtered through Celite. The organic layer was extracted further with saturated aqueous Na₂CO₃ (2×100 mL). The combined aqueous layers were washed with Et₂O (80 mL), before being filtered through Celite and carefully acidified with AcOH to adjust the pH to 4. The off-white precipitate formed was collected, washed thoroughly with H₂O, and air dried to furnished the title compound: m/z (ES$^+$)=634.2 [2M+NH$_4$]$^+$.

Several other acrylic acids were prepared (TABLE 1) by the piperidine-catalysed condensation of (4-methanesulfonylphenyl)acetic acid with the appropriate heteroaromatic aldehyde as described in Preparation 1.

TABLE 1

| Prep | Structure | Name | m/z(E$^+$) |
|---|---|---|---|
| 2 | 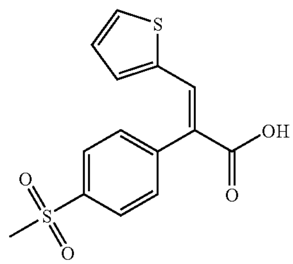 | (E)-2-(4-Methanesulfonylphenyl)-3-thiophen-2-ylacrylic acid | 634.1 [2M + NH$_4$]$^+$ |
| 3 | 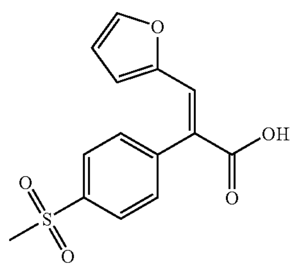 | (E)-3-Furan-2-yl-2-(4-methanesulfonylphenyl)acrylic acid | 310.1 [M + NH$_4$]$^+$ |
| 4 | 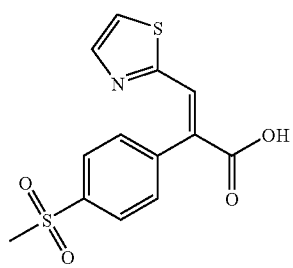 | (E)-2-(4-Methanesulfonylphenyl)-3-thiazol-2-ylacrylic acid | 310.2 [M + H]$^+$ |
| 5 | 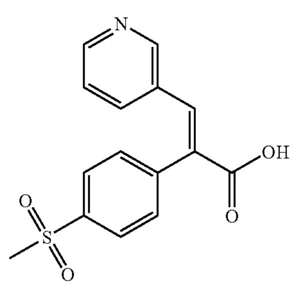 | (E)-2-(4-Methanesulfonylphenyl)-3-pyridin-3-ylacrylic acid | 345.1 [M + MeCN + H]$^+$ |
| 6 | 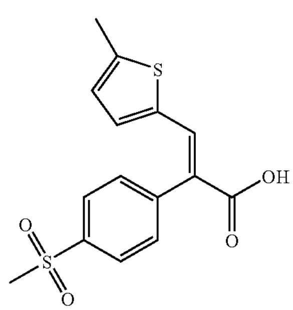 | (E)-2-(4-Methanesulfonylphenyl)-3-(5-methylthiophen-2-yl)acrylic acid | 340.1 [M + NH$_4$]$^+$ |

TABLE 1-continued

| Prep | Structure | Name | m/z(E⁺) |
|---|---|---|---|
| 7 | 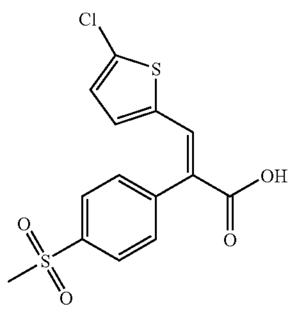 | (E)-3-(5-Chlorothiophen-2-yl)-2-(4-methanesulfonylphenyl)acrylic acid | 360.0 [M + NH$_4$]⁺ |
| 8 | 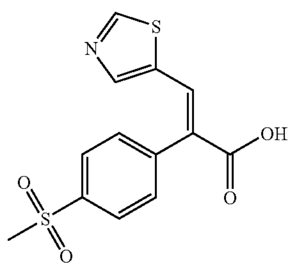 | (E)-2-(4-Methanesulfonylphenyl)-3-thiazol-5-ylacrylic acid | 310.1 [M + H]⁺ |

Preparation 9: (E)-2-(4-Bromophenyl)-3-furan-2-ylacrylic acid

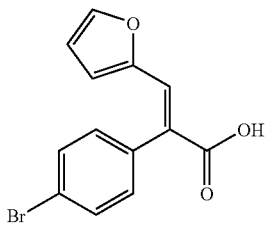

A mixture of 4-bromophenylacetic acid (12.90 g, 60.0 mmol), 2-furancarboxaldehyde (6.0 mL, 72.0 mmol), NEt$_3$ (12.0 mL, 86.4 mmol), and Ac$_2$O (12.0 mL, 127.2 mmol) were heated at 140° C. (bath) with stirring for 1¾ h. The reaction mixture was cooled in an ice bath, before being treated with 2M HCl (30 mL) to adjust the pH to 1. A solid precipitated out of solution. This solid was extracted into Et$_2$O (500 mL). The Et$_2$O layer was washed with H$_2$O (100 mL), before being extracted with 5% w/v aqueous Na$_2$CO$_3$ solution (5×100 mL). The aqueous extracts were washed with Et$_2$O (2×50 mL), before being carefully acidified with AcOH to pH 6. The cream solid generated was collected, washed with H$_2$O, and recrystallised from MeOH—H$_2$O to give the title compound: m/z (ES⁺)=604.0 [2M+NH$_4$]⁺.

The Perkin Condensation, using NEt$_3$ and Ac$_2$O, was used to make other acrylic acids (TABLE 2) from the appropriate arylacetic acid and (hetero)aromatic aldehyde as described in Preparation 9.

TABLE 2

| Prep | Structure | Name | m/z(E⁺) |
|---|---|---|---|
| 10 | 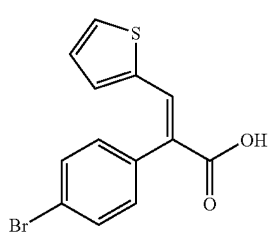 | (E)-2-(4-Bromophenyl)-3-thiophen-2-ylacrylic acid | 636.1 [2M + NH$_4$]⁺ |

TABLE 2-continued

| Prep | Structure | Name | m/z(E+) |
|---|---|---|---|
| 11 | 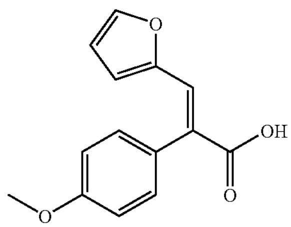 | (E)-3-Furan-2-yl-2-(4-methoxyphenyl)acrylic acid | 245.4 [M + H]+ |
| 12 | 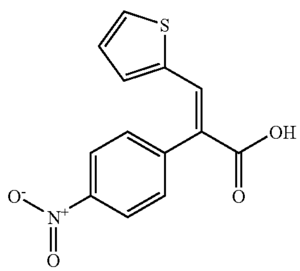 | (E)-2-(4-Nitrophenyl)-3-thiophen-2-ylacrylic acid | 568.2 [2M + NH4]+ |
| 13 | 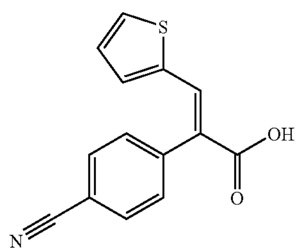 | (E)-2-(4-Cyanophenyl)-3-thiophen-2-ylacrylic acid | 528.2 [2M + NH4]+ |
| 14 | 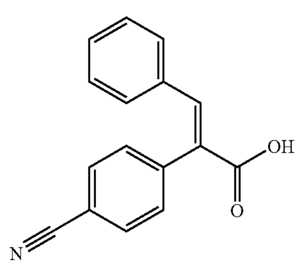 | (E)-2-(4-Cyanophenyl)-3-phenylacrylic acid | 516.3 [2M + NH4]+ |

Preparation 15:
Ethyl(4-methanesulfonylphenyl)acetate

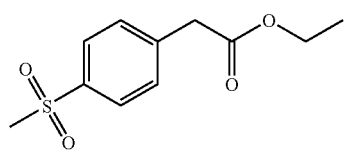

SOCl$_2$ (8.2 mL, 112.0 mmol) was added to a stirred suspension of (4-methanesulfonylphenyl)acetic acid (20.00 g, 93.3 mmol) in EtOH (80 mL) at −10° C. The mixture was allowed to warm up to 20° C. over 16 h, then the solvents were removed under reduced pressure. The remainder was dissolved in EtOAc, then the resulting solution was washed with H$_2$O until the pH of the aqueous phase was neutral. The EtOAc solution was washed further with saturated aqueous Na$_2$CO$_3$, before being dried (MgSO$_4$). Filtration and solvent evaporation furnished the title compound: m/z (ES+)=284.1 [M+MeCN+H]+.

Preparation 16:
Ethyl(4-methylsulfanylmethylphenyl)acetate

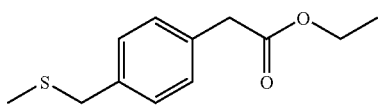

(4-Methylsulfanylmethylphenyl)acetic acid (2.00 g, 10.2 mmol) was esterified as described above in Preparation 15 to give the title compound: m/z (ES+)=242.2 [M+NH4]+.

Preparation 17:
Ethyl(3-fluoro-4-methylsulfanylphenyl)acetate

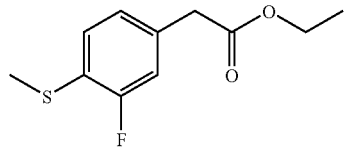

(3-Fluoro-4-methylsulfanylphenyl)acetic acid (7.54 g, 37.7 mmol) was esterified as described above in Preparation 15 to give the title compound: RT[A]=3.62 min.

Preparation 18:
Ethyl(4-methanesulfinylphenyl)acetate

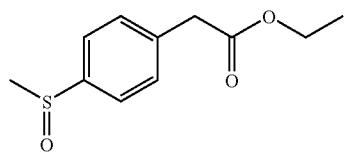

mCPBA (3.82 g of 65% pure, 22.2 mmol) was added portionwise to a stirred solution of ethyl 4-(methylsulfanylphenyl)acetate (4.66 g, 22.2 mmol) in $CH_2Cl_2$ (70 mL) while cooling with an ice-$H_2O$ bath. The mixture was stirred for 4 d at 20° C., before being quenched with saturated aqueous $Na_2CO_3$. The organic layer was separated, washed with saturated aqueous $NaHCO_3$, and dried ($MgSO_4$). Filtration, solvent evaporation, and flash chromatography (IH-EtOAc, 1:1 to 0:1) furnished the title compound: m/z ($ES^+$)=227.0 $[M+H]^+$.

Preparation 19:
Ethyl(4-ethanesulfonylphenyl)acetate

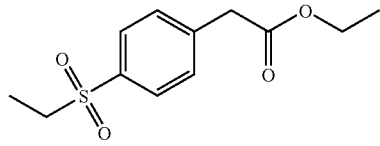

Alkylation of ethyl(4-mercaptophenyl)acetate (20 g, 102 mmol) with EtI (9.8 mL, 122 mmol), using a similar procedure to that described in Preparation 39, furnished ethyl(4-ethylsulfanylphenyl)acetate: m/z ($ES^+$)=225.2 $[M+H]^+$. Oxidation of this compound (22.6 g, 101 mmol) with mCPBA (222 mmol), employing a protocol similar to that described in Preparation 22, provided the title compound: m/z ($ES^+$)= 298.2 $[M+MeCN+H]^+$.

Preparation 20:
Ethyl[4-(propane-1-sulfonyl)phenyl]acetate

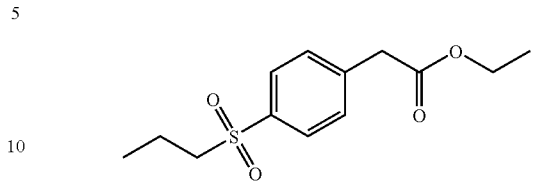

Ethyl(4-propylsulfanylphenyl)acetate (20.0 g, 83.9 mmol) was oxidised with mCPBA (172.0 mmol), employing a protocol similar to that described in Preparation 22, to afford the title compound: m/z ($ES^+$)=312.2 $[M+MeCN+H]^+$.

Preparation 21:
Triphenyl(tetrahydropyran-4-ylmethyl)phosphonium iodide

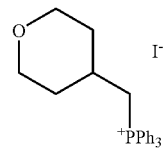

A stirred solution of 4-iodomethyltetrahydropyran (3.43 g, 15.2 mmol) and $PPh_3$ (3.98 g, 15.2 mmol) in anhydrous MeCN (10 mL) was heated under reflux for 19 h. On cooling to 20° C., $Et_2O$ (50 mL) was added. The precipitate formed was collected, washed with $Et_2O$ (150 mL), and recrystallised (MeCN) to give the title compound: m/z ($ES^+$)=361.2 $[M]^+$.

Preparation 22: 2-(4-Cyclopropanesulfonylphenyl)-3-(tetrahydropyran-4-yl)propionic acid

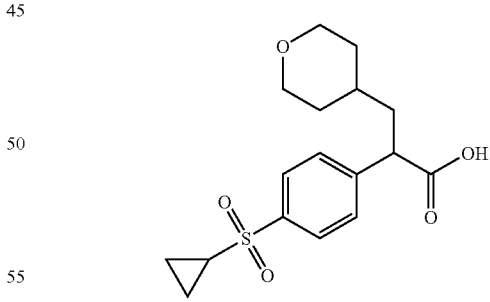

A stirred suspension of $AlCl_3$ (12.90 g, 96.8 mmol) in anhydrous $CH_2Cl_2$ (135 mL) was treated portionwise at 0° C. with ethyl chlorooxoacetate (8.5 mL, 76.0 mmol). Cyclopropyl phenyl sulfide (10.0 mL, 70.0 mmol) was added to the mixture dropwise over 1 h while maintaining the reaction temperature below 10° C. The mixture was allowed to warm to 20° C., before being stirred for an additional 70 min. Ice cold $H_2O$ (35 mL) was added on cooling to 0° C., then the mixture was stirred further for 10 min. The $CH_2Cl_2$ layer was separated, then the aqueous layer was extracted with more $CH_2Cl_2$ (2×50 mL). The combined organic layers were dried ($MgSO_4$), filtered and concentrated to give ethyl(4-cyclopropylsulfanylphenyl)oxoacetate: $RT^B$=1.74 min. LHMDS (3.7 mL of a 1.0M solution in THF, 3.7 mmol) was added to a stirred suspension of triphenyl(tetrahydropyran-4-ylmethyl)phosphonium iodide (Preparation 21, 1.82 g, 3.7 mmol) in anhydrous THF (5.6 mL) at 0° C. After 1 h, a solution of ethyl(4-cyclopropylsulfanylphenyl)oxoacetate (0.78 g, 3.1 mmol) in anhydrous THF (4 mL) was added over 5 min. The mixture was stirred at 0° C. for 1 h, before being allowed to warm to 20° C. over 16 h. $H_2O$ (7 mL) was added on cooling down to 0° C. 1M HCl was added to adjust the pH to 6, then the mixture was stirred for 1 h at 20° C. The THF was removed in vacuo, then $Et_2O$ (35 mL) was added. The mixture was stirred for 30 min and filtered, washing with $Et_2O$. The aqueous layer was separated and extracted with $Et_2O$ (3×10 mL). The combined organic extracts were washed with brine (20 mL), dried, filtered, and concentrated. Flash chromatography ($IH-CH_2Cl_2$, 2:1 to 1:1, followed by $THF-CH_2Cl_2$, 1:99) yielded ethyl 2-(4-cyclopropylsulfanylphenyl)-3-(tetrahydropyran-4-yl)acrylate: m/z $(ES^+)$=333.2 $[M+H]^+$. A stirred solution of this thioether (609 mg, 1.83 mmol) in $CH_2Cl_2$ (35 mL) was treated with a solution of mCPBA (992 mg of 65% pure, 3.74 mmol) in $CH_2Cl_2$ (15 mL). After 6 h, saturated aqueous $NaHCO_3$ (25 mL) was added, then stirring was continued for 5 min. The layers were separated, then the aqueous phase was extracted with $CH_2Cl_2$ (20 mL). The combined organic layers were washed with saturated aqueous $NaHCO_3$ (25 mL), $H_2O$ (25 mL), and brine (25 mL), before being dried ($MgSO_4$). Filtration and solvent evaporation gave ethyl 2-(4-cyclopropanesulfonylphenyl)-3-(tetrahydropyran-4-yl)acrylate: m/z $(ES^+)$=382.2 $[M+NH_4]^+$. A solution of this compound (667 mg, 1.83 mmol) in EtOAc (60 mL) was treated with Pd (10% on C, 424 mg, 0.39 mmol). The reaction mixture was stirred under a $H_2$ atmosphere for 3 d, before being filtered through Celite. The Celite was washed with EtOAc (100 mL), then the combined filtrates were concentrated to give ethyl 2-(4-cyclopropanesulfonylphenyl)-3-(tetrahydropyran-4-yl)propionate: $R_F$ ($CH_2Cl_2$-THF, 30:1)=0.56. A solution of this ester (664 mg, 1.81 mmol) in $THF-H_2O$ (3:1, 20 mL) was stirred with $LiOH.H_2O$ (168 mg, 4.00 mmol) for 23 h. The THF was evaporated off under reduced pressure, then the remainder was diluted with $H_2O$ (10 mL). The mixture was washed with $Et_2O$ (2×20 mL), before being acidified with 2M HCl (5 mL) to pH 1. The remainder was extracted with EtOAc (3×20 mL). The combined organic extracts were washed with brine (20 mL), dried ($MgSO_4$), filtered, and evaporated to give the title compound: m/z $(ES^+)$=694.4 $[2M+NH_4]^+$.

Preparation 23: (E)-2-(4-Cyclopropanesulfonylphenyl)-3-(tetrahydropyran-4-yl)acrylic acid

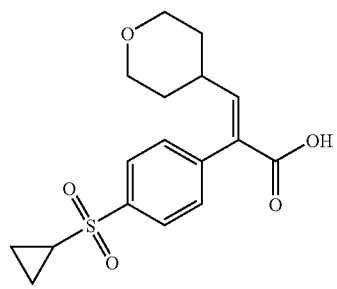

Ethyl 2-(4-cyclopropanesulfonylphenyl)-3-(tetrahydropyran-4-yl)acrylate (see Preparation 22, 3.44 g, 9.44 mmol) was saponified, using the procedure described in Preparation 25, to afford the title compound: m/z $(ES^+)$=673.5 $[2M+H]^+$.

Preparation 24: (E)-2-(4-Cyclopropanesulfinylphenyl)-3-(tetrahydropyran-4-yl)acrylic acid

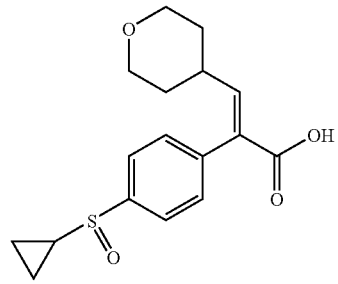

Partial oxidation of ethyl 2-(4-cyclopropylsulfanylphenyl)-3-(tetrahydropyran-4-yl)acrylate (see Preparation 22, 3.14 g, 9.44 mmol) with mCPBA, employing the protocol described above in Preparation 18, furnished ethyl 2-(4-cyclopropanesulfinylphenyl)-3-(tetrahydropyran-4-yl)acrylate: m/z $(ES^+)$=349.2 $[M+H]^+$. Saponification of this ester (1.15 g, 3.3 mmol), using the procedure described in Preparation 25, afforded the title compound: m/z $(ES^+)$=641.4 $[2M+H]^+$.

Preparation 25: (E)-2-(4-Methanesulfonylphenyl)-3-(tetrahydropyran-4-yl)acrylic acid

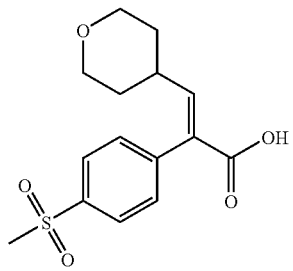

LDA (24 mL of a 1.8M solution in $n-C_7H_{16}$-THF-PhEt, 43.3 mmol) was added dropwise to a stirred solution of DMPU (19 mL, 153.0 mmol) in anhydrous THF (100 mL) at −78° C. After 30 min, a solution of ethyl(4-methanesulfonylphenyl)acetate (Preparation 15, 5.00 g, 20.6 mmol) in anhydrous THF (42 mL) was added dropwise. The mixture was stirred further for 1 h, before being treated dropwise with a solution of tetrahydropyran-4-carboxaldehyde (2.36 g, 20.6 mmol) in anhydrous THF (25 mL). After being allowed to warm up to 20° C. over 16 h, the reaction was quenched with saturated aqueous $NH_4Cl$ (210 mL). The THF was removed under reduced pressure, then the remainder was extracted with EtOAc (3×250 mL). The combined EtOAc extracts were dried (MgSO$_4$), filtered, and concentrated. Column chromatography (IH-EtOAc, 7:3) furnished (E)-ethyl 2-(4-methanesulfonylphenyl)-3-(tetrahydropyran-4-yl)acrylate: m/z (ES$^+$)=356.2 [M+NH$_4$]$^+$. A solution of this ester (6.46 g, 19.1 mmol) in MeOH (30 mL) and 1M NaOH (40 mL, 40.0 mmol) was heated under reflux for 1 h. On cooling, the mixture was washed with EtOAc. The aqueous phase was acidified with 1M HCl, before being extracted with EtOAc. The combined organic extracts were dried (MgSO$_4$). Filtration and solvent evaporation afforded the title compound: m/z (ES$^+$)=621.3 [2M+H]$^+$.

The acrylic acids listed in TABLE 3 were synthesised employing similar methods to those described in Preparation 25.

TABLE 3

| Prep | Structure | Name | m/z(E$^+$) |
|------|-----------|------|------------|
| 26 | 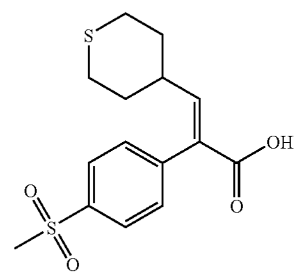 | (E)-2-(4-Methanesulfonylphenyl)-3-(tetrahydrothiopyran-4-yl)acrylic acid | 653.3 [2M + H]$^+$ |
| 27 | 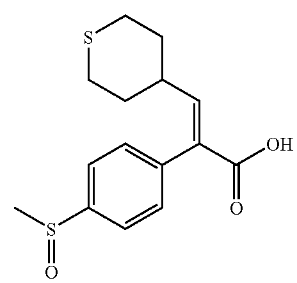 | (E)-2-(4-Methanesulfinylphenyl)-3-(tetrahydrothiopyran-4-yl)acrylic acid | 621.3 [2M + H]$^+$ |
| 28 | 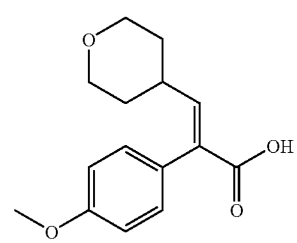 | (E)-2-(4-Methoxyphenyl)-3-(tetrahydropyran-4-yl)acrylic acid | 525.3 [2M + H]$^+$ |
| 29 | 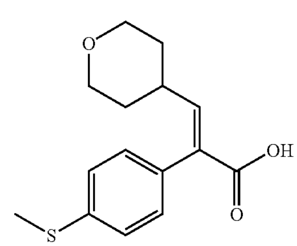 | (E)-2-(4-Methanesulfanylphenyl)-3-(tetrahydropyran-4-yl)acrylic acid | 557.3 [2M + H]$^+$ |

Preparation 30: (E)-3-(Tetrahydropyran-4-yl)-2-(4-[1,2,3]triazol-1-ylphenyl)acrylic acid

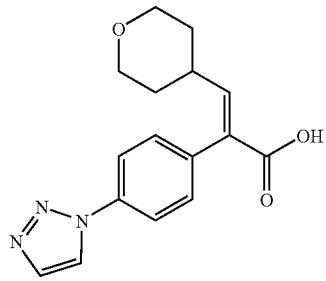

NaOEt (0.63 mL of a 0.5M solution in EtOH, 0.32 mmol) was added dropwise to a stirred solution of ethyl(4-[1,2,3] triazol-1-ylphenyl)acetate (730 mg, 3.16 mmol) and tetrahydropyran-4-carboxaldehyde (396 mg, 3.47 mmol) in anhydrous DMSO (3 mL). The mixture was heated at 80° C. for 16 h, before being treated with AcOH to adjust the pH to 7. EtOAc (30 mL) was added, then the solution was washed with $H_2O$ (2×10 mL) and brine (10 mL), before being dried ($MgSO_4$). Filtration, solvent evaporation, and column chromatography (IH-EtOAc, 1:1) yielded ethyl 3-(tetrahydropyran-4-yl)-2(4-[1,2,3]triazol-1-ylphenyl)acrylate: m/z ($ES^+$)= 328.2 $[M+H]^+$. This ester (404 mg, 1.23 mmol) was saponified as described above in Preparation 25 to give the title compound: m/z ($ES^+$)=300.2 $[M+H]^+$.

The method detailed in Preparation 30, involving the condensation of a phenylacetic ester with the appropriate aldehyde followed by saponification of the intermediate α,β-unsaturated ester, was employed to prepare the acrylic acids listed in TABLE 4.

TABLE 4

| Prep | Structure | Name | m/z ($ES^+$ or $ES^-$) |
|---|---|---|---|
| 31 | 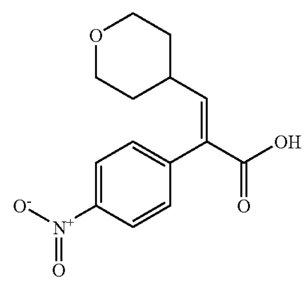 | (E)-2-(4-Nitrophenyl)-3-(tetrahydropyran-4-yl)acrylic acid | 572.4 $[2M + NH_4]^+$ |
| 32 | 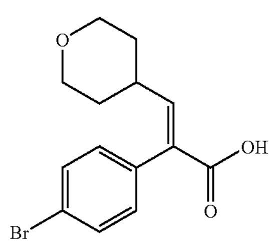 | (E)-2-(4-Bromophenyl)-3-(tetrahydropyran-4-yl)acrylic acid | 329.1 $[M + NH_4]^+$ |
| 33 | 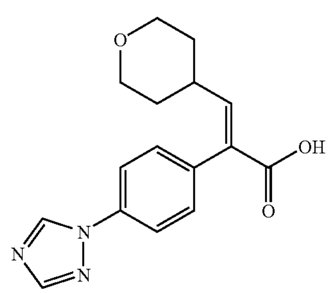 | (E)-3-(Tetrahydropyran-4-yl)-2-(4-[1,2,4]triazol-1-ylphenyl)acrylic acid | 300.2 $[M + H]^+$ |

TABLE 4-continued

| Prep | Name | m/z (ES⁺ or ES⁻) |
|---|---|---|
| 34 | (E)-3-(Tetrahydrothiopyran-4-yl)-2-(4-[1,2,4]triazol-1-ylphenyl)acrylic acid | 316.1 [M + H]⁺ |
| 35 | (E)-tert-Butyl-4[2-carboxy-2-(4-methanesulfonylphenyl)vinyl]piperidine-1-carboxylate | 427.0 [M + NH₄]⁺ |
| 36 | (E)-2-(4-Ethanesulfonylphenyl)-3-tetrahydropyran-4-yl)acrylic acid | 647.3 [2M − H]⁻ |
| 37 | (E)-2-[4-(Propane-1-sulfonyl)phenyl]-3-tetrahydropyran-4-yl)acrylic acid | 337.0 [M − H]⁻ |

Preparation 38: 2-(4-Methanesulfonylphenyl)-3-thiophen-2-ylpropionic acid

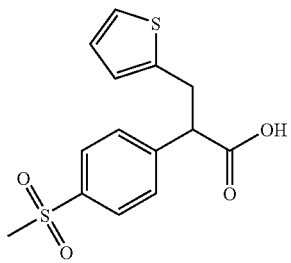

DMPU (50 mL, 413 mmol) was added to a solution of LDA (65 mL of a 1.8M solution in n-$C_7H_{16}$-THF-PhEt, 117 mmol) in anhydrous THF (250 mL) at −78° C. The mixture was stirred for 1 h to generate a cream precipitate. A solution of (4-methanesulfonylphenyl)acetic acid (12.00 g, 56 mmol) in anhydrous THF (120 mL) was added over 20 min. More anhydrous THF (30 mL) was added, then the thick yellow slurry was stirred for 1 h. The mixture was treated with a solution of 2-chloromethylthiophene (7.50 g, 57 mmol) and PhMe (5.20 g, 57 mmol) in anhydrous THF (20 mL), then stirring was continued at −78° C. for 20 min. The reaction mixture was then allowed to warm to 20° C. over 16 h, before being quenched with $H_2O$ (500 mL). The THF was removed under reduced pressure, then 12M HCl was added to adjust the pH to 2. The mixture was extracted with EtOAc (2×300 mL), then the extracts were washed with $H_2O$ (2×200 mL) and brine (2×100 mL), before being dried ($MgSO_4$). Filtration, solvent evaporation, and column chromatography (IH-EtOAc, 3:2 containing 0.5% AcOH) furnished the title compound: m/z ($ES^+$)=638.3 [$2M+NH_4$]$^+$.

Preparation 39: Ethyl[4-(tetrahydropyran-4-ylsulfanyl)phenyl]acetate

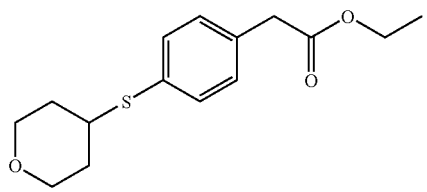

$NEt_3$ (1.3 mL, 9.0 mmol) and 4-iodotetrahydropyran (1.93 g, 9.0 mmol) were added to a stirred solution of ethyl(4-mercaptophenyl)acetate (1.21 g, 6.0 mmol) in anhydrous DMF (10 mL) at 0° C. The mixture was allowed to warm to room temperature over 3 d, then the solvents were removed under reduced pressure. The residue was partitioned between $Et_2O$ (100 mL) and saturated aqueous $NH_4Cl$ (50 mL), the aqueous phase being extracted further with $Et_2O$ (45 mL). The combined ethereal extracts were washed with $H_2O$ (50 mL), $H_2O$-saturated aqueous $Na_2CO_3$ (1:1, 50 mL), and brine (50 mL), before being dried ($MgSO_4$). Filtration, solvent evaporation, and flash chromatography (IH-$Et_2O$, 10:1 to 2:1) afforded the title compound: $R_F$ (IH-$Et_2O$, 2:1)=0.31.

Preparation 40: Ethyl(4-methoxymethylsulfanylphenyl)acetate

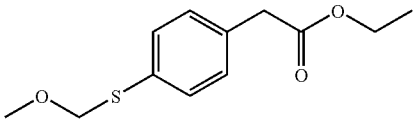

This compound was prepared using the procedure described above in Preparation 39: $R_F$ (IH-$Et_2O$, 10:1)=0.19.

Preparation 41: 2-(4-Methanesulfonylphenyl)-3-(tetrahydropyran-4-yl)propionic acid

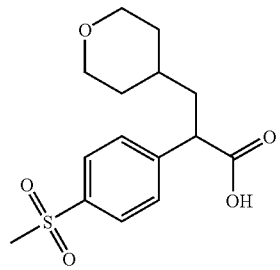

LDA (38.9 mL of a 1.8M solution in n-$C_7H_{16}$-THF-PhEt, 70.0 mmol) was added to a solution of DMPU (59.3 mL, 490.3 mmol) in anhydrous THF (150 mL) at −78° C. The mixture was stirred for 30 min, before being treated dropwise with a solution of ethyl(4-methanesulfonylphenyl)acetate (Preparation 15, 16.97 g, 70.0 mmol) in anhydrous THF (50 mL). Stirring was continued at −78° C. for 45 min, then a solution of 4-iodomethyltetrahydropyran (19.00 g, 84.0 mmol) in anhydrous THF (40 mL) was added. The mixture was allowed to warm to 20° C. over 16 h, before being quenched with 1M HCl (70 mL). The THF was removed under reduced pressure, then more $H_2O$ (40 mL) was added and the remainder extracted with EtOAc (2×250 mL). The EtOAc extracts were dried ($MgSO_4$). Filtration, solvent evaporation, and flash chromatography (IH-EtOAc, 9:1 to 1:1) furnished ethyl 2-(4-methanesulfonylphenyl)-3-(tetrahydropyran-4-yl)propionate: m/z ($ES^+$)=698.3 [$2M+NH_4$]$^+$. A solution of this compound (20.27 g, 59.6 mmol) in MeOH (100 mL) and 2M NaOH (62.5 mL, 125.0 mmol) was heated under reflux for 1 h. The solvents were removed under reduced pressure, then the remaining solid was triturated with $Et_2O$ (5×100 mL), before being dissolved in $H_2O$ (100 mL). The aqueous solution was washed with EtOAc (50 mL), acidified with 2M HCl to pH 1, and extracted with EtOAc (2×1 L). After drying ($MgSO_4$), filtration and solvent evaporation gave the title compound: m/z ($ES^+$)=642.3 [$2M+NH_4$]$^+$.

Similar approaches to those highlighted by Preparation 41, involving alkylation of the appropriate ester with 4-iodomethyltetrahydropyran followed by hydrolysis of the product, were employed to prepare the carboxylic acids shown in TABLE 5.

TABLE 5

| Prep | Structure | Name | m/z (ES+ or ES−) |
|---|---|---|---|
| 42 | 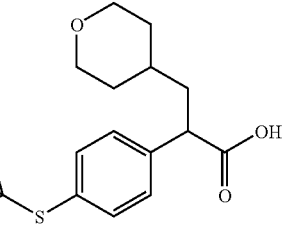 | 3-(Tetrahydropyran-4-yl)-2-(4-trifluoromethylsulfanylphenyl)propionic acid | 669.3 [2M + H]+ |
| 43 | 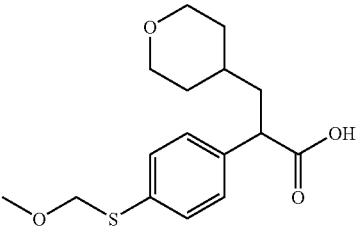 | 2-(4-Methoxymethylsulfanylphenyl)-3-(tetrahydropyran-4-yl)propionic acid | 638.4 [2M + NH4]+ |
| 44 | 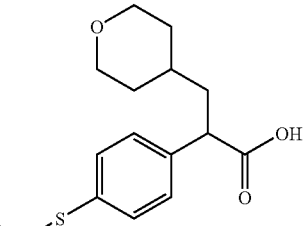 | 3-(Tetrahydropyran-4-yl)-2-[4-(tetrahydropyran-4-ylsulfanyl)phenyl]-propionic acid | 351.2 [M + H]+ |
| 45 | 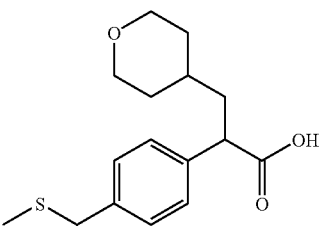 | 2-(4-Methylsulfanylmethylphenyl)-3-(tetrahydropyran-4-yl)propionic acid | 589.1 [2M + H]+ |
| 46 | 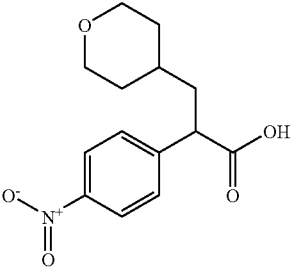 | 2-(4-Nitrophenyl)-3-tetrahydropyran-4-yl)propionic acid | 576.4 [2M + NH4]+ |

TABLE 5-continued

| Prep | Structure | Name | m/z (ES+ or ES−) |
|---|---|---|---|
| 47 | 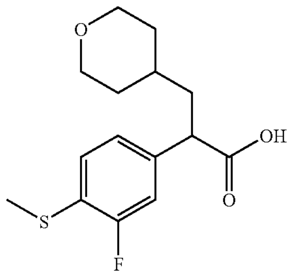 | 2-(3-Fluoro-4-methylsulfanylphenyl)-3-(tetrahydropyran-4-yl)propionic acid | 597.4 [2M + H]+ |
| 48 | 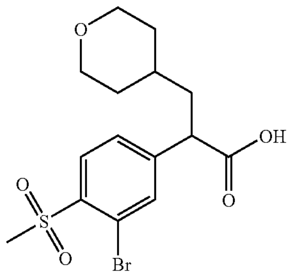 | 2-(3-Bromo-4-methanesulfonylphenyl)-3-(tetrahydropyran-4-yl)propionic acid | 408.1 [M + NH4]+ |
| 49 | 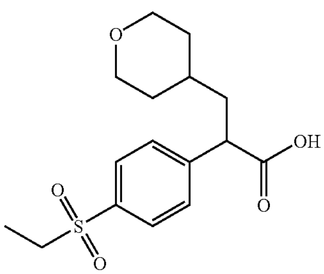 | 2-(4-Ethanesulfonylphenyl)-3-(tetrahydropyran-4-yl)propionic acid | 651.4 [2M − H]− |

Preparation 50: 2-(3-Fluoro-4-methanesulfonylphenyl)-3-(tetrahydropyran-4-yl)propionic acid

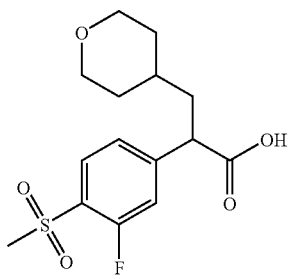

A stirred solution of 2-(3-fluoro-4-methylsulfanylphenyl)-3-(tetrahydropyran-4-yl)propionic acid (Preparation 47, 598 mg, 2.0 mmol) in CH$_2$Cl$_2$ (20 mL) was treated with mCPBA (1.15 g of 60% pure, 4.0 mmol). After 16 h, the solution was filtered, then the filtrate was purified by column chromatography (IH-EtOAc-AcOH, 320:80:1 to 80:320:1) to furnish the title compound: m/z (ES+)=678.3 [2M+NH4]+.

Preparation 51: 2-(4-Ethysulfamoylphenyl)-3-(tetrahydropyran-4-yl)propionic acid

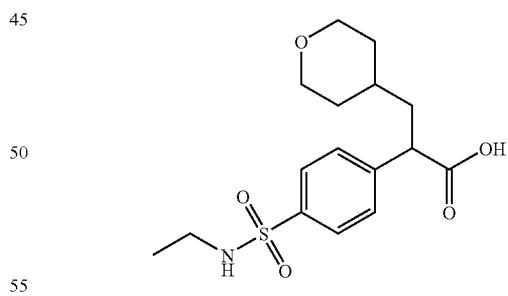

Ethyl(4-nitrophenyl)acetate (25.0 g, 119.5 mmol) was alkylated with 4-iodomethyltetrahydropyran (32.4 g, 143.4 mmol), according to the protocol described in Preparation 41, to give ethyl 2-(4-nitrophenyl)-3-(tetrahydropyran-4-yl)propionate: $\delta_H$ (CDCl$_3$): 1.21 (3H, t), 1.25-1.45 (3H, m), 1.55-1.65 (2H, m), 1.70-1.80 (1H, m), 2.05-2.15 (1H, m), 3.25-3.35 (2H, m), 3.79 (1H, t), 3.90-3.95 (2H, m), 4.10-4.20 (2H, m), 7.49 (2H, d), 8.19 (2H, d). The nitro group of this compound (6.55 g, 18.1 mmol) was reduced utilising the procedure described in EXAMPLE 145 to give ethyl 2-(4-aminophenyl)-3-(tetrahydropyran-4-yl)propionate: m/z (ES+)=

278.2 [M+H]⁺. This compound (30.5 g, 110 mmol) was transformed into ethyl 2-(4-chlorosulfonylphenyl)-3-(tetrahydropyran-4-yl)propionate employing the protocol described in Preparation 59. A solution of this sulfonyl chloride (33.6 g, 93.2 mmol) in anhydrous THF (100 mL) was added over 30 min at 0° C. to EtNH₂ (116.5 mL of a 2.0M solution in THF, 233.0 mmol). The mixture was warmed up to 20° C., before being stirred for 16 h. The suspension was filtered through a Celite pad, which was washed with THF (3×50 mL). The combined THF solutions were concentrated to furnish crude ethyl 2-(4-ethylsulfamoylphenyl)-3-(tetrahydropyran-4-yl)propionate: m/z (ES⁺)=370.2 [M+H]⁺. Hydrolysis of this ester (33.7 g, 91.2 mmol), utilising the procedure outlined in Preparation 41, followed by purification via RP-HPLC afforded the title compound: m/z (ES⁺)= 342.2 [M+H]⁺.

Preparation 52: 2-(4-Cyclobutanesulfonylphenyl)-3-(tetrahydropyran-4-yl)propionic acid

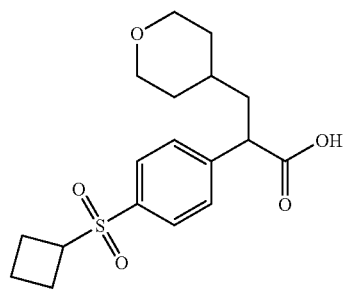

Alkylation of ethyl(4-mercaptophenyl)acetate (9.5 g, 48.4 mmol) with c-BuBr (7.84 g, 58.1 mmol), using a similar procedure to that described in EXAMPLE 161, furnished ethyl(4-cyclobutylsulfanylphenyl)acetate: RT⁴=4.17 min. Oxidation of this compound (18.5 g, 73.9 mmol) with mCPBA (222 mmol), employing a protocol similar to that described in Preparation 22, provided ethyl(4-cyclobutanesulfonylphenyl)acetate: m/z (ES⁺)=283.2 [M+H]⁺. Condensation of this compound (18.84 g, 66.7 mmol) with tetrahydropyran-4-carboxaldehyde (8.38 g, 73.4 mmol), utilising the procedure described in Preparation 30, gave ethyl 2-(4-cyclobutanesulfonylphenyl)-3-(tetrahydropyran-4-yl)acrylate: m/z (ES⁺)=396.2 [M+NH₄]⁺. Reduction of this α,β-unsaturated ester (13.00 g, 34.4 mmol), using the protocol described in Preparation 22, furnished ethyl 2-(4-cyclobutanesulfonylphenyl)-3-(tetrahydropyran-4-yl)propionate: m/z (ES⁺)= 381.2 [M+H]⁺. This ester was hydrolysed employing the procedure outlined in Preparation 22 to afford the title compound: m/z (ES⁺)=370.2 [M+NH₄]⁺.

Preparation 53: (2R)-2-(4-Methanesulfonylphenyl)-3-(tetrahydropyran-4-yl)propionic acid

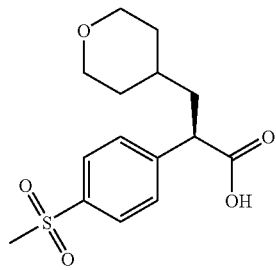

NEt₃ (15.4 mL, 110 mmol) was added to a stirred suspension of 2-(4-methanesulfonylphenyl)-3-(tetrahydropyran-4-yl)propanoic acid (Preparation 41, 30.0 g, 96.0 mmol) in anhydrous THF (300 mL) at 0° C. After 10 min, pivaloyl chloride (13.6 mL, 110 mmol) was added dropwise over 20 min and the mixture was stirred at 0° C. for 2 h. Meanwhile, n-BuLi (45.3 mL of a 2.5M solution in hexanes, 115 mmol) was added to a solution of (R)-(+)-4-benzyl-2-oxazolidinone (20.4 g, 115 mmol) in anhydrous THF (300 mL) at −78° C. The mixture was stirred at −78° C. to 20° C. over 2 h. The solution thus obtained was added dropwise to the abovementioned mixed anhydride solution at −78° C. The reaction was stirred at −78° C. for 1 h and then at 20° C. for 4 h, before being treated with H₂O (300 mL). The THF was removed in vacuo, then the remainder was extracted with EtOAc (3×300 mL). The combined organic layers were washed with H₂O, dried (Na₂SO₄), filtered, and concentrated in vacuo. Chromatographic separation (EtOAc-n-C₆H₁₄, 1:2 to 1:1) afforded two products: (1) (4R)-4-benzyl-3-[(2R)-2-[4-(methylsulfonyl)phenyl]-3-(tetrahydro-2H-pyran-4-yl)propanoyl]-1,3-oxazolidin-2-one: mp 139-141° C. (from Et₂O-THF); (2) (4R)-4-benzyl-3-[(2S)-2-[4-(methylsulfonyl)phenyl]-3-(tetrahydro-2H-pyran-4-yl)propanoyl]-1,3-oxazolidin-2-one: m/z (APCI⁺)=472 [M+H]⁺. A solution of LiOH (1.5 g, 64 mmol) and 35% aqueous H₂O₂ (14.5 g, 128 mmol) in H₂O (400 mL) was added dropwise over 40 min to a stirred solution of (4R)-4-benzyl-3-[(2R)-2-[4-(methylsulfonyl)phenyl]-3-(tetrahydro-2H-pyran-4-yl)propanoyl]-1,3-oxazolidin-2-one (15.1 g, 10.9 mmol) in THF-H₂O (3:1, 1.6 L) at 0° C. The reaction was stirred at 0° C. for 1.5 h, then the remaining oxidant was destroyed with 10% aqueous Na₂SO₃. The mixture was washed with Et₂O (4×300 mL), acidified with 10% aqueous HCl, and extracted with EtOAc (3×200 mL). The combined organic layers were washed with brine, dried (Na₂SO₄), filtered, and concentrated in vacuo. Trituration with Et₂O-hexanes gave the title compound: mp 217° C.; the absolute configuration was determined by X-ray crystallographic analysis.

Preparation 54: (2R)-2-(4-Cyclopropanesulfonylphenyl)-3-(tetrahydropyran-4-yl)propionic acid

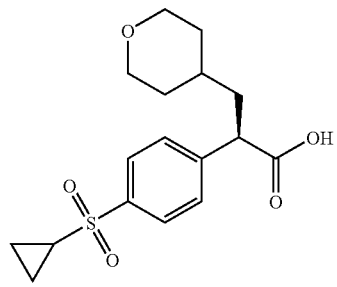

The title compound ($[\alpha]_D^{20}$ −48.8 (c=1.02, CHCl₃)) was obtained from 2-(4-cyclopropanesulfonylphenyl)-3-(tetrahydropyran-4-yl)propionic acid (Preparation 22) employing the protocols described in Preparation 53.

Preparation 55: (2R)-2-(4-Ethylsulfamoylphenyl)-3-(tetrahydropyran-4-yl)propionic acid

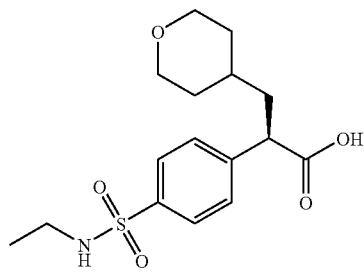

The title compound was obtained from 2-(4-ethylsulfamoylphenyl)-3-(tetrahydropyran-4-yl)propionic acid (Preparation 51) by employing the protocols described in Preparation 53. It was analysed by chiral HPLC: CHIRAL, CEL OJ-R® (Daicel Chemical Industries, Ltd., Tokyo, Japan), 4.6 mm ø×15 cm, CH$_3$CN-0.5M NaClO$_4$ (pH 2.0), 17:83, 0.5 mL/min, UV 235 nm, 25° C.; RT (R)=43.89 min (RT (S)=38.84 min).

Preparation 56: (2R)-2-(4-Cyclobutanesulfonylphenyl)-3-(tetrahydropyran-4-yl)propionic acid

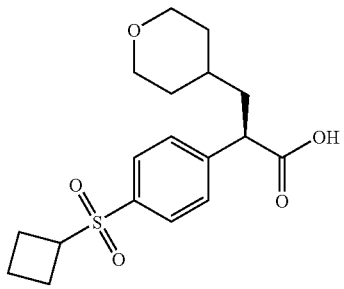

The enantiomerically pure title compound was obtained from 2-(4-cyclobutanesulfonylphenyl)-3-(tetrahydropyran-4-yl)propionic acid (Preparation 52) by employing the protocols described in Preparation 53. It was analysed by chiral HPLC: CHIRAL CEL OJ-R® (Daicel Chemical Industries, Ltd., Tokyo, Japan), 4.6 mm ø×15 cm, CH$_3$CN-0.5M NaClO$_4$ (pH 2.0), 17:83, 0.5 mL/min, UV 235 nm, 25° C.; RT (R)=82.69 min (RT (S)=78.63 min).

Preparation 57: 2-(4-Methylsulfanyl-3-nitrophenyl)-3-(tetrahydropyran-4-yl)propionic acid

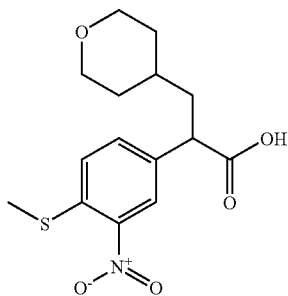

(4-Chloro-3-nitrophenyl)acetic acid (10.00 g, 46.4 mmol) was esterified as described above in Preparation 15 to furnish ethyl(4-chloro-3-nitrophenyl)acetate: m/z (ES$^+$)=285.2 [M+MeCN+H]$^+$. Alkylation of this ester (10.50 g, 43.1 mmol), using the protocol described in Preparation 41, yielded ethyl 2-(4-chloro-3-nitrophenyl)-3-(tetrahydropyran-4-yl)propionate: m/z (ES$^+$)=342.1 [M+H]$^+$. A solution of this compound (7.42 g, 19.7 mmol) in DMSO (50 mL) was treated with NaSMe (1.52 g, 21.6 mmol). The mixture was stirred at 20° C. for 5.5 h and then at 50° C. for 2 h, before being poured onto crushed ice (500 mL). After the ice had melted completely, the mixture was partitioned between EtOAc (250 mL) and H$_2$O (100 mL). The aqueous phase was further extracted with EtOAc (4×200 mL), then the combined organic extracts were washed with brine and dried (MgSO$_4$). Filtration, solvent evaporation, and column chromatography (IH-EtOAc, 7:3) gave ethyl 2-(4-methylsulfanyl-3-nitrophenyl)-3-(tetrahydropyran-4-yl)propionate: m/z (ES$^+$)=371.0 [M+NH$_4$]$^+$. This ester (7.48 g, 19.2 mmol) was hydrolysed with LiOH.H$_2$O, as described above in Preparation 22, to furnish the title compound: m/z (ES$^+$)=343.3 [M+NH$_4$]$^+$.

Preparation 58: 2-(3-Methylsulfanylphenyl)-3-(tetrahydropyran-4-yl)propionic acid

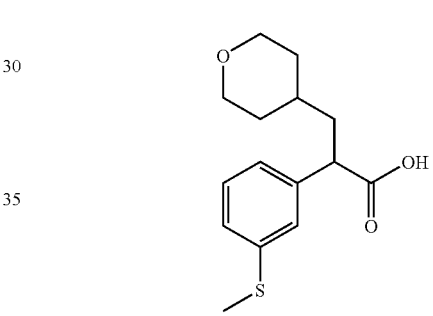

Ethyl(3-nitrophenyl)acetate (11.60 g, 55.5 mmol) was condensed with tetrahydropyran-4-carboxaldehyde employing the procedure described in Preparation 30 to give ethyl 2-(3-nitrophenyl)-3-(tetrahydropyran-4-yl)acrylate: m/z (ES$^+$)= 628.3 [2M+NH$_4$]$^+$. A solution of this compound (4.65 g, 15.2 mmol) in EtOH (80 mL) was treated with a slurry of Pd (10% on C, 49 mg, 0.46 mmol) in EtOH (10 mL) and H$_2$O (1 mL). The mixture was stirred under a H$_2$ atmosphere for 24 h, before being filtered through Celite. The Celite was washed with EtOAc (5×50 mL), then the combined filtrates were evaporated to give ethyl 2-(3-aminophenyl)-3-(tetrahydropyran-4-yl)propionate: m/z (ES$^+$)=278.2 [M+H]$^+$. A solution of this compound (2.77 g, 10.0 mmol) in DME (10 mL) was added over 30 min to a stirred mixture of i-AmONO (2.0 mL, 15.0 mmol) and MeSSMe (9.9 mL, 110.0 mmol). The temperature was raised to 45° C. for 0.5 h and then to 85° C. for 1.5 h. On cooling, the solvents were removed under reduced pressure, then the residue was dissolved in EtOAc (60 mL). The EtOAc solution was washed with 1M HCl (2×20 mL), H$_2$O (20 mL), and brine (20 mL). Filtration, solvent evaporation, and column chromatography (CH$_2$Cl$_2$-Et$_2$O, 1:0 to 99:1) afforded ethyl 2-(3-methylsulfanylphenyl)-3-(tetrahydropyran-4-yl)propionate: m/z (ES$^+$)=309.2 [M+H]$^+$. Saponification of this ester with LiOH.H$_2$O, by the protocol outlined in Preparation 22, furnished the title compound: m/z (ES$^+$)=561.3 [2M+H]$^+$.

Preparation 59: 4-[2-(Tetrahydropyran-4-yl)-1-(thiazol-2-ylcarbamoyl)ethyl]benzenesulfonyl chloride

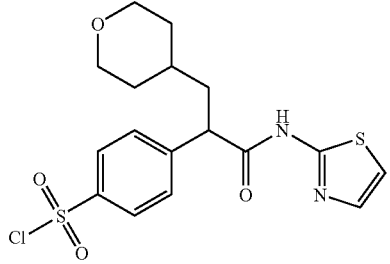

2-(4-Nitrophenyl)-3-(tetrahydropyran-4-yl)propionic acid (Preparation 46, 10.40 g, 37.2 mmol) was condensed with thiazol-2-ylamine employing the procedure described in EXAMPLE 65 to afford 2-(4-nitrophenyl)-3-(tetrahydropyran-4-yl)-N-thiazol-2-ylpropionamide: m/z (ES$^+$)=362.1 [M+H]$^+$. The nitro group of this compound (6.55 g, 18.1 mmol) was reduced utilising the procedure described in EXAMPLE 145 to give 2-(4-aminophenyl)-3-(tetrahydropyran-4-yl)-N-thiazol-2-ylpropionamide: m/z (ES$^+$)=332.1 [M+H]$^+$. A solution of NaNO$_2$ (2.11 g, 30.5 mmol) in H$_2$O (20 mL) was added slowly to a stirred mixture of the above aniline (9.40 g, 28.4 mmol), 12M HCl (30 mL), and H$_2$O (30 mL) at 0° C. After 1 h, the resulting diazonium salt solution was added over 15 min to a mixture of CuCl$_2$.2H$_2$O (1.29 g, 7.6 mmol) in AcOH (64.5 mL) and H$_2$O (3.2 mL) which had been saturated previously with SO$_2$. The mixture was stirred for 1.5 h, treated with H$_2$O (200 mL) and extracted with EtOAc (300+150 mL). The combined EtOAc extracts were washed with H$_2$O (2×200 mL), filtered, and dried (MgSO$_4$). Filtration and solvent evaporation provided the title compound: m/z (ES$^+$)=466.1 [M+MeCN+H]$^+$.

Preparation 60: 4-[1-(5-Chlorothiazol-2-ylcarbamoyl)-2-(tetrahydropyran-4-yl)ethyl]benzenesulfonyl chloride

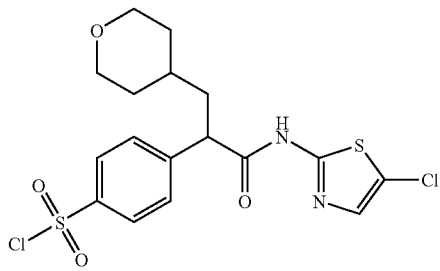

Using similar procedures to those described in Preparation 59, 2-(4-nitrophenyl)-3-(tetrahydropyran-4-yl)propionic acid (Preparation 46, 9.74 g, 34.9 mmol) was converted into the title compound: δ$_H$(CDCl$_3$): 1.25-1.50 (3H, m), 1.55-1.70 (2H, br), 1.80-1.85 (1H, m), 2.20-2.30 (1H, m), 3.20-3.35 (2H, m), 3.80-4.00 (3H, m), 7.20 (1H, s), 7.65 (2H, d), 8.00 (2H, d).

Preparation 61: 5-Fluorothiazol-2-ylamine hydrochloride

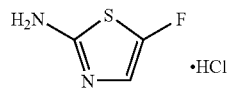

NEt$_3$ (63.4 mL, 455 mmol) was added to a stirred suspension of 5-bromothiazol-2-ylamine hydrobromide (102.7 g, 379 mmol) in CH$_2$Cl$_2$ (1.5 L). After 1 h, TFAA (64.2 mL, 455 mmol) was added dropwise at 0° C. over 15 min. The mixture was allowed to warm to 20° C. over 1 h, before being stirred for an additional 2 h. H$_2$O (600 mL) was added and the resulting precipitate was collected. The aqueous layer of the filtrate was separated and extracted with CHCl$_3$ (3×300 mL). The combined organic extracts were washed with brine, dried (Na$_2$SO$_4$), filtered and concentrated. The collected precipitate and residual solid were combined and triturated with EtOAc-n-C$_6$H$_{14}$ to give N-(5-bromothiazol-2-yl)-2,2,2-trifluoroacetamide: δ$_H$ (CDCl$_3$): 7.45 (1H, s), 13.05 (1H, br). n-BuLi (253 mL of a 1.58M solution in hexanes, 403 mmol) was added dropwise over 50 min to a stirred solution of the above amide (50.0 g, 183 mmol) in anhydrous THF (1.3 L) at −78° C. After 1.5 h, a solution of N-fluorobenzenesulphonimide (86.0 g, 275 mmol) in anhydrous THF (250 mL) was added dropwise over 30 min. The mixture was stirred for 3 h, before being warmed up to −30° C. H$_2$O (300 mL) was added and the mixture was filtered through a Celite pad. The solid collected and Celite were washed with Et$_2$O (400 mL) and H$_2$O (400 mL). The organic layer of the filtrate was separated and extracted with water (2×400 mL). The combined aqueous layers were washed with Et$_2$O (400 mL), before being acidified to pH 6.5 with 2M HCl and extracted with EtOAc (2×400 mL). The combined organic extracts were washed with H$_2$O (2×400 mL) and brine, before being dried (MgSO$_4$), filtered and concentrated. Column chromatography (EtOAc-n-C$_6$H$_{14}$, 1:3 to 1:2) gave N-(5-fluorothiazol-2-yl)-2,2,2-trifluoroacetamide: δ$_H$ (CDCl$_3$): 7.13 (1H, d). AcCl (12.6 mL, 175 mmol) was added dropwise to a stirred solution of this amide (15.7 g, 73 mmol) in MeOH (300 mL) at 0° C. The mixture was stirred at 20° C. for 30 min, heated under reflux for 1 h, and finally concentrated in vacuo. The residual solid was triturated with THF to give the title compound: δ$_H$(D$_2$O): 7.00 (1H, d).

Preparation 62: 4-[2-(Tetrahydropyran-4-yl)-1-(thiazol-2-ylcarbamoyl)ethyl]benzoic acid

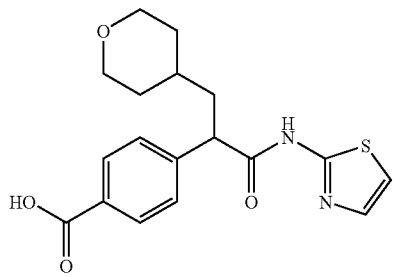

Methyl 4-tert-butoxycarbonylmethylbenzoate (1.71 g, 6.84 mmol) was alkylated with 4-iodomethyltetrahydropyran (1.86 g, 8.21 mmol), employing the method described in Preparation 41, to afford methyl 4-[1-tert-butoxycarbonyl-2-(tetrahydropyran-4-yl)ethyl]benzoate: $RT^4$=3.86 min. A solution of this compound (1.37 g, 3.94 mmol) in $CH_2Cl_2$ (5 mL) was treated with TFA-$CH_2Cl_2$ (2:1, 15 mL) at 0° C. over 10 min. The mixture was stirred at 20° C. for 3 h, before being concentrated in vacuo. The residue was treated with PhMe and the solvents were evaporated off under reduced pressure. This process was repeated twice to provide crude methyl 4-[1-carboxy-2-(tetrahydropyran-4-yl)ethyl]benzoate. This carboxylic acid was condensed with thiazol-2-ylamine, utilizing the protocol outlined in EXAMPLE 65, to furnish methyl 4-[2-(tetrahydropyran-4-yl)-1-(thiazol-2-ylcarbamoyl)ethyl]benzoate: m/z ($ES^+$)=375.2 [M+H]$^+$. This ester (1.20 g, 3.21 mmol) was saponified with LiOH.$H_2O$, using the procedure described in Preparation 22, to furnish the title compound: m/z ($ES^-$)=359.2 [M−H]$^-$.

Example 1

(E)-2-(4-Methanesulfonylphenyl)-N-thiazol-2-yl-3-thiophen-3-ylacrylamide

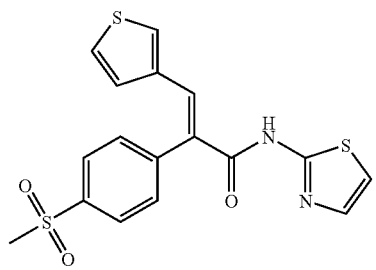

A suspension of PS-carbodiimide (688 mg, loading 1.34 µmol mg$^{-1}$, 922 µmol), (E)-2-(4-methanesulfonylphenyl)-3-thiophen-3-ylacrylic acid (Preparation 1, 139 mg, 450 µmol), and HOBt (84 mg, 622 µmol) in anhydrous DMF was stirred for 15 min at 20° C. Thiazol-2-ylamine (32 mg, 320 µmol) was added, then the mixture was stirred for 40 h at 20° C., before being filtered through Celite. The filter cake was washed with DMF (10 mL), EtOAc (20 mL), and $CH_2Cl_2$ (20 mL). The solutions were combined, the solvents removed under reduced pressure, and the residue dissolved in EtOAc (50 mL). The EtOAc solution was washed with saturated aqueous $Na_2CO_3$ (3×20 mL), $H_2O$ (20 mL), and brine (20 mL), before being dried ($Na_2SO_4$). Filtration, solvent evaporation, and flash chromatography (IH-EtOAc, 3:1 to 1:3) gave the title compound: $RT^4$=3.43 min; m/z ($ES^+$)=391.0 [M+H]$^+$.

The PS-carbodiimide-HOBt-mediated condensation of the appropriate carboxylic acid with thiazol-2-ylamine, as outlined in EXAMPLE 1, was also used to synthesise the amides listed in TABLE 6 below.

TABLE 6

| Ex | Structure | Name | RT(min) | m/z(ES$^+$) |
|---|---|---|---|---|
| 2 | 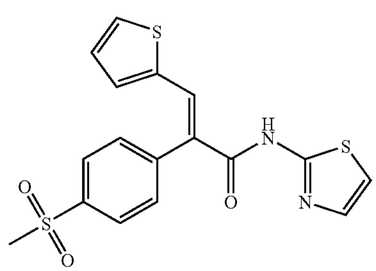 | (E)-2-(4-Methanesulfonyl-phenyl)-N-thiazol-2-yl-3-thiophen-2-ylacrylamide | 3.45[4] | 391.0 [M + H]$^+$ |

TABLE 6-continued

| Ex | Structure | Name | RT(min) | m/z(ES+) |
|---|---|---|---|---|
| 3 | 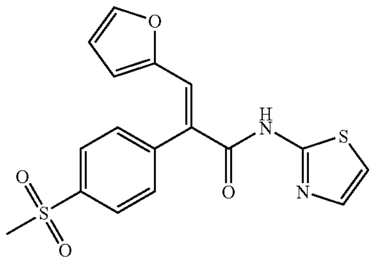 | (E)-3-Furan-2-yl-2-(4-methanesulfonylphenyl)-N-thiazol-2-ylacrylamide | 3.39[4] | 375.1 [M + H]+ |
| 4 | 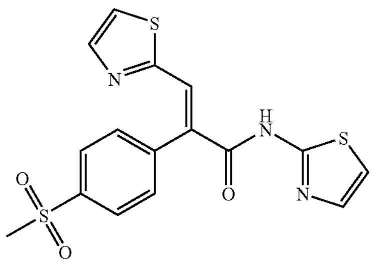 | (E)-2-(4-Methanesulfonyl-phenyl)-3,N-bisthiazol-2-ylacrylamide | 3.13[4] | 392.0 [M + H]+ |
| 5 | 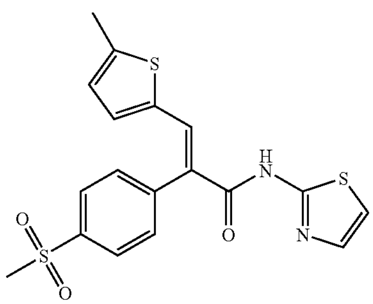 | (E)-2-(4-Methanesulfonyl-phenyl)-3-(5-methylthiophen-2-yl)-N-thiazol-2-ylacrylamide | 3.56[4] | 405.1 [M + H]+ |
| 6 | 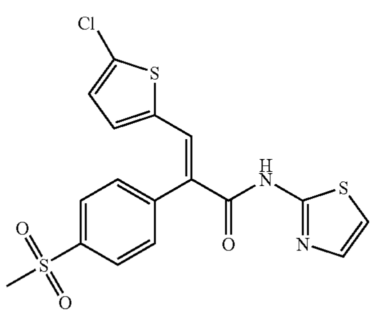 | (E)-3-(5-Chlorothiophen-2-yl)-2-(4-methanesulfonyl-phenyl)-N-thiazol-2-ylacrylamide | 3.63[4] | 466.1 [M + MeCN + H]+ |
| 7 | 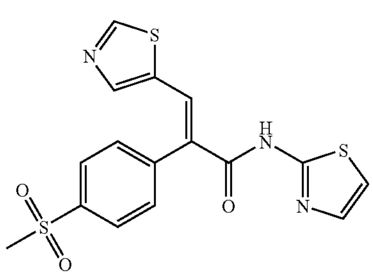 | (E)-2-(4-Methanesulfonyl-phenyl)-3-thiazol-5-yl-N-thiazol-2-ylacrylamide | 3.12[4] | 392.1 [M + H]+ |

TABLE 6-continued

| Ex | Structure | Name | RT(min) | m/z(ES+) |
|---|---|---|---|---|
| 8 | 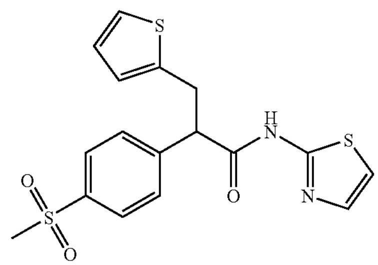 | 2-(4-Methanesulfonylphenyl)-N-thiazol-2-yl-3-thiophen-2-ylpropionamide | 3.41[A] | 434.1 [M + MeCN + H]+ |
| 9 | 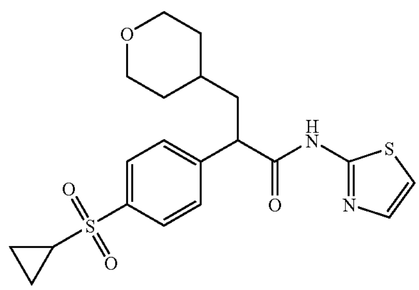 | 2-(4-Cyclopropanesulfonyl)-phenyl)-3-tetrahydropyran-4-yl)-N-thiazol-2-yl-propionamide | 3.19[A] | 421.2 [M + H]+ |
| 10 | 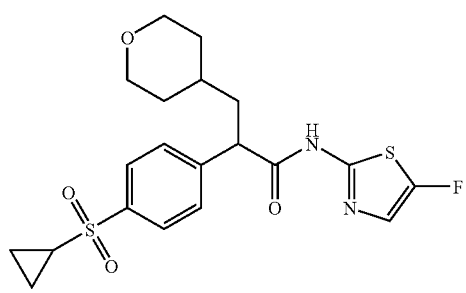 | 2-(4-Cyclopropanesulfonyl)-phenyl)-N-(5-fluorothiazol-2-yl)-3-(tetrahydropyran-4-yl)-propionamide | 1.50[B] | 439.0 [M + H]+ |
| 11 | 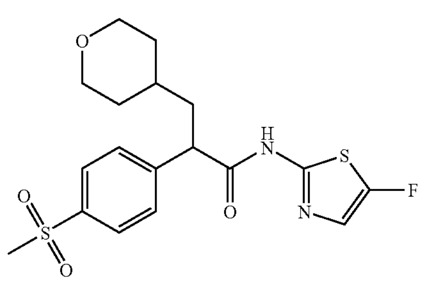 | N-(5-Fluorothiazol-2-yl)-2-(4-methanesulfonylphenyl)-3-(tetrahydropyran-4-yl)-propionamide | 3.20[A] | 454.2 [M + MeCN + H]+ |
| 12 | 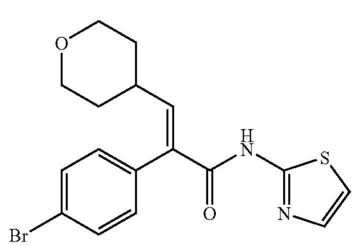 | (E)-2-(4-Bromophenyl)-3-(tetrahydropyran-4-yl)-N-thiazol-2-ylacrylamide | 3.67[A] | 393.0 [M + H]+ |

TABLE 6-continued

| Ex | Structure | Name | RT(min) | m/z(ES+) |
|---|---|---|---|---|
| 13 | 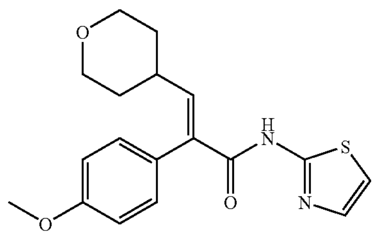 | (E)-2-(4-Methoxyphenyl)-3-(tetrahydropyran-4-yl)-N-thiazol-2-ylacrylamide | 3.52[4] | 345.2 [M + H]+ |
| 14 | 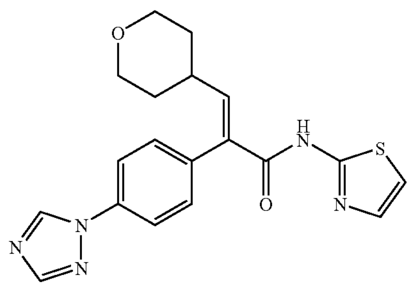 | (E)-3-(Tetrahydropyran-4-yl)-N-thiazol-2-yl-2-(4-[1,2,4]triazol-1-ylphenyl)-acrylamide | 3.17[4] | 382.1 [M + H]+ |
| 15 | 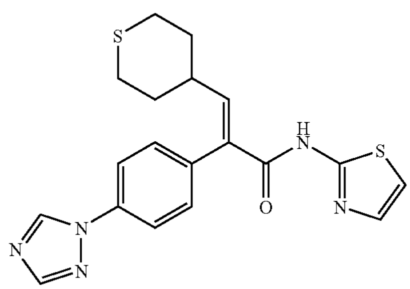 | (E)-3-(Tetrahydrothiopyran-4-yl)-N-thiazol-2-yl-2-(4-[1,2,4]triazol-1-ylphenyl)-acrylamide | 3.45[4] | 398.1 [M + H]+ |
| 16 | 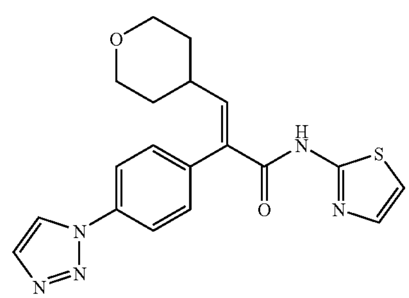 | (E)-3-(Tetrahydropyran-4-yl)-N-thiazol-2-yl-2-(4-[1,2,3]triazol-1-ylphenyl)-acrylamide | 3.17[4] | 382.0 [M + H]+ |
| 17 | 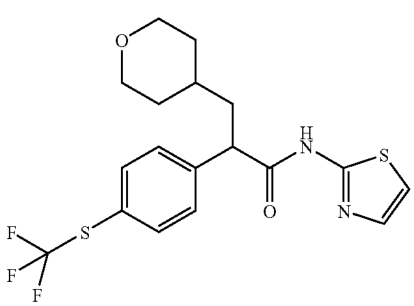 | 3-(Tetrahydropyran-4-yl)-N-thiazol-2-yl-2-(4-trifluoromethylsulfanyl-phenyl)propionamide | 3.83[4] | 417.2 [M + H]+ |

TABLE 6-continued

| Ex | Structure | Name | RT(min) | m/z(ES+) |
|---|---|---|---|---|
| 18 | 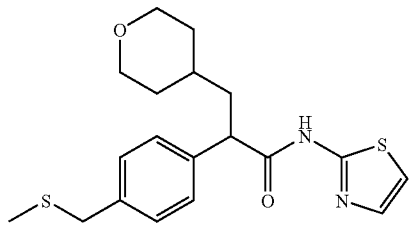 | 2-(4-Methylsulfanylmethyl-phenyl)-3-(tetrahydropyran-4-yl)-N-thiazol-2-ylpropionamide | 3.47[4] | 377.1 [M + H]+ |
| 19 | 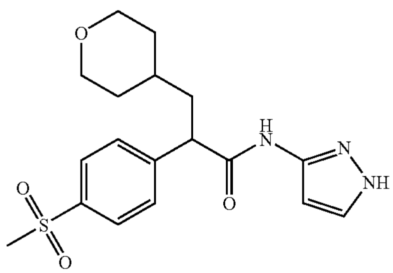 | 2-(4-Methanesulfonylphenyl)-N-(1H-pyrazol-3-yl)-3-(tetrahydropyran-4-yl)propionamide | 2.90[4] | 378.1 [M + H]+ |
| 20 | 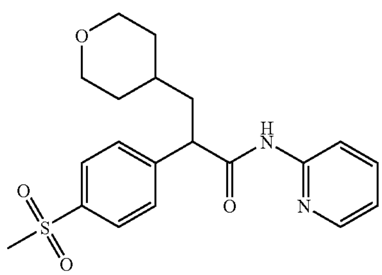 | 2-(4-Methanesulfonylphenyl)-N-pyridin-2-yl-3-(tetrahydro-pyran-4-yl)propionamide | 2.86[4] | 389.2 [M + H]+ |
| 21 | 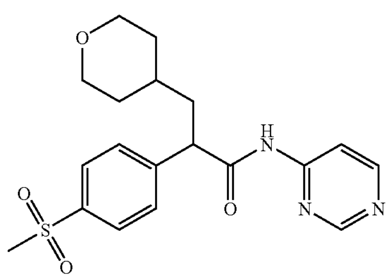 | 2-(4-Methanesulfonylphenyl)-N-pyrimidin-4-yl-3-(tetrahydropyran-4-yl)propionamide | 2.89[4] | 390.2 [M + H]+ |
| 22 | 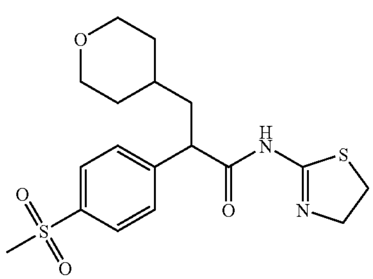 | N-(4,5-Dihydrothiazol-2-yl)-2-(4-methanesulfonylphenyl)-3-(tetrahydropyran-4-yl)propionamide | 2.61[4] | 397.2 [M + H]+ |

TABLE 6-continued

| Ex | Structure | Name | RT(min) | m/z(ES+) |
|---|---|---|---|---|
| 23 | 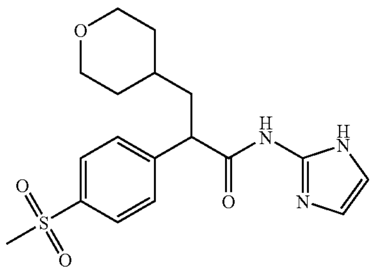 | N-(1H-Imidazol-2-yl)-2-(4-methanesulfonylphenyl)-3-(tetrahydropyran-4-yl)propionamide | 2.11[A] | 378.2 [M + H]+ |
| 24 | 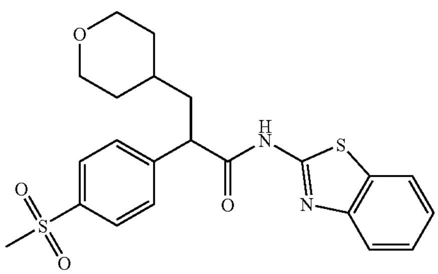 | N-Benzothiazol-2-yl-2-(4-methanesulfonylphenyl)-3-(tetrahydropyran-4-yl)propionamide | 3.44[A] | 445.3 [M + H]+ |
| 25 | 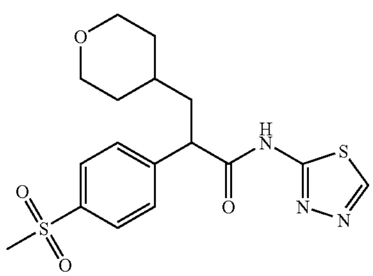 | 2-(4-Methanesulfonylphenyl)-3-(tetrahydropyran-4-yl)-N-[1,3,4]thiadiazol-2-ylpropionamide | 2.86[A] | 437.3 [M + MeCN + H]+ |
| 26 | 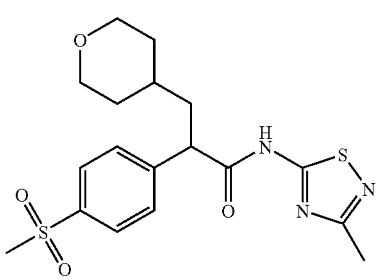 | 2-(4-Methanesulfonylphenyl)-N-(3-methyl-[1,2,4]thiadiazol-5-yl)-3-(tetrahydropyran-4-yl)propionamide | 3.01[A] | 410.3 [M + H]+ |
| 27 | 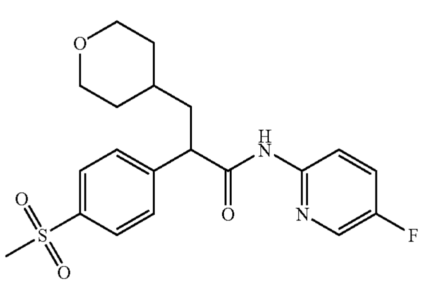 | N-(5-Fluoropyridin-2-yl)-2-(4-methanesulfonylphenyl)-3-(tetrahydropyran-4-yl)propionamide | 3.19[A] | 407.2 [M + H]+ |

TABLE 6-continued

| Ex | Structure | Name | RT(min) | m/z(ES+) |
|---|---|---|---|---|
| 28 | 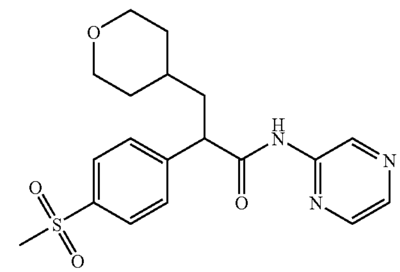 | 2-(4-Methanesulfonylphenyl)-N-pyrazin-2-yl-3-(tetrahydro-pyran-4-yl)propionamide | 2.87[A] | 390.3 [M + H]+ |
| 29 | 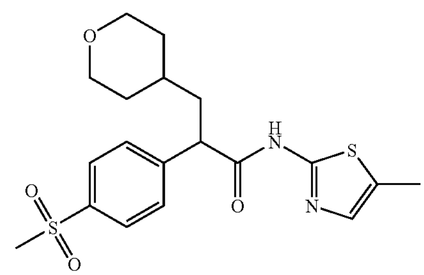 | 2-(4-Methanesulfonylphenyl)-N-(5-methylthiazol-2-yl)-3-(tetrahydropyran-4-yl)propionamide | 3.20[A] | 409.1 [M + H]+ |
| 30 | 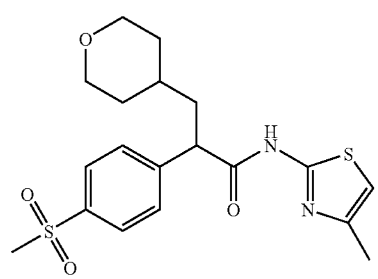 | 2-(4-Methanesulfonylphenyl)-N-(4-methylthiazol-2-yl)-3-(tetrahydropyran-4-yl)propionamide | 3.15[A] | 409.1 [M + H]+ |
| 31 | 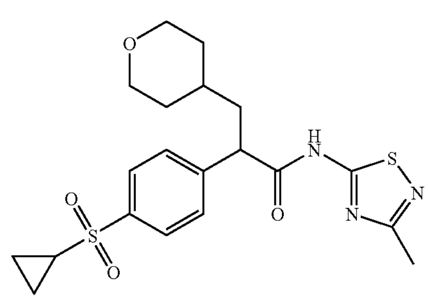 | 2-(4-Cyclopropanesulfonyl-phenyl)-N-(3-methyl-[1,2,4]thiadiazol-5-yl)-3-(tetrahydropyran-4-yl)propionamide | 3.19[A] | 436.3 [M + H]+ |
| 32 | 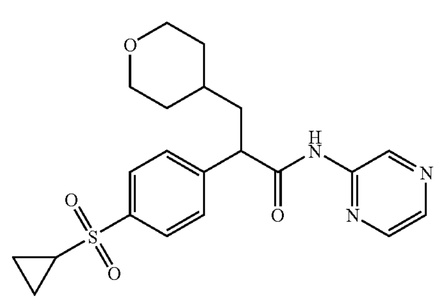 | 2-(4-Cyclopropanesulfonyl-phenyl)-N-pyrazin-2-yl-3-(tetrahydropyran-4-yl)propionamide | 3.06[A] | 416.3 [M + H]+ |

TABLE 6-continued

| Ex | Structure | Name | RT(min) | m/z(ES+) |
|---|---|---|---|---|
| 33 | 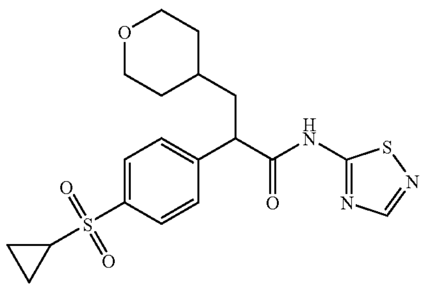 | 2-(4-Cyclopropanesulfonyl-phenyl)-3-(tetrahydropyran-4-yl)-N-[1,2,4]thiadiazol-5-ylpropionamide | 3.20[A] | 422.1 [M + H]+ |
| 34 | 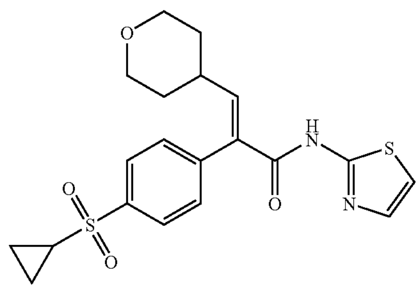 | (E)-2-(4-Cyclopropane-sulfonylphenyl)-3-(tetrahydropyran-4-yl)-N-thiazol-2-ylacrylamide | 3.14[A] | 460.2 [M + MeCN + H]+ |
| 35 | 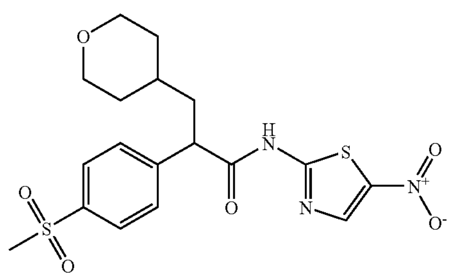 | 2-(4-Methanesulfonyl-phenyl)-N-(5-nitrothiazol-2-yl)-3-(tetrahydropyran-4-yl)propionamide | 3.36[A] | 481.3 [M + MeCN + H]+ |

[A]RT employing Method A.
[B]RT employing Method B.

Example 36

(E)-N-(5-Chlorothiazol-2-yl)-2-(4-methanesulfonylphenyl)-3-thiophen-2-ylacrylamide

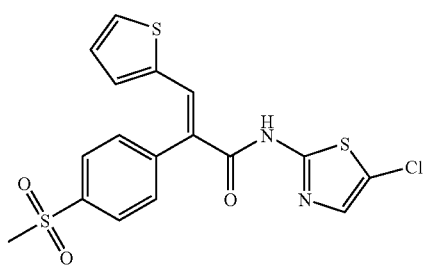

A solution of (E)-2-(4-methanesulfonylphenyl)-3-thiophen-2-ylacrylic acid (Preparation 2, 309 mg, 1.0 mmol), HATU (813 mg, 2.1 mmol), 5-chlorothiazol-2-ylamine hydrochloride (258 mg, 1.5 mmol), and DIPEA (0.71 mL, 4.0 mmol) in anhydrous DMF (5 mL) was heated under microwave irradiation with stirring at 60° C. for 2 min. The solvents were evaporated off under reduced pressure, then the remainder was partitioned between $CH_2Cl_2$ (60 mL) and 1M HCl (60 mL). The organic layer was separated and washed with 1M HCl (60 mL), $H_2O$ (60 mL), saturated aqueous $Na_2CO_3$ (2×60 mL), $H_2O$ (60 mL), and brine (60 mL), before being dried ($Na_2SO_4$). Filtration, solvent evaporation, and flash chromatography (IH-EtOAc, 4:1 to 2:3) gave the title compound: RT[A]=3.77 min; m/z (ES+)=466.1 [M+MeCN+H]+.

The microwave-mediated condensation of the appropriate carboxylic acid with thiazol-2-ylamines, outlined in EXAMPLE 36, was also employed to prepare the amides listed in TABLE 7 below.

TABLE 7

| Ex | Structure | Name | RT[4](min) | m/z(ES[+]) |
|---|---|---|---|---|
| 37 | 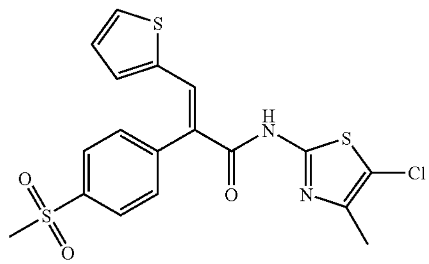 | (E)-N-(5-Chloro-4-methylthiazol-2-yl)-2-(4-methanesulfonylphenyl)-3-thiophen-2-ylacrylamide | 3.93 | 480.1 [M + MeCN + H][+] |
| 38 | 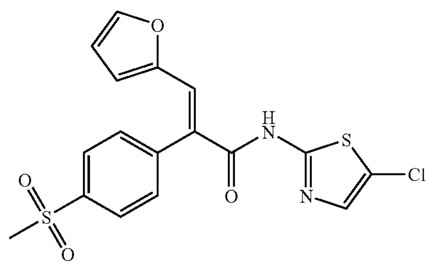 | (E)-N-(5-Chlorothiazol-2-yl)-3-furan-2-yl-2-(4-methanesulfonylphenyl)acrylamide | 3.78 | 450.1 [M + MeCN + H][+] |
| 39 | 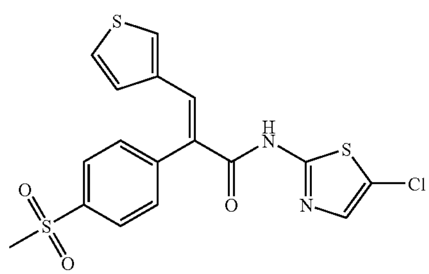 | (E)-N-(5-Chlorothiazol-2-yl)-2-(4-methanesulfonylphenyl)-3-thiophen-3-ylacrylamide | 3.77 | 466.1 [M + MeCN + H][+] |
| 40 | 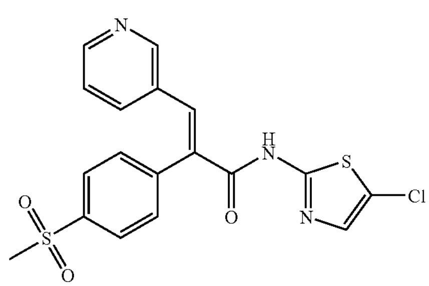 | (E)-N-(5-Chlorothiazol-2-yl)-2-(4-methanesulfonylphenyl)-3-pyridin-3-ylacrylamide | 3.27 | 461.2 [M + MeCN + H][+] |
| 41 | 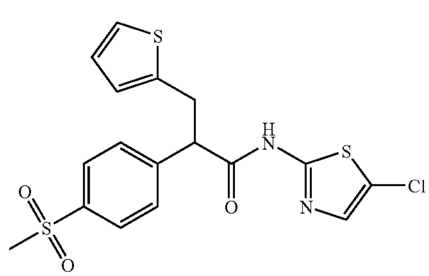 | N-(5-Chlorothiazol-2-yl)-2-(4-methanesulfonylphenyl)-3-thiophen-2-ylpropionamide | 3.75 | 468.1 [M + MeCN + H][+] |

TABLE 7-continued

| Ex | Structure | Name | RT⁴(min) | m/z(ES⁺) |
|---|---|---|---|---|
| 42 | 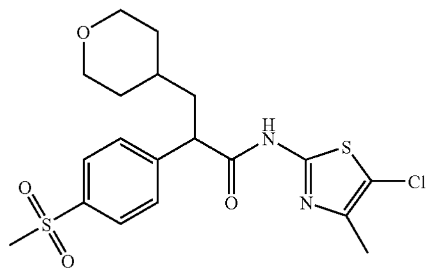 | N-(5-Chloro-4-methylthiazol-2-yl)-2-(4-methanesulfonylphenyl)-3-(tetrahydropyran-4-yl)propionamide | 3.66 | 484.1 [M + MeCN + H]⁺ |
| 43 | 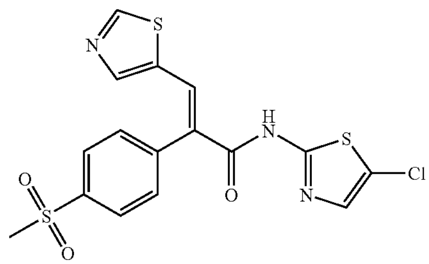 | (E)-N-(5-Chlorothiazol-2-yl)-2-(4-methanesulfonylphenyl)-3-thiazol-5-ylacrylamide | 3.55 | 467.1 [M + MeCN + H]⁺ |

Example 44

(E)-2-(4-Bromophenyl)-N-(5-chlorothiazol-2-yl)-3-furan-2-ylacrylamide

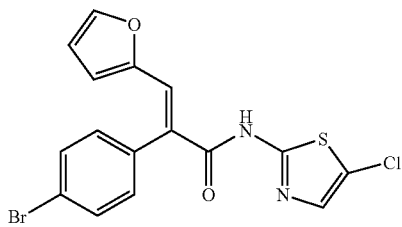

A suspension of (E)-2-(4-bromophenyl)-3-furan-2-ylacrylic acid (Preparation 9, 4.10 g, 14.0 mmol) and oxalyl chloride (2.5 mL, 28.0 mmol) in anhydrous $CH_2Cl_2$ (100 mL) was treated with a catalytic amount of anhydrous DMF (25 μL). The resulting solution was stirred at 20° C. for 4 h, then the solvents were removed under reduced pressure. $CH_2Cl_2$ (50 mL) was added to the residue, then the solvents were evaporated off under reduced pressure to give 2-(4-bromophenyl)-3-furan-2-ylacryloyl chloride as a brown solid. A solution of this acid chloride (343 mg, 1.1 mmol) in anhydrous THF (1 mL) was added to a solution of 5-chlorothiazol-2-ylamine hydrochloride (171 g, 1.0 mmol) and $NEt_3$ (0.56 mL, 4.0 mmol) in anhydrous THF (1 mL). The suspension was stirred for 16 h at 20° C., then the solvents were removed under reduced pressure. The residue was partitioned between $CH_2Cl_2$ (10 mL) and saturated aqueous $NaHCO_3$ (5 mL). The organic layer was washed with $H_2O$ (5 mL) and brine (5 mL), before being concentrated. The resulting solid was recrystallised from MeOH to furnish the title compound: $RT^4$=4.39 min; m/z (ES⁺)=410.9 [M+H]⁺.

Several other enamides were prepared via the condensation of the appropriate acid chloride with heteroaromatic amines as represented by EXAMPLE 44. These compounds are listed in TABLE 8 below:

TABLE 8

| Ex | Structure | Name | RT⁴(min) | m/z(ES⁺) |
|---|---|---|---|---|
| 45 | 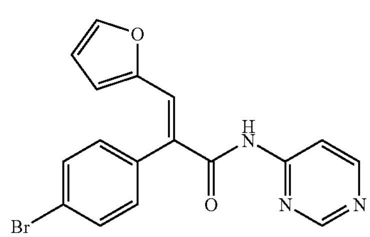 | (E)-2-(4-Bromophenyl)-3-furan-2-yl-N-pyrimidin-4-ylacrylamide | 4.01 | 369.9 [M + H]⁺ |

TABLE 8-continued

| Ex | Structure | Name | RT[4](min) | m/z(ES[+]) |
|---|---|---|---|---|
| 46 | 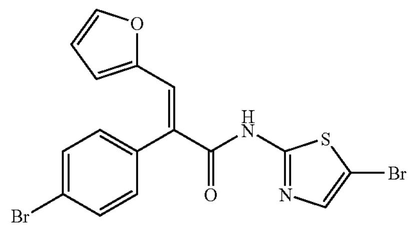 | (E)-2-(4-Bromophenyl)-N-(5-bromothiazol-2-yl)-3-furan-2-ylacrylamide | 4.41 | 454.9 [M + H][+] |
| 47 | 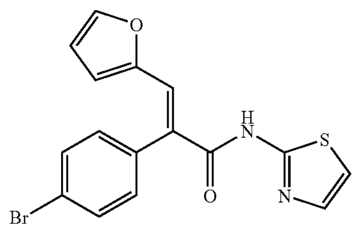 | (E)-2-(4-Bromophenyl)-3-furan-2-yl-N-thiazol-2-ylacrylamide | 4.09 | 377.0 [M + H][+] |
| 48 | 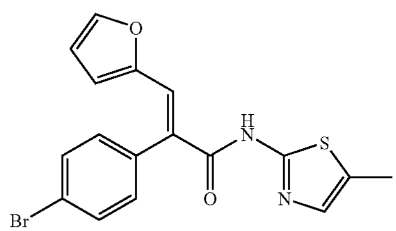 | (E)-2-(4-Bromophenyl)-3-furan-2-yl-N-(5-methylthiazol-2-yl)acrylamide | 4.20 | 389.0 [M + H][+] |
| 49 | 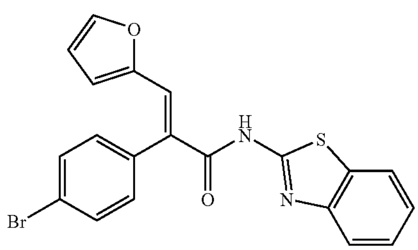 | (E)-N-(Benzothiazol-2-yl-2-(4-bromophenyl)-3-furan-2-ylacrylamide | 4.44 | 427.0 [M + H][+] |
| 50 | 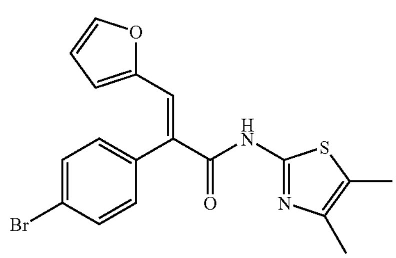 | (E)-2-(4-Bromophenyl)-N-(4,5-dimethylthiazol-2-yl)-3-furan-2-ylacrylamide | 4.32 | 403.0 [M + H][+] |
| 51 | 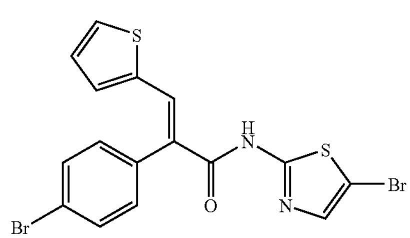 | (E)-2-(4-Bromophenyl)-N-(5-bromothiazol-2-yl)-3-thiophen-2-ylacrylamide | 4.55 | 470.9 [M + H][+] |

TABLE 8-continued

| Ex | Structure | Name | RT[4](min) | m/z(ES[+]) |
|---|---|---|---|---|
| 52 | 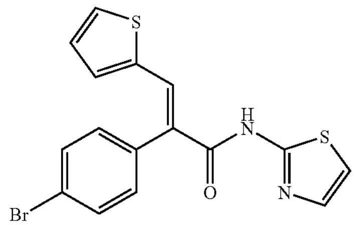 | (E)-2-(4-Bromophenyl)-N-thiazol-2-yl-3-thiophen-2-ylacrylamide | 4.15 | 393.0 [M + H][+] |
| 53 | 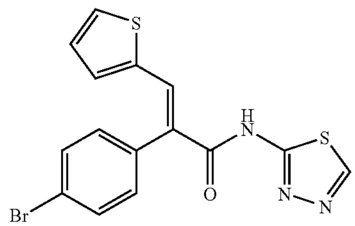 | (E)-2-(4-Bromophenyl)-N-[1,3,4]thiadiazol-2-yl-3-thiophen-2-ylacrylamide | 3.94 | 393.9 [M + H][+] |
| 54 | 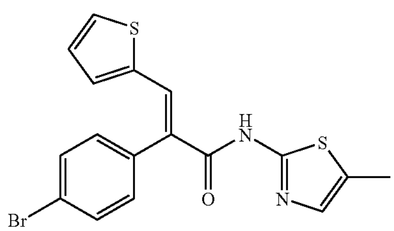 | (E)-2-(4-Bromophenyl)-N-(5-methylthiazol-2-yl)-3-thiophen-2-ylacrylamide | 4.31 | 407.0 [M + H][+] |
| 55 | 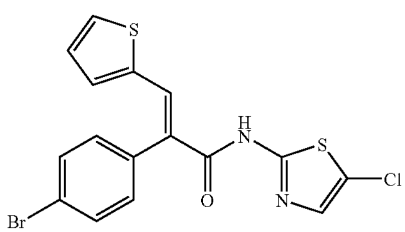 | (E)-2-(4-Bromophenyl)-N-(5-chlorothiazol-2-yl)-3-thiophen-2-ylacrylamide | 4.48 | 426.9 [M + H][+] |
| 56 | 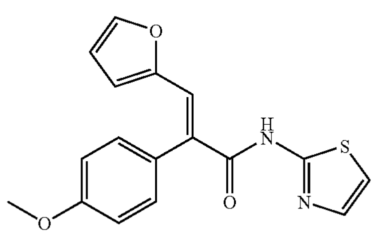 | (E)-3-Furan-2-yl-2-(4-methyoxyphenyl)-N-thiazol-2-ylacrylamide | 3.90 | 327.0 [M + H][+] |
| 57 | 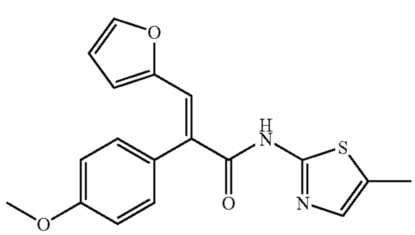 | (E)-3-Furan-2-yl-2-(4-methyoxyphenyl)-N-(5-methylthiazol-2-yl)acrylamide | 4.06 | 341.0 [M + H][+] |

TABLE 8-continued

| Ex | Structure | Name | RT[4](min) | m/z(ES[+]) |
| --- | --- | --- | --- | --- |
| 58 | 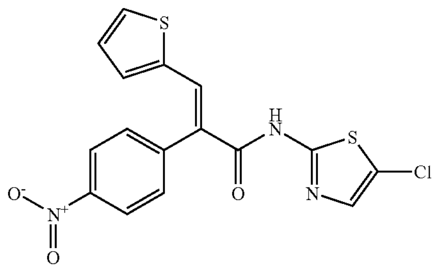 | (E)-N-(5-Chlorothiazol-2-yl)-2-(4-nitrophenyl)-3-thiophen-2-ylacrylamide | 4.03 | 392.1 [M + H][+] |
| 59 | 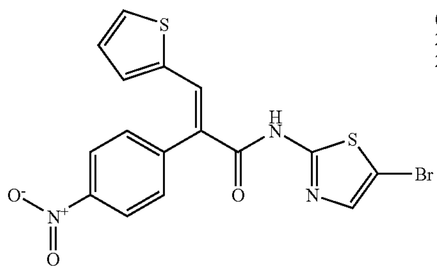 | (E)-N-(5-Bromothiazol-2-yl)-2-(4-nitrophenyl)-3-thiophen-2-ylacrylamide | 4.03 | 438.0 [M + H][+] |
| 60 | 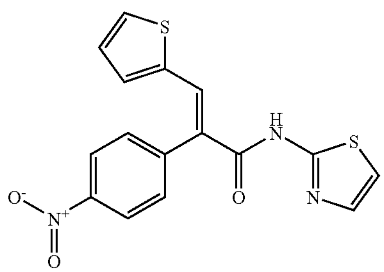 | (E)-2-(4-Nitrophenyl)-N-thiazol-2-yl)-3-thiophen-2-ylacrylamide | 3.74 | 358.1 [M + H][+] |
| 61 | 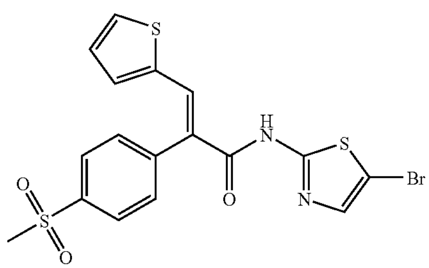 | (E)-N-(5-Bromothiazol-2-yl)-2-(4-methanesulfonylphenyl)-3-thiophen-2-ylacrylamide | 3.80 | 510.1 [M + MeCN + H][+] |
| 62 | 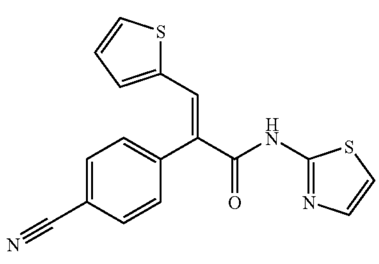 | (E)-2-(4-Cyanophenyl)-N-thiazol-2-yl-3-thiophen-2-ylacrylamide | 3.61 | 338.1 [M + H][+] |
| 63 | 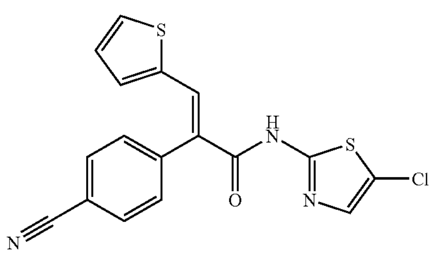 | (E)-N-(5-Chlorothiazol-2-yl)-2-(4-cyanophenyl)-3-thiophen-2-ylacrylamide | 3.96 | 372.0 [M + H][+] |

TABLE 8-continued

| Ex | Structure | Name | RT[4](min) | m/z(ES+) |
|---|---|---|---|---|
| 64 | 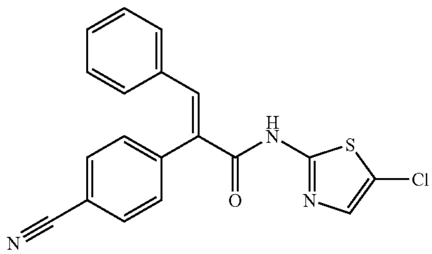 | (E)-N-(5-Chlorothiazol-2-yl)-2-(4-cyanophenyl)-3-phenylacrylamide | 4.25 | 366.0 [M + H]+ |

Example 65

2-(4-Methanesulfonylphenyl)-3-(tetrahydropyran-4-yl)-N-thiazol-2-ylpropionamide

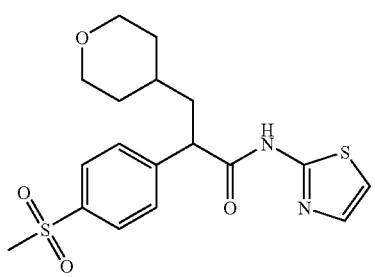

EDCI (80 mg, 420 µmol) and HOBt (56 mg, 420 µmol) were added to a stirred solution of 2-(4-methanesulfonylphenyl)-3-(tetrahydropyran-4-yl)propionic acid (Preparation 41, 100 mg, 320 µmol) in anhydrous DMF (6 mL). After 15 min, the solution was treated with thiazol-2-ylamine (38 mg, 380 µmol). The mixture was stirred at 20° C. for 16 h, before being concentrated under reduced pressure. The residue was partitioned between $CH_2Cl_2$ and saturated aqueous $Na_2CO_3$. The organic layer was washed with 1M HCl and dried ($MgSO_4$). Filtration and solvent evaporation yielded the title compound: RT[4]=3.16 min; m/z (ES+)=436.2 [M+MeCN+H]+.

The procedure exemplified by the preparation of EXAMPLE 65 was also used to prepare several other amides (TABLE 9).

TABLE 9

| Ex | Structure | Name | RT(min) | m/z(ES+) |
|---|---|---|---|---|
| 66 | 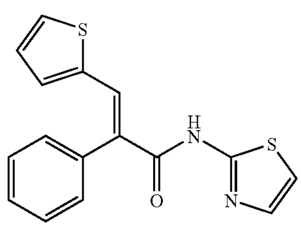 | (E)-2-Phenyl-N-thiazol-2-yl-3-thiophen-2-ylacrylamide | 3.91[4] | 313.0 [M + H]+ |
| 67 | 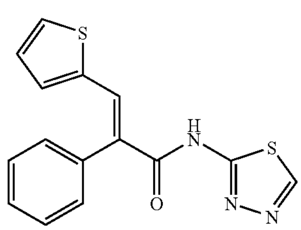 | (E)-2-Phenyl-N-[1,3,4]thiadiazol-2-yl-3-thiophen-2-ylacrylamide | 3.77[4] | 314.1 [M + H]+ |

TABLE 9-continued

| Ex | Structure | Name | RT(min) | m/z(ES+) |
|---|---|---|---|---|
| 68 | 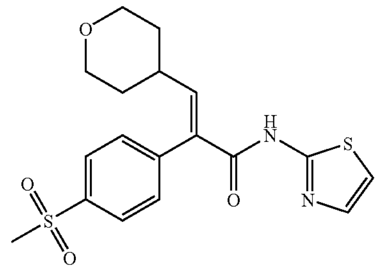 | (E)-2-(4-Methanesulfonyl-phenyl)-3-(tetrahydropyran-4-yl)-N-thiazol-2-ylacrylamide | 3.18[4] | 393.2 [M + H]+ |
| 69 | 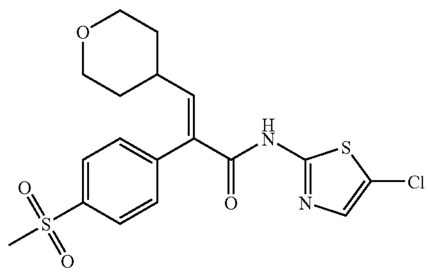 | (E)-N-(5-Chlorothiazol-2-yl)-2-(4-methanesulfonylphenyl)-2-(tetrahydropyran-4-yl)-acrylamide | 3.53[4] | 468.2 [M + MeCN + H]+ |
| 70 | 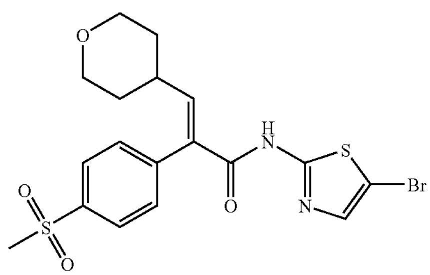 | (E)-N-(5-Bromothiazol-2-yl)-2-(4-methanesulfonylphenyl)-3-(tetrahydropyran-4-yl)-acrylamide | 3.55[4] | 514.1 [M + MeCN + H]+ |
| 71 | 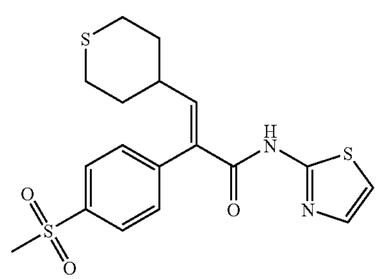 | (E)-2-(4-Methanesulfonyl-phenyl)-3-(tetrahydrothio-pyran-4-yl)-N-thiazol-2-yl-acrylamide | 3.53[4] | 450.1 [M + MeCN + H]+ |
| 72 | 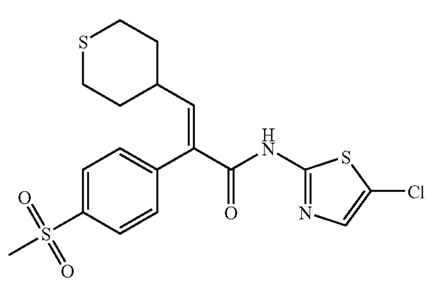 | (E)-N-(5-Chlorothiazol-2-yl)-2-(4-methanesulfonylphenyl)-3-(tetrahydrothiopyran-4-yl)-acrylamide | 3.91[4] | 484.0 [M + MeCN + H]+ |

TABLE 9-continued

| Ex | Structure | Name | RT(min) | m/z(ES+) |
|---|---|---|---|---|
| 73 | 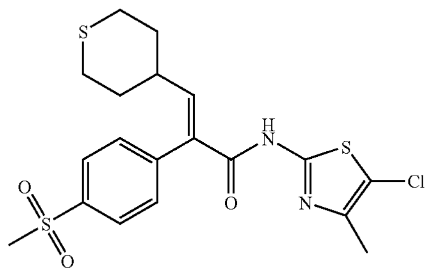 | (E)-N-(5-Chloro-4-methyl-thiazol-2-yl)-2-(4-methane-sulfonylphenyl)-3-(tetrahydro-thiopyran-4-yl)acrylamide | 3.95[4] | 498.2 [M + MeCN + H]+ |
| 74 | 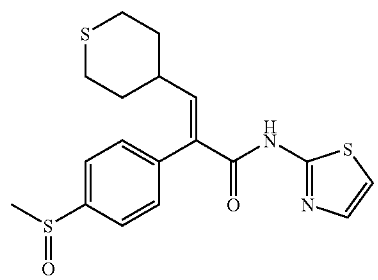 | (E)-2-(4-Methanesulfinyl-phenyl)-3-(tetrahydro-thiopyran-4-yl)-N-thiazol-2-ylacrylamide | 3.35[4] | 393.1 [M + H]+ |
| 75 | 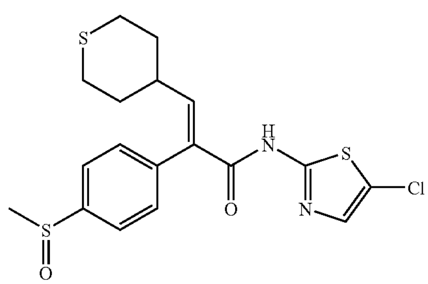 | (E)-N-(5-Chlorothiazol-2-yl)-2-(4-methanesulfinylphenyl)-3-(tetrahydrothiopyran-4-yl)-acrylamide | 3.71[4] | 468.2 [M + MeCN + H]+ |
| 76 | 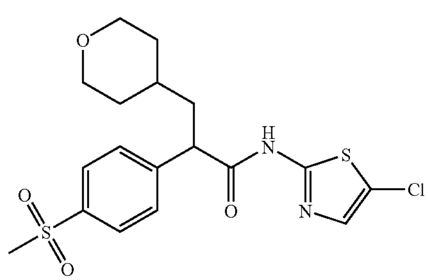 | N-(5-Chlorothiazol-2-yl)-2-(4-methanesulfonylphenyl)-3-(tetrahydropyran-4-yl)-propionamide | 3.57[4] | 470.3 [M + MeCN + H]+ |
| 77 | 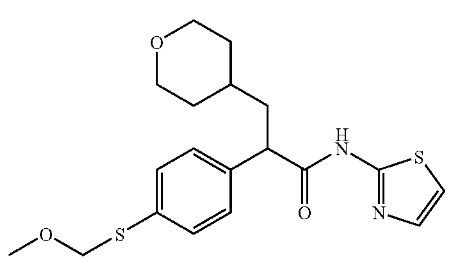 | 2-(4-Methoxymethylsulfanyl-phenyl)-3-(tetrahydropyran-4-yl)-N-thiazol-2-yl-propionamide | 3.51[4] | 393.2 [M + H]+ |

TABLE 9-continued

| Ex | Structure | Name | RT(min) | m/z(ES+) |
|---|---|---|---|---|
| 78 | 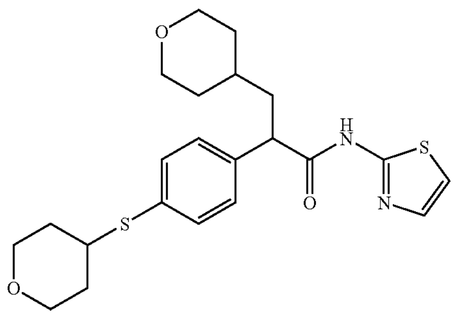 | 2-(Tetrahydropyran-4-yl)-2-[4-(tetrahydropyran-4-ylsulfanyl)phenyl]-N-thiazol-2-ylpropionamide | 3.40[4] | 433.1 [M + H]+ |
| 79 | 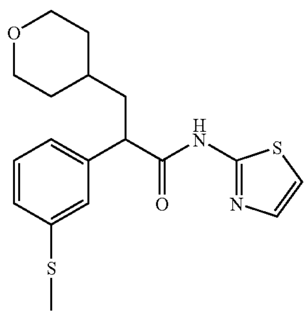 | 2-(3-Methylsulfanylphenyl)-3-(tetrahydropyran-4-yl)-N-thiazol-2-ylpropionamide | 3.52[4] | 363.2 [M + H]+ |
| 80 | 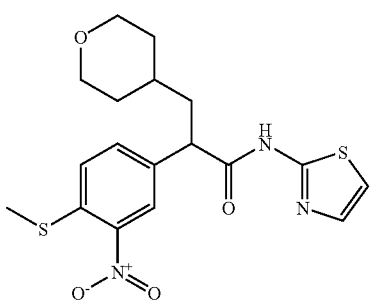 | 2-(4-Methylsulfanyl-3-nitrophenyl)-3-(tetrahydropyran-4-yl)-N-thiazol-2-yl-propionamide | 3.42[4] | 408.1 [M + H]+ |
| 81 | 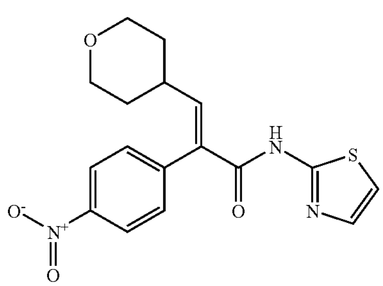 | (E)-2-(4-Nitrophenyl)-3-(tetrahydropyran-4-yl)-N-thiazol-2-ylacrylamide | 1.51[B] | 360.0 [M + H]+ |
| 82 | 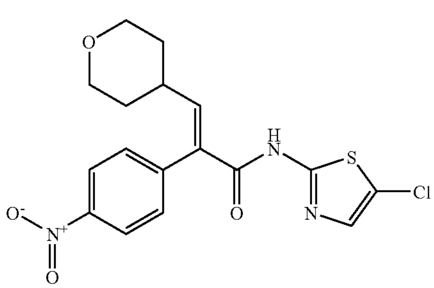 | (E)-N-(5-Chlorothiazol-2-yl)-2-(4-nitrophenyl)-3-(tetrahydropyran-4-yl)-acrylamide | 1.74[B] | 394.0 [M + H]+ |

TABLE 9-continued

| Ex | Structure | Name | RT(min) | m/z(ES+) |
|---|---|---|---|---|
| 83 | 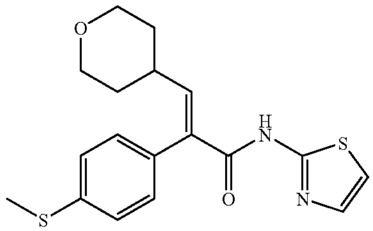 | (E)-2-(4-Methylsulfanyl-phenyl)-3-(tetrahydropyran-4-yl)-N-thiazol-2-ylacrylamide | 1.61[B] | 361.0 [M + H]+ |
| 84 | 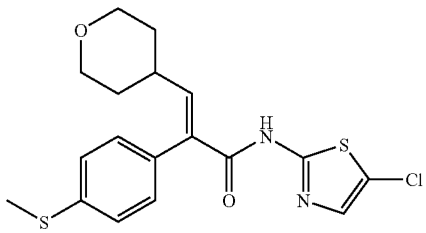 | (E)-N-(5-Chlorothiazol-2-yl)-2-(4-methylsulfanylphenyl)-3-(tetrahydropyran-4-yl)acrylamide | 1.86[B] | 395.0 [M + H]+ |
| 85 | 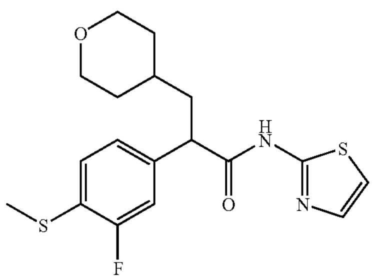 | 2-(3-Fluoro-4-methylsulfanyl-phenyl)-3-(tetrahydropyran-4-yl)-N-thiazol-2-ylpropionamide | 3.52[A] | 381.2 [M + H]+ |
| 86 | 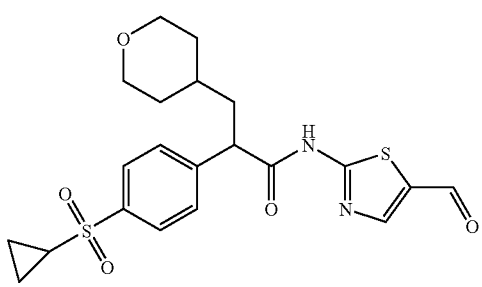 | 2-(4-Cyclopropanesulfonyl-phenyl)-N-(5-formylthiazol-2-yl)-3-(tetrahydropyran-4-yl)propionamide | 3.22[A] | 490.2 [M + MeCN + H]+ |
| 87 | 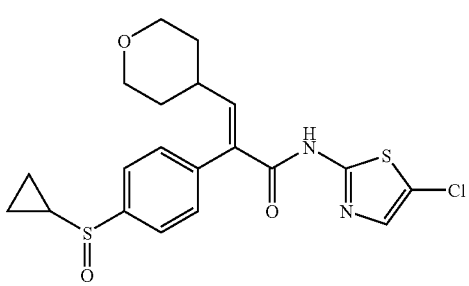 | (E)-N-(5-Chlorothiazol-2-yl)-2-(4-cyclopropanesulfinyl-phenyl)-3-(tetrahydropyran-4-yl)acrylamide | 3.39[A] | 437.2 [M + H]+ |

TABLE 9-continued

| Ex | Structure | Name | RT(min) | m/z(ES+) |
|---|---|---|---|---|
| 88 | 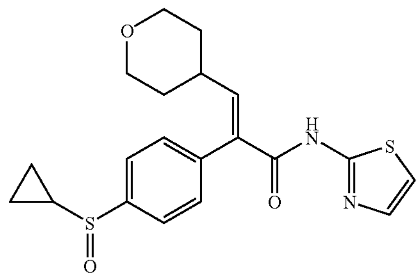 | (E)-2-(4-Cyclopropane-sulfinylphenyl)-3-(tetrahydro-pyran-4-yl)-N-thiazol-2-ylacrylamide | 2.89[A] | 403.3 [M + H]+ |
| 89 | 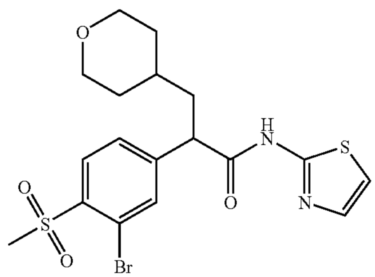 | 2-(3-Bromo-4-methanesulfonylphenyl)-3-(tetrahydropyran-4-yl)-N-thiazol-2-ylpropionamide | 3.39[A] | 516.2 [M + MeCN + H]+ |
| 90 | 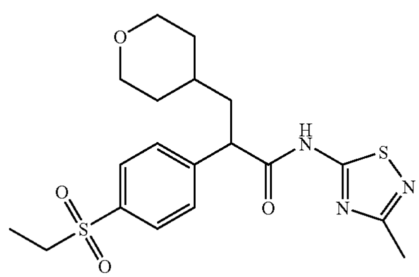 | 2-(4-Ethanesulfonylphenyl)-N-(3-methyl-[1,2,4]thiadiazol-5-yl)-3-(tetrahydropyran-4-yl)propionamide | 3.27[A] | 424.1 [M + H]+ |
| 91 | 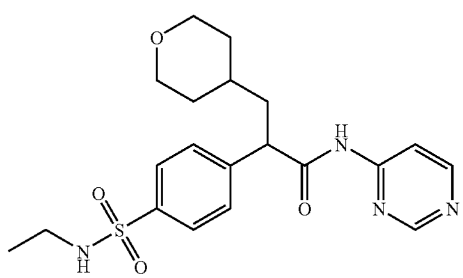 | 2-(4-Ethylsulfamoylphenyl)-N-pyrimidin-4-yl-3-(tetrahydropyran-4-yl)propionamide | 3.12[A] | 419.1 [M + H]+ |
| 92 | 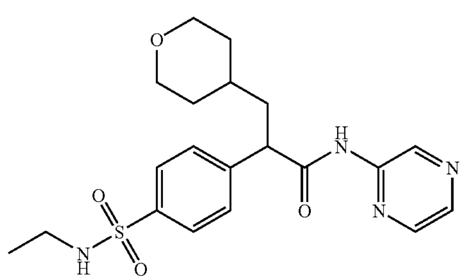 | 2-(4-Ethylsulfamoylphenyl)-N-pyrazin-2-yl-3-(tetrahydropyran-4-yl)propionamide | 3.11[A] | 419.2 [M + H]+ |

[A]RT employing Method A.
[B]RT employing Method B.

Example 93

(2R)-3-(Tetrahydropyran-4-yl)-2-(4-methanesulfonylphenyl)-N-thiazol-2-ylpropionamide

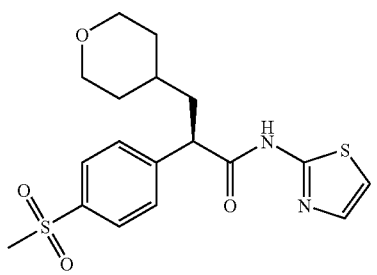

Method A: To a stirred solution of PPh$_3$ (3.53 g, 13.4 mmol) in CH$_2$Cl$_2$ (70 mL) was added NBS (882 mg, 10.6 mmol) at 0° C. After 10 min, (2R)-2-(4-methanesulfonylphenyl)-3-(tetrahydropyran-4-yl)propionic acid (Preparation 53, 2.80 g, 9.0 mmol) was added, then the mixture was stirred at 0° C. for 20 min, and then at 20° C. for 30 min. Thiazol-2-ylamine (933 mg, 9.3 mmol) and pyridine (2.2 mL, 18.8 mmol) were added at 0° C., then the mixture was stirred at 20° C. for 20 h. After solvent evaporation, the residue was partitioned between 5% aqueous citric acid (100 mL) and EtOAc (500 mL). The aqueous layer was further extracted with EtOAc (200 mL), then the combined organic layers were washed with H$_2$O and brine, before being dried (Na$_2$SO$_4$), filtered, and concentrated in vacuo. Chromatographic purification (CHCl$_3$-MeOH, 99:1) of the residue on Chromatorex® NH-DM1020 (Fuji Silysia Chemical, Ltd., Aichi-ken, Japan; See also http://www.fuji-silysia.co.jp/e-fl100dx.htm) gave the title compound: mp 217° C.; [α]$_D^{20}$ −51.5 (c=1.00, CHCl$_3$).

Method B: Racemic 2-(4-methanesulfonylphenyl)-3-(tetrahydropyran-4-yl)-N-thiazol-2-ylpropionamide (EXAMPLE 65) was separated by chiral stationary phase HPLC. Method: CHIRAL CEL OJ® (Daicel Chemical Industries, Ltd., Tokyo, Japan), 10 cm ⌀×25 cm, MeOH (100%), 189 mL/min, UV 285 nm, 25° C.; RT (S)=21.7 min; RT (R)=25.4 min. Analysis: CHIRAL CEL OJ-R® (Daicel Chemical Industries, Ltd., Tokyo, Japan), 4.6 mm ⌀×15 cm, CH$_3$CN-0.5M NaClO$_4$ (pH 2.0), 20:80, 0.5 mL/min, UV 225 nm, 25° C.; RT (S)=11.53 min; RT (R)=19.30 min.

Method A of EXAMPLE 93 was utilised to obtain the compounds listed in TABLE 10 from the appropriate heteroaromatic amine and enantiopure acid.

TABLE 10

| Ex | Structure | Name | [α]$_D^{20}$ (concn, solvent, temp) | m/z (APCI$^+$) |
|---|---|---|---|---|
| 94 | 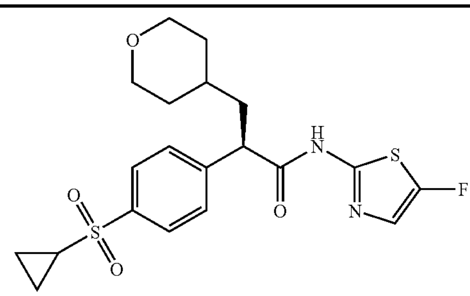 | (2R)-2-(4-Cyclopropane-sulfonylphenyl)-N-(5-fluorothiazol-2-yl)-3-(tetrahydropyran-4-yl)propionamide | −60.9 (c = 0.97, CHCl$_3$, 31° C.) | 439 [M + H]$^+$ |
| 95 | 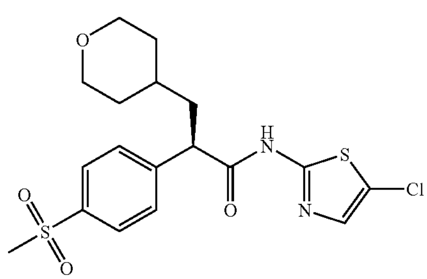 | (2R)-N-(5-Chlorothiazol-2-yl)-2-(4-methane-sulfonylphenyl)-3-(tetrahydropyran-4-yl)-propionamide | −125.0 (c = 0.73, CHCl$_3$, 25° C.) | 429 [M + H]$^+$ |
| 96 | 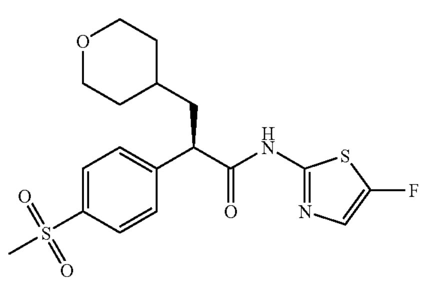 | (2R)-N-(5-Fluorothiazol-2-yl)-2-(4-methane-sulfonylphenyl)-3-(tetrahydropyran-4-yl)-propionamide | −67.1 (c = 0.82, CHCl$_3$, 25° C.) | 413 [M + H]$^+$ |

TABLE 10-continued

| Ex | Structure | Name | [α]$_D^{20}$ (concn, solvent, temp) | m/z (APCI$^+$) |
|---|---|---|---|---|
| 97 | 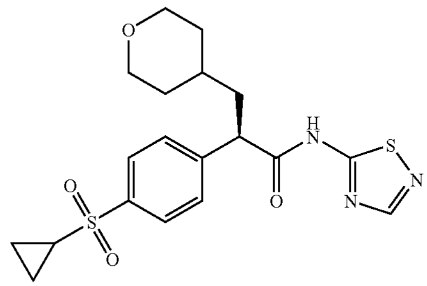 | (2R)-2-(4-Cyclopropane-sulfonylphenyl)-3-(tetrahydropyran-4-yl)-N-[1,2,4]thiadiazol-5-ylpropionamide | −71.9 (c = 0.93, CHCl$_3$, 30° C.) | 422 [M + H]$^+$ |
| 98 | 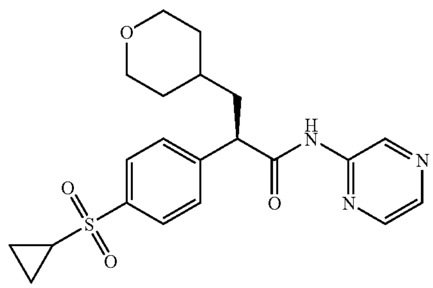 | (2R)-2-(4-Cyclopropane-sulfonylphenyl)-N-pyrazin-2-yl-3-(tetrahydropyran-4-yl)propionamide | −52.3 (c = 0.99, CHCl$_3$, 28° C.) | 416 [M + H]$^+$ |
| 99 | 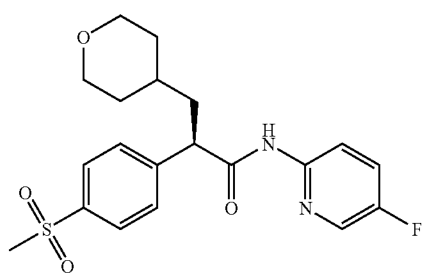 | (2R)-N-(5-Fluoropyridin-2-yl)-2-(4-methanesulfonylphenyl)-3-(tetrahydropyran-4-yl)propionamide | −54.0 (c = 0.63, CHCl$_3$, 25° C.) | 407 [M + H]$^+$ |
| 100 | 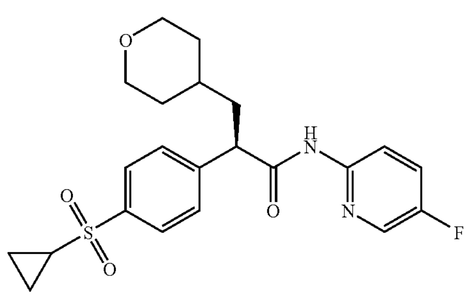 | (2R)-2-(4-Cyclopropane-sulfonylphenyl)-N-(5-fluoropyridin-2-yl)-3-(tetrahydropyran-4-yl)propionamide | −54.1 (c = 1.05, CHCl$_3$, 22° C.) | 433 [M + H]$^+$ |
| 101 | 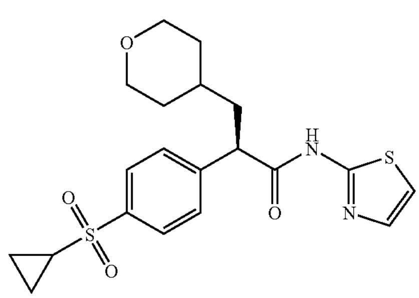 | (2R)-2-(4-Cyclopropane-sulfonylphenyl)-3-(tetrahydropyran-4-yl)-N-thiazol-2-ylpropionamide | −53.7 (c = 1.03, CHCl$_3$, 23° C.) | 421 [M + H]$^+$ |

TABLE 10-continued

| Ex | Structure | Name | $[\alpha]_D^{20}$ (concn, solvent, temp) | m/z (APCI+) |
|---|---|---|---|---|
| 102 | 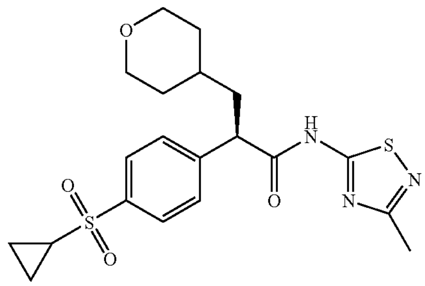 | (2R)-2-(4-Cyclopropane-sulfonylphenyl)-N-(3-methyl-[1,2,4]thiadiazol-5-yl)-3-(tetrahydropyran-4-yl)propionamide | −52.0 (c = 1.00, CHCl$_3$, 25° C.) | 436 [M + H]+ |

Method A of EXAMPLE 93 was also used to prepared the compounds listed in TABLE 11 from the appropriate heteroaromatic amine and enantiopure acid.

TABLE 11

| Ex | Structure | Name | RT$^A$ (min) | m/z (ES+) |
|---|---|---|---|---|
| 103 | 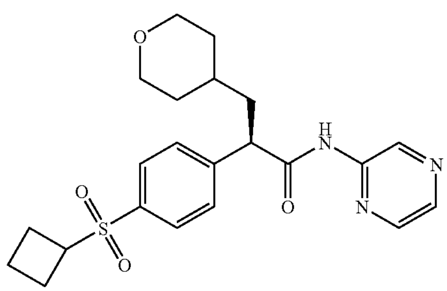 | (2R)-2-(4-Cyclobutane-sulfonylphenyl)-N-pyrazin-2-yl-3-(tetrahydropyran-4-yl)-propionamide | 3.29 | 430.2 [M + H]+ |
| 104 | 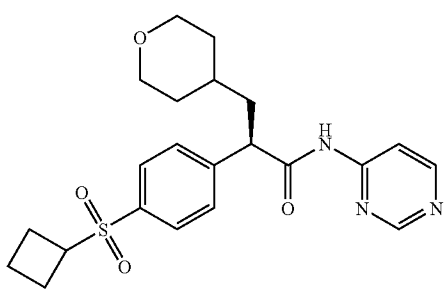 | (2R)-2-(4-Cyclobutane-sulfonylphenyl)-N-pyrimidin-4-yl-3-(tetrahydropyran-4-yl)-propionamide | 3.24 | 430.2 [M + H]+ |
| 105 | 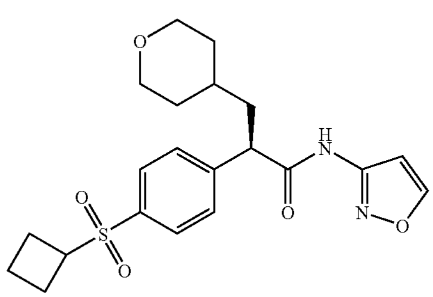 | (2R)-2-(4-Cyclobutane-sulfonylphenyl)-N-isoxazol-3-yl-3-(tetrahydropyran-4-yl)-propionamide | 3.49 | 419.2 [M + H]+ |

TABLE 11-continued

| Ex | Structure | Name | RT$^A$ (min) | m/z (ES$^+$) |
|---|---|---|---|---|
| 106 | 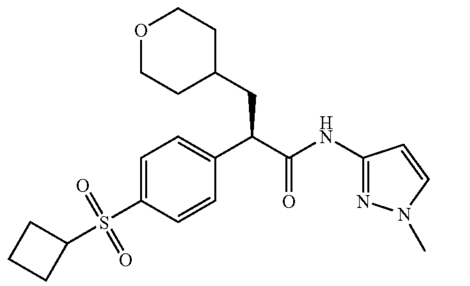 | (2R)-2-(4-Cyclobutane-sulfonylphenyl)-N-(1-methyl-1H-pyrazol-3-yl)-3-(tetrahydropyran-4-yl)-propionamide | 3.22 | 432.2 [M + H]$^+$ |
| 107 | 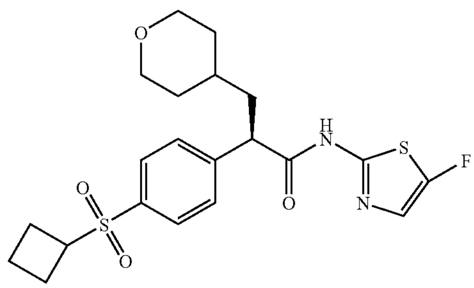 | (2R)-2-(4-Cyclobutane-sulfonylphenyl)-N-(5-fluorothiazol-2-yl)-3-(tetrahydropyran-4-yl)-propionamide | 3.82 | 494.1 [M + MeCN + H]$^+$ |
| 108 | 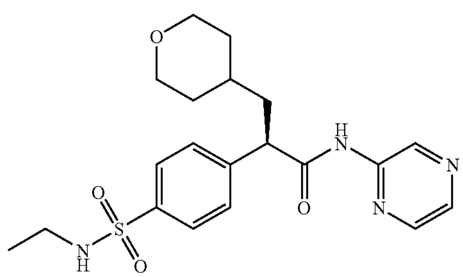 | (2R)-2-(4-Ethyl-sulfamoylphenyl)-N-pyrazin-2-yl-3-(tetrahydropyran-4-yl)-propionamide | 3.15 | 419.2 [M + H]$^+$ |
| 109 | 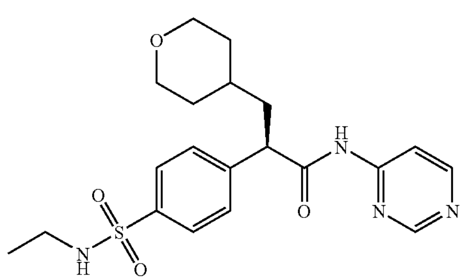 | (2R)-2-(4-Ethyl-sulfamoylphenyl)-N-pyrimidin-4-yl-3-(tetrahydropyran-4-yl)-propionamide | 3.09 | 419.2 [M + H]$^+$ |
| 110 | 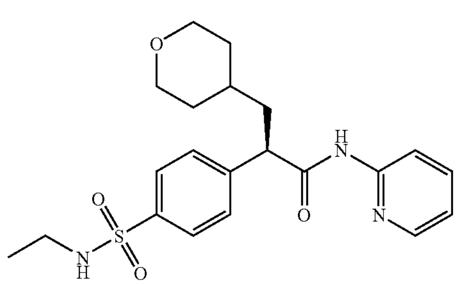 | (2R)-2-(4-Ethyl-sulfamoylphenyl)-N-pyridin-2-yl-3-(tetrahydropyran-4-yl)-propionamide | 3.26 | 418.1 [M + H]$^+$ |

TABLE 11-continued

| Ex | Structure | Name | RT$^A$ (min) | m/z (ES$^+$) |
|---|---|---|---|---|
| 111 | 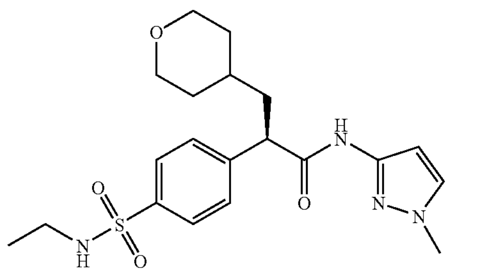 | (2R)-2-(4-Ethyl-sulfamoylphenyl)-N-(1-methyl-1H-pyrazol-3-yl)-3-(tetrahydropyran-4-yl)-propionamide | 3.12 | 421.1 [M + H]$^+$ |
| 112 | 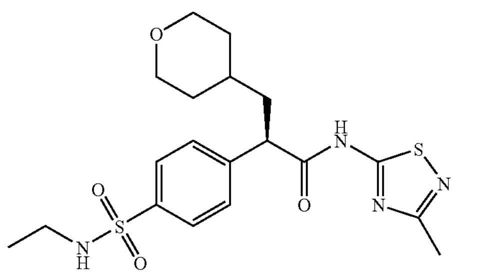 | (2R)-2-(4-Ethyl-sulfamoylphenyl)-N-(3-methyl-[1,2,4]-thiadiazol-5-yl)-3-(tetrahydropyran-4-yl)propionamide | 3.26 | 439.1 [M + H]$^+$ |
| 113 | 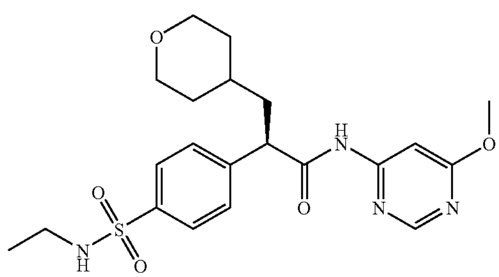 | (2R)-2-(4-Ethyl-sulfamoylphenyl)-N-(6-methoxypyrimidin-4-yl)-3-(tetrahydropyran-4-yl)propionamide | 3.54 | 449.1 [M + H]$^+$ |

Example 114

(E)-2-(4-Cyclopropanesulfonylphenyl)-N-(5-fluoro-pyridin-2-yl)-3-(tetrahydropyran-4-yl)acrylamide

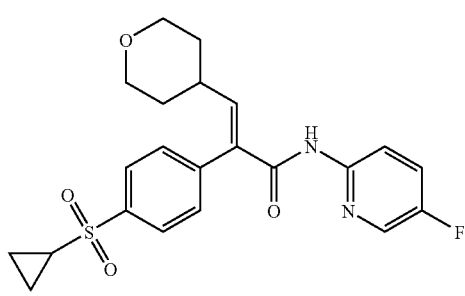

TFFH (283 mg, 1.07 mmol) and DIPEA (373 μmol, 2.14 mmol) were added to a stirred solution of (E)-2-(4-cyclopropanesulfonylphenyl)-3-(tetrahydropyran-4-yl)acrylic acid (Preparation 23, 300 mg, 0.89 mmol) in anhydrous CH$_2$Cl$_2$ (18 mL). After 30 min, the solution was treated portionwise with 2-amino-5-fluoropyridine (200 mg, 1.78 mmol) over 30 min, before being stirred further for 16 h. Solvent evaporation and purification by RP-HPLC furnished the title compound: RT$^A$=3.34 min; m/z (ES$^+$)=431.2 [M+H]$^+$.

The procedure exemplified by the preparation of EXAMPLE 114 was also used to prepare several other amides (TABLE 12).

TABLE 12

| Ex | Structure | Name | RT^A (min) | m/z (ES+) |
|---|---|---|---|---|
| 115 | 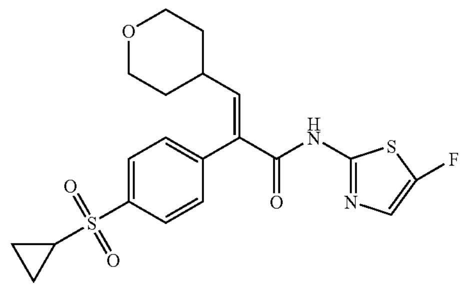 | (E)-2-(4-Cyclopropane-sulfonylphenyl)-N-(5-fluorothiazol-2-yl)-3-(tetrahydropyran-4-yl)acrylamide | 3.44 | 478.3 [M + MeCN + H]+ |
| 116 | 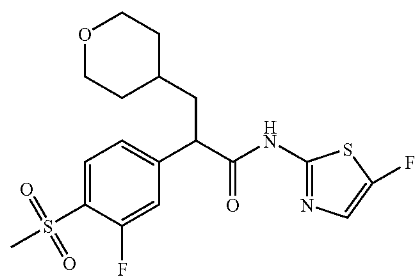 | 2-(3-Fluoro-4-methanesulfonylphenyl)-N-(5-fluorothiazol-2-yl)-3-(tetrahydropyran-4-yl)propionamide | 3.28 | 472.3 [M + MeCN + H]+ |
| 117 | 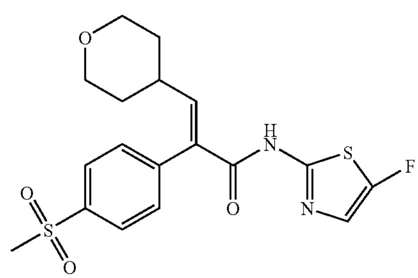 | (E)-N-(5-Fluorothiazol-2-yl)-2-(4-methanesulfonylphenyl)-3-(tetrahydropyran-4-yl)acrylamide | 3.24 | 452.3 [M + MeCN + H]+ |
| 118 | 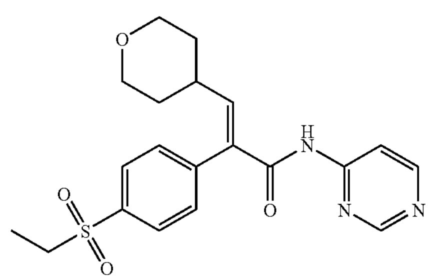 | (E)-2-(4-Ethanesulfonyl-phenyl)-N-pyrimidin-4-yl-3-(tetrahydropyran-4-yl)acrylamide | 3.12 | 402.1 [M + H]+ |
| 119 | 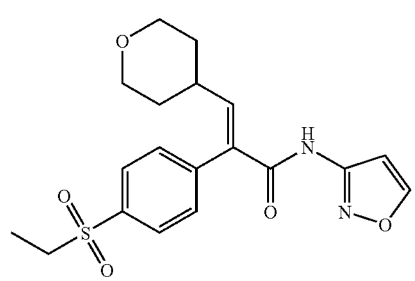 | (E)-2-(4-Ethanesulfonyl-phenyl)-N-isoxazol-3-yl-3-(tetrahydropyran-4-yl)acrylamide | 3.19 | 391.1 [M + H]+ |

| Ex | Structure | Name | RT^A (min) | m/z (ES+) |
|---|---|---|---|---|
| 120 | 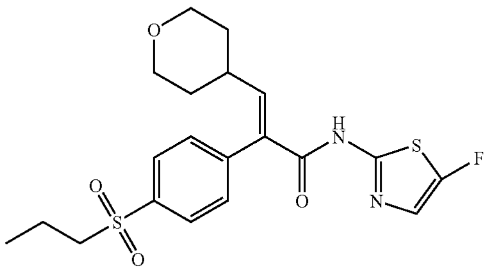 | (E)-N-(5-Fluorothiazol-2-yl)-2-[4-(propane-1-sulfonyl)phenyl]-3-(tetrahydropyran-4-yl)acrylamide | 3.67 | 439.1 [M + H]+ |
| 121 | 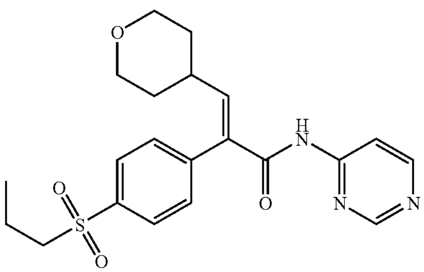 | (E)-2-[4-(Propane-1-sulfonyl)phenyl]-N-pyrimidin-4-yl-3-(tetrahydropyran-4-yl)acrylamide | 3.29 | 416.1 [M + H]+ |
| 122 | 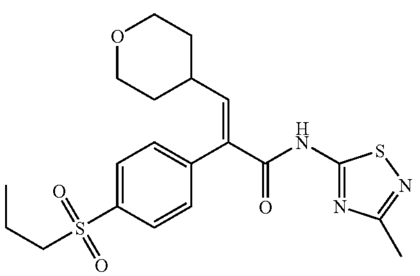 | (E)-N-(3-Methyl-[1,2,4]thiadiazol-5-yl)-2-[4-(propane-1-sulfonyl)-phenyl]-3-(tetrahydro-pyran-4-yl)acrylamide | 3.44 | 436.1 [M + H]+ |
| 123 | 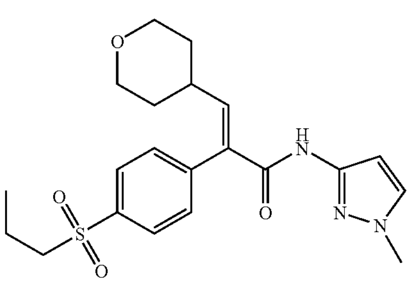 | (E)-N-(1-Methyl-1H-pyrazol-3-yl)-2-[4-(propane-1-sulfonyl)-phenyl]-3-(tetrahydro-pyran-4-yl)acrylamide | 3.26 | 418.3 [M + H]+ |

Example 124, Example 125, and Example 126

(E)-2-Phenyl-3-(tetrahydropyran-4-yl)-N-thiazol-2-ylacrylamide, (E)-2-(4-Formylphenyl)-N-(5-formylthiazol-2-yl)-3-(tetrahydropyran-4-yl)acrylamide, and (E)-N-(5-Formylthiazol-2-yl)-2-phenyl-3-(tetrahydropyran-4-yl)acrylamide

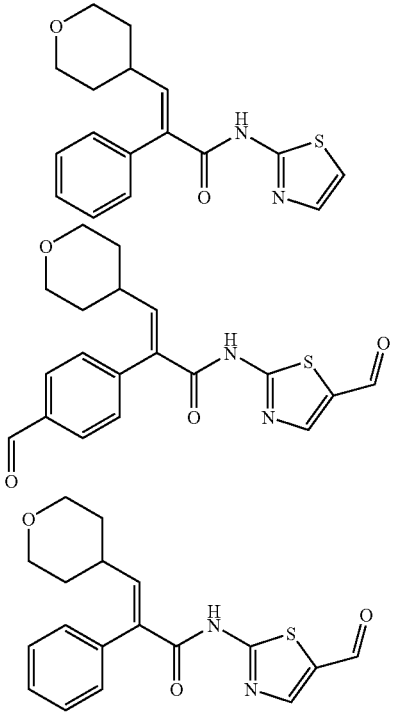

n-BuLi (17 mL of a 1.6M solution in hexanes, 27.2 mmol) was added to a stirred solution of (E)-2-(4-bromophenyl)-3-(tetrahydropyran-4-yl)-N-thiazol-2-ylacrylamide (EXAMPLE 12, 4.00 g, 10.2 mmol) in anhydrous THF (100 mL) at −78° C. After 110 min, the mixture was treated with anhydrous DMF (5 mL, 64.6 mmol), before being allowed to warm to 20° C. over 30 min. The reaction was quenched with 1M HCl, then the THF was evaporated off under reduced pressure. The aqueous phase was extracted with $CH_2Cl_2$, then the $CH_2Cl_2$ extracts were dried ($MgSO_4$), filtered, and concentrated. The residue was stirred with $Na_2S_2O_5$ solution. The solid produced was collected and triturated with EtOAc. This material was then suspended in EtOAc, then saturated aqueous $NaHCO_3$ was added with stirring. The layers were separated, then the aqueous phase was extracted with EtOAc and $CH_2Cl_2$. The combined organic layers were dried, filtered, concentrated, and subjected to column chromatography ($CH_2Cl_2$-THF, 93:7), to give EXAMPLE 125 ($RT^B$=1.30 min; m/z ($ES^+$)=371.2 $[M+H]^+$) and EXAMPLE 126 ($RT^B$=1.38 min; m/z ($ES^+$)=343.4 $[M+H]^+$). The EtOAc washings from the bisulfite addition complex were concentrated, then the residue was subjected to flash chromatography ($CH_2Cl_2$-THF, 24:1 to 93:7) to give EXAMPLE 124 ($RT^B$=1.39 min; m/z ($ES^+$)=315.3 $[M+H]^+$) and an additional quantity of EXAMPLE 126.

Example 127

2-[2-(4-Methanesulfonylphenyl)-3-(tetrahydropyran-4-yl)propionylamino]thiazole-5-carboxylic acid

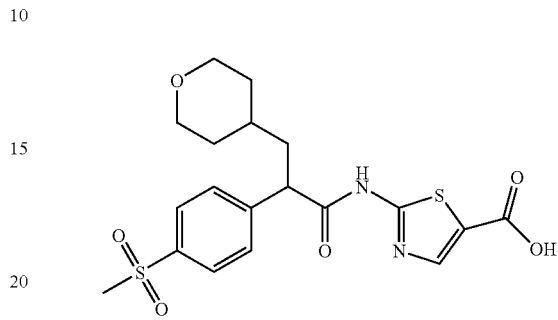

Ethyl 2-aminothiazole-5-carboxylate (2.21 g, 12.8 mmol) was condensed with 2-(4-methanesulfonylphenyl)-3-(tetrahydropyran-4-yl)propionic acid (Preparation 41, 1.00 g, 3.2 mmol) using the procedure described for EXAMPLE 65, to give ethyl 2-[2-(4-methanesulfonylphenyl)-3-(tetrahydropyran-4-yl)propionylamino]thiazole-5-carboxylate: m/z ($ES^+$)= 508.3 $[M+MeCN+H]^+$. $LiOH·H_2O$ (410 mg, 9.8 mmol) was added to a solution of this ester (1.44 g, 3.1 mmol) in THF-$H_2O$ (3:1, 30 mL). The mixture was stirred at 20° C. for 16 h and then at 55° C. for 24 h. The solvents were removed in vacuo, then the residue was dissolved in $H_2O$ (50 mL). The aqueous solution was washed with EtOAc (20 mL), before being acidified to pH 1 with 2M HCl and extracted with EtOAc (2×100 mL). The combined organic extracts were dried ($MgSO_4$), filtered and concentrated to give a solid that was recrystallised (EtOAc-MeOH) to give the title compound: $RT^A$=29.5 min; m/z ($ES^+$)=480.2 $[M+MeCH+H]^+$.

Example 128

2-[2-(4-Methanesulfonylphenyl)-3-(tetrahydropyran-4-yl)propionylamino]thiazole-5-carboxylic acid methoxy-methyl-amide

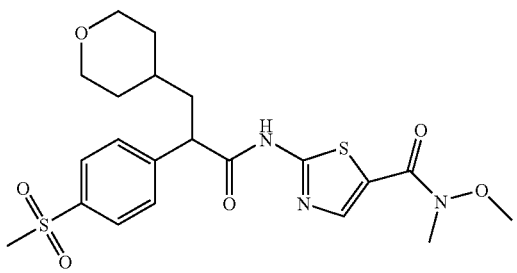

$NEt_3$ (647 μL, 4.64 mmol) and BOP (976 mg, 2.21 mmol) were added to a stirred solution of 2-[2-(4-methanesulfonylphenyl)-3-(tetrahydropyran-4-yl)propionylamino]thiazole-5-carboxylic acid (EXAMPLE 127, 968 mg, 2.21 mmol) in anhydrous DMF (30 mL). After 5 min, N,O-dimethylhydroxylamine hydrochloride (237 mg, 2.43 mmol) was added, then the mixture was stirred at 20° C. for 18 h. The solvents were removed in vacuo, then the residue was dissolved in EtOAc (75 mL). The EtOAc solution was washed with saturated aqueous $Na_2CO_3$ (40 mL), 2M HCl (40 mL), and brine (40 mL), before being dried ($MgSO_4$). Filtration and solvent evaporation provided the title compound: $RT^B$=1.27 min; m/z ($ES^+$)=482.0 $[M+H]^+$.

Example 129

2-[2-(4-Methanesulfonylphenyl)-3-(tetrahydropyran-4-yl)propionylamino]thiazole-5-carboxylic acid methylamide

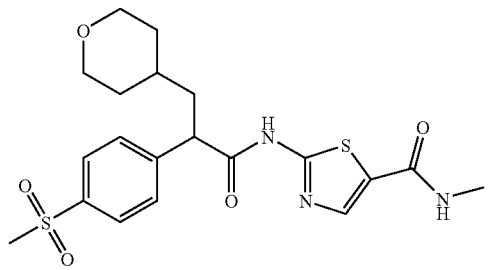

2-[2-(4-Methanesulfonylphenyl)-3-(tetrahydropyran-4-yl)propionylamino]thiazole-5-carboxylic acid (EXAMPLE 127, 399 mg, 0.91 mmol) was condensed with $MeNH_2.HCl$ in the presence of $NEt_3$, utilising the general procedure described in EXAMPLE 65, to give the title compound: $RT^A$=2.82 min; m/z ($ES^+$)=452.3 $[M+H]^+$.

Example 130

(E)-2-[2-(4-Methanesulfonylphenyl)-3-(tetrahydropyran-4-yl)acryloylamino]thiazole-5-carboxylic acid methylamide

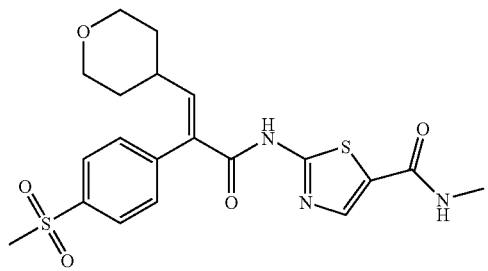

Ethyl 2-aminothiazole-5-carboxylate (0.73 g, 4.26 mmol) was condensed with (E)-2-(4-methanesulfonylphenyl)-3-(tetrahydropyran-4-yl)acrylic acid (Preparation 25, 0.33 g, 1.07 mmol), using the procedure described in EXAMPLE 65, to give (E)-ethyl 2-[2-(4-methanesulfonylphenyl)-3-(tetrahydropyran-4-yl)acryloylamino]thiazole-5-carboxylate: m/z ($ES^+$)=465.3 $[M+H]^+$. This ester (0.50 g, 1.07 mmol) was saponified, employing the protocol described in EXAMPLE 127, to furnish (E)-2-[2-(4-methanesulfonylphenyl)-3-(tetrahydropyran-4-yl)acryloylamino]thiazole-5-carboxylic acid: m/z ($ES^-$)=435.2 $[M-H]^-$. Utilising the approach described in EXAMPLE 129, this acid (0.16 g, 0.37 mmol) was transformed into the title compound: $RT^A$=2.87 min; m/z ($ES^+$)=450.2 $[M+H]^+$.

Example 131 and Example 132

N-(5-Formylthiazol-2-yl)-2-(4-methanesulfonylphenyl)-3-(tetrahydropyran-4-yl)propionamide and N-(5-Hydroxymethylthiazol-2-yl)-2-(4-methanesulfonylphenyl)-3-(tetrahydropyran-4-yl)propionamide

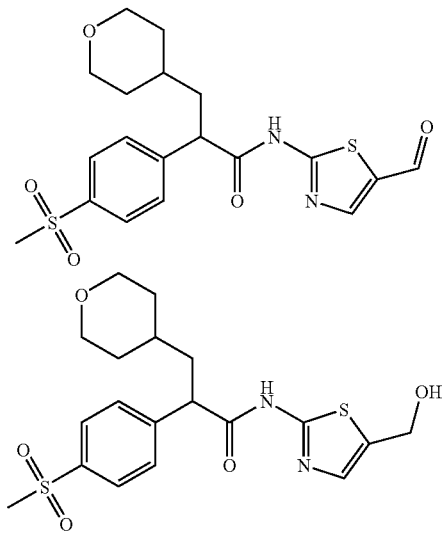

DIBAL (2.45 mL of a 1.5M solution in PhMe, 3.68 mmol) was added dropwise to a stirred solution of ethyl 2-[2-(4-methanesulfonylphenyl)-3-(tetrahydropyran-4-yl)propionylamino]thiazole-5-carboxylate (see EXAMPLE 127, 1.72 g, 3.68 mmol) in anhydrous $CH_2Cl_2$ (50 mL) at −78° C. After 50 min, more DIBAL (2.0 mL of a 1.5M solution in PhMe, 3.00 mmol) was added. The mixture was stirred further for 70 min, before being quenched with MeOH (3 mL) and 1M HCl (3 mL). On warming to 20° C., more 1M HCl (20 mL) was added. The organic phase was separated, dried ($MgSO_4$), filtered, and concentrated, before being purified by column chromatography (IH-EtOAc, 1:9 to 0:1, then MeOH:EtOAc, 1:9) to give the title aldehyde ($RT^A$=2.97 min; m/z ($ES^+$)= 464.2 $[M+MeCN+H]^+$) and the title alcohol ($RT^A$=2.56 min; m/z ($ES^+$)=425.3 $[M+H]^+$).

Example 133

N-(5-Cyanothiazol-2-yl)-2-(4-cyclopropanesulfonylphenyl)-3-(tetrahydropyran-4-yl)propionamide

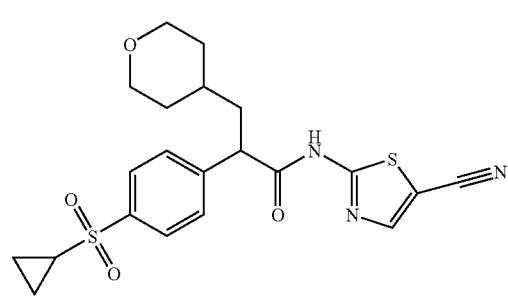

A stirred solution of 2-(4-cyclopropanesulfonylphenyl)-N-(5-formylthiazol-2-yl)-3-(tetrahydropyran-4-yl)propionamide (EXAMPLE 86, 369 mg, 0.82 mmol) in pyridine (1.53 mL) was treated with H$_2$NOH.HCl (63 mg, 0.91 mmol) at 0° C. The mixture was stirred at 20° C. for 3 h, before being warmed up to 60° C. and treated with Ac$_2$O (155 μL, 1.65 mmol). After 3 h, the mixture was cooled to 20° C., before being concentrated in vacuo and treated with CH$_2$Cl$_2$ (6 mL) and H$_2$O (6 mL). The aqueous phase was acidified to pH 3 with 10% aqueous citric acid. The organic layer was separated, then the aqueous layer was further extracted with CH$_2$Cl$_2$ (2×10 mL). The combined organic extracts were dried (MgSO$_4$), filtered, and concentrated to give a residue that was purified by column chromatography (IH-EtOAc, 1:3) to furnish the title compound: $RT^4$=3.40 min; m/z (ES$^+$)= 487.4 [M+MeCN+H]$^+$.

Example 134

N-(5-Cyanothiazol-2-yl)-2-(4-methanesulfonylphenyl)-3-(tetrahydropyran-4-yl)propionamide

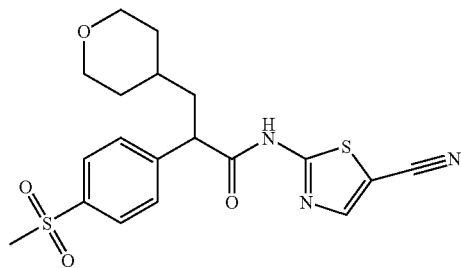

The procedure described in EXAMPLE 133 was employed to convert N-(5-formylthiazol-2-yl)-2-(4-methanesulfonylphenyl)-3-(tetrahydropyran-4-yl)propionamide (EXAMPLE 131, 200 mg, 0.47 mmol) into the title compound: $RT^4$=3.14 min; m/z (ES$^+$)=461.3 [M+MeCN+H]$^+$.

Example 135

Methyl {2-[2-(4-methanesulfonylphenyl)-3-(tetrahydropyran-4-yl)propionylamino]thiazol-5-ylmethyl}carbamate

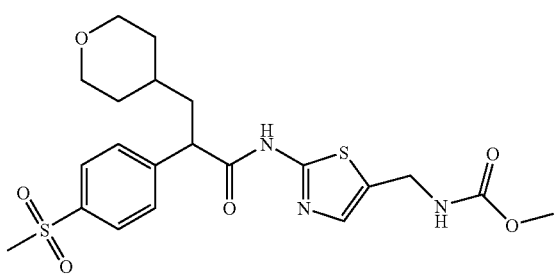

(NH$_4$)$_2$CO$_3$ (2.25 g, 34.1 mmol) was added to a stirred solution of N-(5-formylthiazol-2-yl)-2-(4-methanesulfonylphenyl)-3-(tetrahydropyran-4-yl)propionamide (EXAMPLE 131, 125 mg, 0.3 mmol) in MeOH (15 mL). After 16 h at 20° C., the mixture was concentrated, then the residue was partitioned between CH$_2$Cl$_2$ and H$_2$O. The organic layer was washed with Na$_2$CO$_3$ and 2M HCl, before being dried (MgSO$_4$). Filtration, solvent evaporation, and column chromatography (EtOAc) furnished the title compound: $RT^4$=1.07 min; m/z (ES$^+$)=482.3 [M+H]$^+$.

Example 136

(E)-3-(1-Formylpiperidin-4-yl)-2-(4-methanesulfonylphenyl)-N-thiazol-2-ylacrylamide

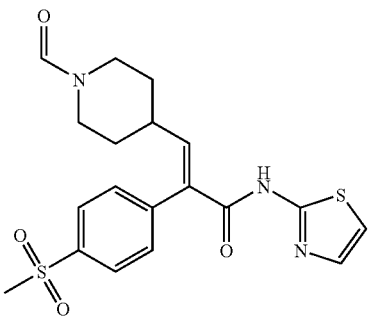

(E)-tert-Butyl 4-[2-carboxy-2-(4-methanesulfonylphenyl)vinyl]piperidine-1-carboxylate (Preparation 35, 3.17 g, 7.7 mmol) was condensed with thiazol-2-ylamine (2.32 g, 23.2 mmol), employing the procedure described in EXAMPLE 65, to give (E)-tert-butyl 4-[2-(4-methanesulfonylphenyl)-2-(thiazol-2-ylcarbamoyl)vinyl]piperidine-1-carboxylate: m/z (ES$^+$)=492.2 [M+H]$^+$. TFA (20 mL) was added to a stirred solution of the abovementioned carbamate (1.40 g, 2.8 mmol) in CH$_2$Cl$_2$ (20 mL). After 2 h, the solution was concentrated in vacuo. The residue was dissolved in H$_2$O, then the solution was washed with EtOAc. The aqueous layer was concentrated to furnish the trifluoroacetate salt of (E)-2-(4-methanesulfonylphenyl)-3-piperidin-4-yl-N-thiazol-2-ylacrylamide: m/z (ES$^+$)=392.1 [M+H]$^+$. A stirred solution of imidazole (102 mg, 1.5 mmol) in anhydrous DMF (1 mL) was treated with Me$_3$SiCl (114 μL, 0.9 mmol). After 20 min, the above trifluoroacetate salt (150 mg, 0.3 mmol) was added. The mixture was stirred for 16 h, before being partitioned between CH$_2$Cl$_2$ and 1M HCl. The organic layer was dried (MgSO$_4$), filtered, concentrated, and flash chromatographed (EtOAc-MeOH, 97:3 to 19:1). Recrystallisation (EtOAc) of the residue gave the title compound: $RT^4$=3.05 min; m/z (ES$^+$)=420.2 [M+H]$^+$.

Example 137 and Example 138

(E)-2-(4-Methanesulfonylphenyl)-3-(1-oxohexahydro-1λ$^4$-thiopyran-4-yl)-N-thiazol-2-ylacrylamide and (E)-3-(1,1-Dioxohexahydro-1λ$^6$-thiopyran-4-yl)-2-(4-methanesulfonylphenyl)-N-thiazol-2-ylacrylamide

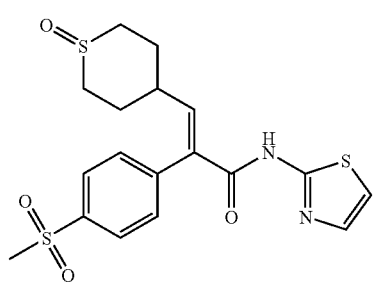

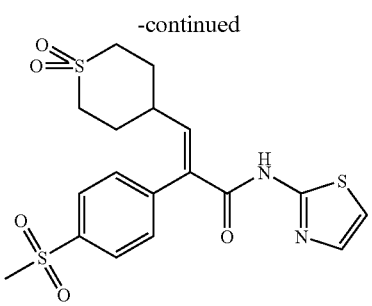

mCPBA (71 mg of 86% pure, 410 μmol) was added to a stirred solution of (E)-2-(4-methanesulfonylphenyl)-3-(tetrahydrothiopyran-4-yl)-N-thiazol-2-ylacrylamide (EXAMPLE 71, 96 mg, 230 μmol) in $CH_2Cl_2$ (5 mL). After 2 h, the reaction mixture was quenched with saturated aqueous $Na_2CO_3$ solution. The organic layer was washed with saturated aqueous $NaHCO_3$, before being dried ($MgSO_4$). Filtration, solvent evaporation, and flash chromatography (EtOAc then $CH_2Cl_2$-MeOH, 19:1) gave EXAMPLE 138 ($RT^A$=3.12 min; m/z ($ES^+$)=482.2 $[M+MeCN+H]^+$) and EXAMPLE 137 ($RT^A$=2.95 min; m/z ($ES^+$)=425.1 $[M+H]^+$).

Example 139 and Example 140

(E)-N-(5-Chlorothiazol-2-yl)-2-(4-methanesulfonylphenyl)-3-(1-oxohexahydro-1λ$^4$-thiopyran-4-yl) acrylamide and (E)-N-(5-Chlorothiazol-2-yl)-3-(1,1-dioxohexahydro-1λ$^6$-thiopyran-4-yl)-2-(4-methanesulfonylphenyl)acrylamide

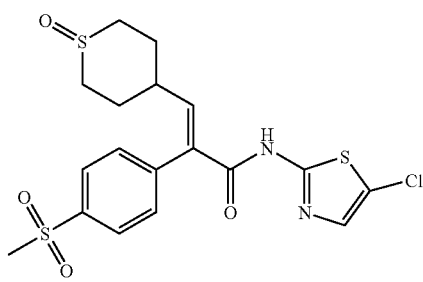

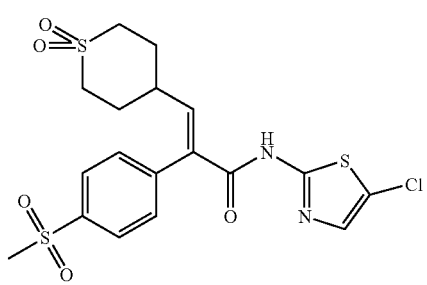

Incomplete oxidation of (E)-N-(5-chlorothiazol-2-yl)-2-(4-methanesulfonylphenyl)-3-(tetrahydrothiopyran-4-yl) acrylamide (EXAMPLE 72), employing the procedure described above for EXAMPLE 137 and EXAMPLE 138, furnished EXAMPLE 139 ($RT^B$=1.36 min; m/z ($ES^+$)=458.9 $[M+H]^+$) and EXAMPLE 140 ($RT^B$=1.48 min; m/z ($ES^+$)=515.9 $[M+MeCN+H]^+$).

Example 141 and Example 142

2-(3-Fluoro-4-methanesulfinylphenyl)-3-(tetrahydropyran-4-yl)-N-thiazol-2-ylpropionamide and 2-(3-Fluoro-4-methanesulfonylphenyl)-3-(tetrahydropyran-4-yl)-N-thiazol-2-ylpropionamide

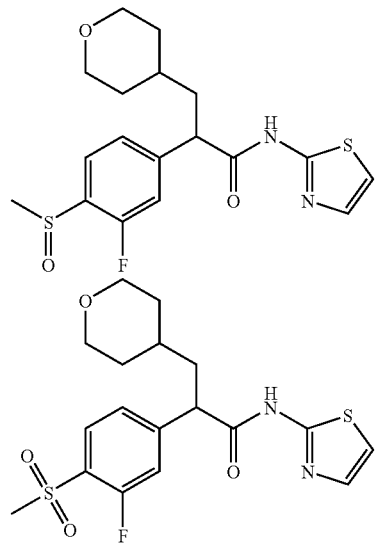

Incomplete oxidation of 2-(3-fluoro-4-methylsulfanylphenyl)-3-(tetrahydropyran-4-yl)-N-thiazol-2-ylpropionamide (EXAMPLE 85, 335 mg, 0.92 mmol) with 1.5 equiv of mCPBA, employing the procedure described above for EXAMPLE 137 and EXAMPLE 138, furnished EXAMPLE 141 ($RT^A$=3.06 min; m/z ($ES^+$)=397.1 $[M+H]^+$) and EXAMPLE 142 ($RT^A$=3.12 min; m/z ($ES^+$)=413.1 $[M+H]^+$).

Example 143

N-(5-Bromothiazol-2-yl)-2-(4-methanesulfonylphenyl)-3-(tetrahydropyran-4-yl)propionamide

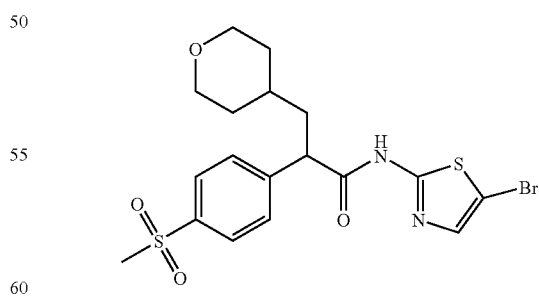

A solution of 2-(4-methanesulfonylphenyl)-3-(tetrahydropyran-4-yl)-N-thiazol-2-ylpropionamide (EXAMPLE 65, 202 mg, 510 μmol), NBS (91 mg, 510 μmol), and $Bz_2O_2$ (6 mg, 26 μmol), in $CCl_4$ (2 mL) was heated to reflux for 16 h. After removal of the solvent, the residue was partitioned between EtOAc (30 mL) and $H_2O$ (30 mL). The organic extracts were washed with saturated aqueous NH$_4$Cl (30 mL), before being dried (MgSO$_4$). Filtration, solvent evaporation, and flash chromatography (CH$_2$Cl$_2$-EtOAc, 2:3) gave the title compound: RT$^A$=3.50 min; m/z (ES$^+$)=516.2 [M+MeCN+H]$^+$.

Example 144

(E)-2-(4-Hydroxyphenyl)-3-(tetrahydropyran-4-yl)-N-thiazol-2-ylacrylamide

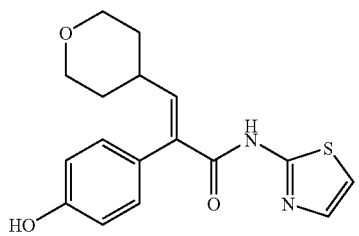

BBr$_3$ (2.5 mL of a 1.0M solution in CH$_2$Cl$_2$, 2.5 mmol) was added to a stirred solution of (E)-2-(4-methoxyphenyl)-3-(tetrahydropyran-4-yl)-N-thiazol-2-ylacrylamide (EXAMPLE 13, 340 mg, 984 µmol) in anhydrous CH$_2$Cl$_2$ (20 mL) at −78° C. After 1 h, the mixture was allowed to warm to 20° C. over a period of 24 h. CH$_2$Cl$_2$ (100 mL) was added, then the mixture was washed with H$_2$O (20 mL) and brine (20 mL), before being dried (MgSO$_4$). Filtration, solvent evaporation, and column chromatography (CH$_2$Cl$_2$-MeOH, 50:1) furnished the title compound: RT$^B$=1.27 min; m/z (ES$^+$)=331.0 [M+H]$^+$.

Example 145

(E)-2-(4-Methanesulfonylaminophenyl)-3-(tetrahydropyran-4-yl)-N-thiazol-2-ylacrylamide

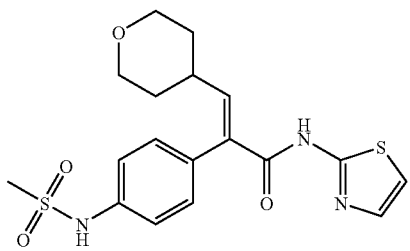

A stirred suspension of (E)-2-(4-nitrophenyl)-3-(tetrahydropyran-4-yl)-N-thiazol-2-ylacrylamide (EXAMPLE 81, 1.54 g, 4.0 mmol) in EtOH (54 mL) and THF (31 mL) was treated with H$_2$O (13 mL), saturated aqueous NH$_4$Cl (13 mL), and Fe powder (1.49 g, 26.7 mmol). After 4.5 h at 20° C., the reaction mixture was filtered through Celite, washing with CH$_2$Cl$_2$. The combined filtrates were concentrated and the residue was dissolved in CH$_2$Cl$_2$. The CH$_2$Cl$_2$ solution was washed with H$_2$O and dried (MgSO$_4$). Filtration, solvent evaporation, and column chromatography (EtOAc-MeOH, 19:1) gave (E)-2-(4-aminophenyl)-3-(tetrahydropyran-4-yl)-N-thiazol-2-ylacrylamide; m/z (ES$^+$)=330.1 [M+H]$^+$. A stirred solution of this compound (104 mg, 291 µmol) in anhydrous CH$_2$Cl$_2$ (4 mL) was treated with MeSO$_2$Cl (90 µL, 1165 µmol) and pyridine (94 µL, 1165 µmol). After 16 h, the mixture was diluted with CH$_2$Cl$_2$ (25 mL), before being extracted twice with 2M NaOH. The combined aqueous extracts were washed with Et$_2$O, before being acidified with 12M HCl to pH 1 and extracted twice with CH$_2$Cl$_2$. The combined organic extracts were washed with brine and dried (MgSO$_4$). Filtration and solvent evaporation afforded the title compound: RT$^B$=1.26 min; m/z (ES$^+$)=408.0 [M+H]$^+$.

Example 146

3-(Tetrahydropyran-4-yl)-2-[4-(tetrahydropyran-4-ylmethylsulfanyl)phenyl]-N-thiazol-2-ylpropionamide

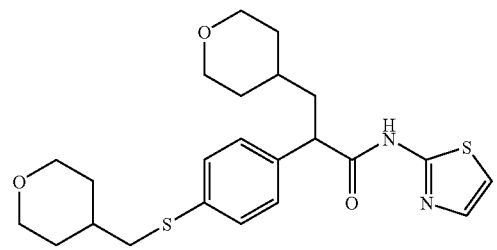

A solution of 2-(4-methoxymethylsulfanylphenyl)-3-(tetrahydropyran-4-yl)-N-thiazol-2-ylpropionamide (EXAMPLE 77, 1.29 g, 3.28 mmol) in THF (50 mL) was added to a stirred solution of AgNO$_3$ (0.59 g, 3.28 mmol) in EtOH (85 mL) at 40° C. The mixture was protected from light and stirred at 40° C. for 21 h. The solvents were evaporated off under reduced pressure, then the remaining solid was triturated with i-PrOH (60 mL), THF (60 mL), and Et$_2$O (60 mL). After air-drying, the solid was stirred vigorously with CH$_2$Cl$_2$ (200 mL) and 6M HCl (82 mL) for 4 h under Ar. The layers were separated, then the aqueous phase was extracted with CH$_2$Cl$_2$ (2×100 mL). The combined organic extracts were filtered through Celite, washed with brine (100 mL) and dried (MgSO$_4$). Filtration and solvent evaporation furnished 2-(4-mercaptophenyl)-3-(tetrahydropyran-4-yl)-N-thiazol-2-ylpropionamide: m/z (ES$^+$)=349.2 [M+H]$^+$. NEt$_3$ (0.14 mL, 1006 µmol) and a solution of 4-iodomethyltetrahydropyran (151 mg, 668 µmol) in anhydrous DMF (3 mL) were added to a stirred solution of this benzenethiol (197 mg, 565 µmol) in anhydrous DMF (7 mL) at 0° C. The mixture was warmed to 20° C., before being stirred for 16 h. The solvents were evaporated off under reduced pressure, then the residue was partitioned between CH$_2$Cl$_2$ (25 mL) and 2% aqueous citric acid (10 mL). The aqueous layer was extracted with CH$_2$Cl$_2$ (10 mL), then the combined organic layers were washed with H$_2$O (10 mL), saturated aqueous Na$_2$CO$_3$ (10 mL), H$_2$O (10 mL), and brine (10 mL). After drying (MgSO$_4$), filtration and solvent evaporation gave a residue that was subjected to flash chromatography (IH-EtOAc, 3:1 to 0:1) to furnish the title compound: RT$^A$=3.61 min; m/z (ES$^+$)=447.3 [M+H]$^+$.

Example 147

2-[4-(Pyridin-3-ylsulfanyl)phenyl]-3-(tetrahydropyran-4-yl)-N-thiazol-2-ylpropionamide

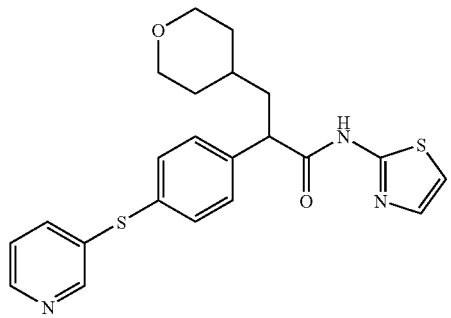

A solution of $Pd_2dba_3$ (18 mg, 20 μmol) and DPEPhos (24 mg, 45 μmol) in anhydrous PhMe (4 mL) was stirred at 20° C. for 3 min. 3-Iodopyridine (107 mg, 522 μmol), 2-(4-mercaptophenyl)-3-(tetrahydropyran-4-yl)-N-thiazol-2-ylpropionamide (see EXAMPLE 146, 173 mg, 500 μmol), and t-BuOK (65 mg, 579 μmol) were added, then the mixture was heated at 105° C. (bath) for 2.5 h. On cooling to 20° C., the mixture was diluted with $CH_2Cl_2$ (10 mL) and filtered through Celite, washing with $CH_2Cl_2$ (5 mL) and EtOAc (10 mL). Solvent evaporation and flash chromatography (IH-EtOAc, 3:1 to 0:1) afforded the title compound: $RT^B$=1.37 min; m/z (ES$^+$)= 426.0 [M+H]$^+$.

Example 148

3-(Tetrahydropyran-4-yl)-2-[4-(tetrahydropyran-4-ylmethanesulfonyl)phenyl]-N-thiazol-2-ylpropionamide

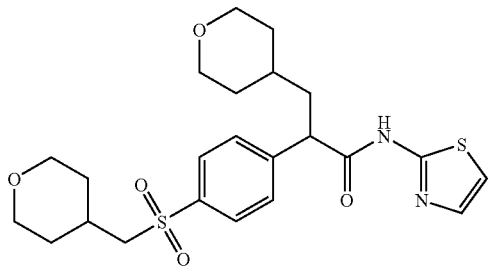

A stirred solution of 3-(tetrahydropyran-4-yl)-2-[4-(tetrahydropyran-4-ylmethylsulfanyl)phenyl]-N-thiazol-2-ylpropionamide (EXAMPLE 146, 146 mg, 327 μmol) in $CH_2Cl_2$ (7 mL) was treated with a solution of mCPBA (186 mg of 65% pure, 690 μmol) in $CH_2Cl_2$ (7 mL). After 4 d, saturated aqueous $Na_2CO_3$ (10 mL) was added, then the mixture was stirred vigorously for 5 min. The aqueous phase was extracted with $CH_2Cl_2$ (10 mL), then the combined organic extracts were washed with saturated aqueous $Na_2CO_3$ (10 mL), $H_2O$ (10 mL), and brine (10 mL), before being dried ($MgSO_4$). Filtration, solvent evaporation, and flash chromatography (EtOAc) provided the title compound: $RT^A$=3.26 min; m/z (ES$^+$)=479.3 [M+H]$^+$.

Several other sulfones were prepared by the oxidation of the appropriate thioether (TABLE 13) using the protocol described in EXAMPLE 148.

TABLE 13

| Ex | Structure | Name | RT (min) | m/z (ES$^+$) |
|---|---|---|---|---|
| 149 | 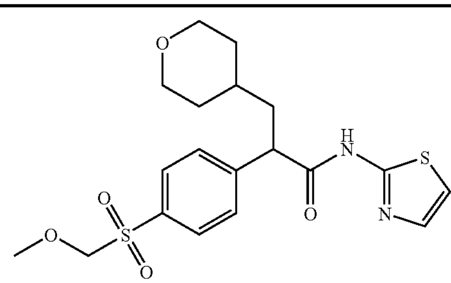 | 2-(4-Methoxymethanesulfonylphenyl)-3-(tetrahydropyran-4-yl)-N-(thiazol-2-yl-propionamide | 3.22[4] | 425.2 [M + H]$^+$ |
| 150 | 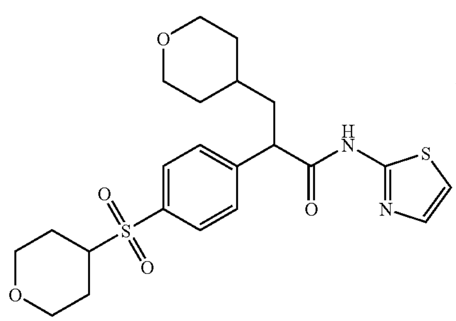 | 2-[4-(Tetrahydropyran-4-sulfonyl)phenyl]-3-(tetrahydropyran-4-yl)-N-thiazol-2-ylpropionamide | 3.04[4] | 465.1 [M + H]$^+$ |

TABLE 13-continued

| Ex | Structure | Name | RT (min) | m/z (ES+) |
|---|---|---|---|---|
| 151 | 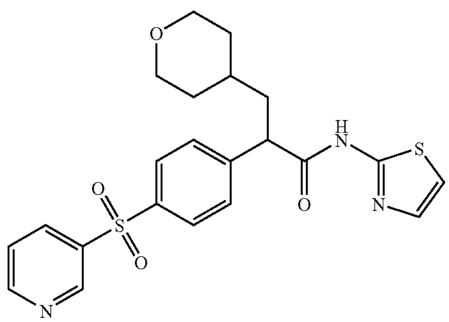 | 2-[4-(Pyridine-3-sulfonyl)-phenyl]-3-(tetrahydropyran-4-yl)-N-thiazol-2-ylpropionamide | 1.36[B] | 458.0 [M + H]+ |
| 152 | 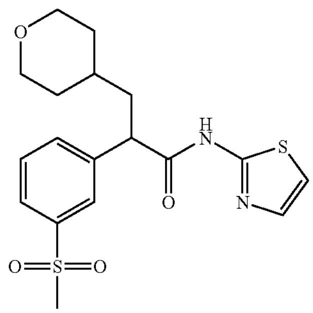 | 2-(3-Methanesulfonyl-phenyl)-3-(tetrahydropyran-4-yl)-N-thiazol-2-ylpropionamide | 1.28[B] | 395.0 [M + H]+ |

[A] RT employing Method A.
[B] RT employing Method B.

The compounds listed in TABLE 14 were prepared from 2-(4-mercaptophenyl)-3-(tetrahydropyran-4-yl)-N-thiazol-2-ylpropionamide (see EXAMPLE 146) by combining the procedures used to make EXAMPLES 146 and 148.

TABLE 14

| Ex | Structure | Name | RT (min) | m/z (ES+) |
|---|---|---|---|---|
| 153 | 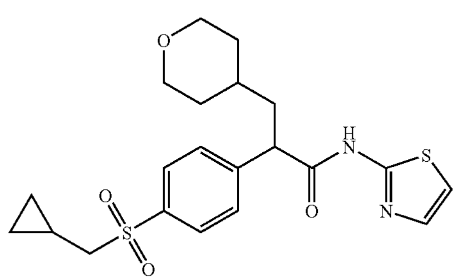 | 2-(4-Cyclopropylmethane-sulfonylphenyl)-3-(tetrahydropyran-4-yl)-N-thiazol-2-ylpropionamide | 1.42[B] | 435.0 [M + H]+ |
| 154 | 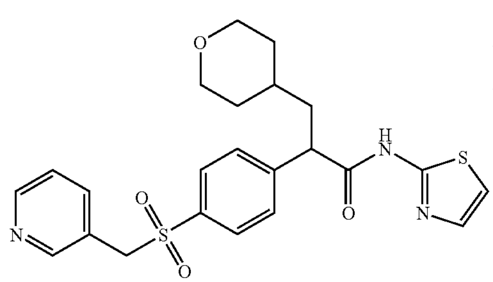 | 2-[4-(Pyridin-3-ylmethanesulfonyl)phenyl]-3-(tetrahydropyran-4-yl)-N-thiazol-2-ylpropionamide | 2.82[A] | 472.1 [M + H]+ |

TABLE 14-continued

| Ex | Structure | Name | RT (min) | m/z (ES+) |
|---|---|---|---|---|
| 155 | 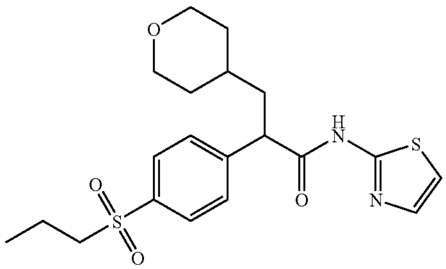 | 2-[4-(Propane-1-sulfonyl)-phenyl]-3-(tetrahydropyran-4-yl)-N-thiazol-2-ylpropionamide | 3.20[4] | 464.2 [M + MeCN + H]+ |
| 156 | 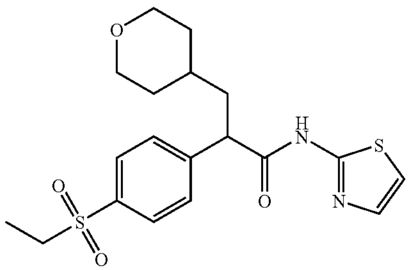 | 2-(4-Ethanesulfonylphenyl)-3-(tetrahydropyran-4-yl)-N-thiazol-2-ylpropionamide | 3.11[4] | 450.2 [M + MeCN + H]+ |
| 157 | 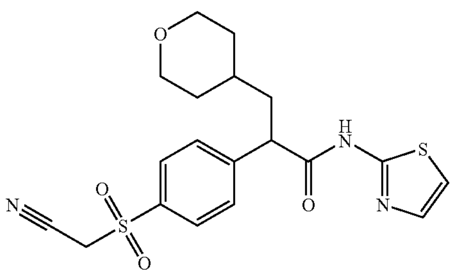 | 2-(4-Cyanomethanesulfonyl-phenyl)-3-(tetrahydropyran-4-yl)-N-thiazol-2-ylpropionamide | 3.15[4] | 420.2 [M + H]+ |
| 158 | 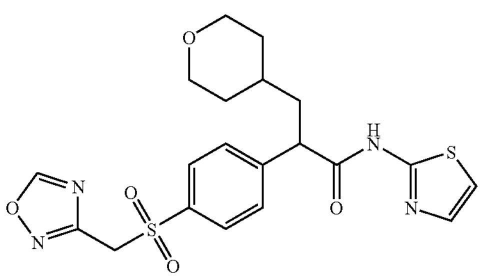 | 2-[4-([1,2,4]Oxadiazol-3-ylmethanesulfonyl)phenyl]-3-(tetrahydropyran-4-yl)-N-thiazol-2-ylpropionamide | 3.06[4] | 463.2 [M + H]+ |
| 159 | 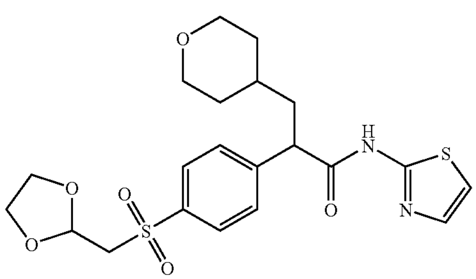 | 2-[4-([1,3]Dioxolan-2-ylmethanesulfonyl)phenyl]-3-(tetrahydropyran-4-yl)-N-thiazol-2-ylpropionamide | 3.11[4] | 508.3 [M + MeCN + H]+ |

TABLE 14-continued

| Ex | Structure | Name | RT (min) | m/z (ES+) |
|---|---|---|---|---|
| 160 | 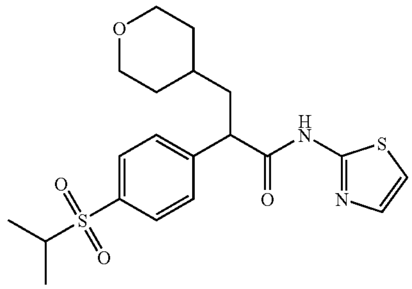 | 2-[4-(Propane-2-sulfonyl)-phenyl]-3-(tetrahydropyran-4-yl)-N-thiazol-2-ylpropionamide | 3.17[A] | 423.3 [M + H]+ |

[A]RT employing Method A.
[B]RT employing Method B.

Example 161

2-[4-(Oxetane-3-sulfonyl)phenyl]-3-(tetrahydropyran-4-yl)-N-thiazol-2-ylpropionamide

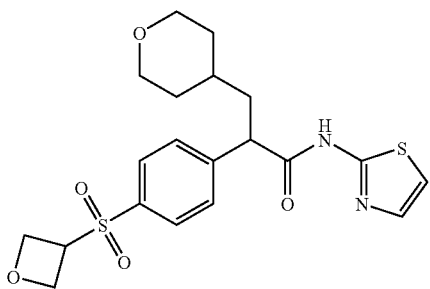

A mixture of 2-(4-mercaptophenyl)-3-(tetrahydropyran-4-yl)-N-thiazol-2-ylpropionamide (see EXAMPLE 146, 349 mg, 1.0 mmol), $K_2CO_3$ (152 mg, 1.1 mmol), NaI (150 mg, 1.0 mmol), and 3-(tosyloxy)oxetane (274 mg, 1.2 mmol) in anhydrous DMAc (20 mL) was heated for 2 h at 130° C. The solvent was evaporated off under reduced pressure, then the residue was partitioned between $CH_2Cl_2$ (75 mL) and 2% aqueous citric acid (20 mL). The organic layer was washed with $H_2O$ (20 mL), saturated aqueous $Na_2CO_3$ (20 mL), and brine (20 mL), before being dried ($MgSO_4$). Filtration and solvent evaporation afforded 2-[4-(oxetan-3-ylsulfanyl)phenyl]-3-(tetrahydropyran-4-yl)-N-thiazol-2-ylpropionamide: m/z (ES+)=405.2 [M+H]+. This thioether was oxidised employing the protocol outlined in EXAMPLE 148 to give the title compound: $RT^A$=3.04 min; m/z (ES+)=437.2 [M+H]+.

The compounds listed in TABLE 15 were synthesized employing the protocols described in EXAMPLE 161.

TABLE 15

| Ex | Structure | Name | RT^A (min) | m/z (ES+) |
|---|---|---|---|---|
| 162 | 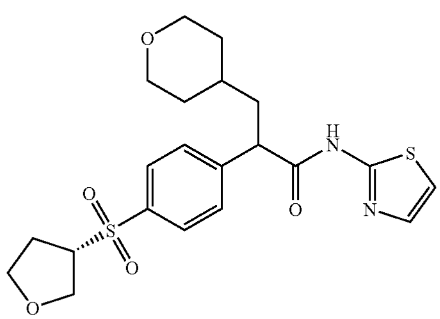 | 2-[4-((3S)-Tetrahydrofuran-3-sulfonyl)phenyl]-3-(tetrahydropyran-4-yl)-N-thiazol-2-ylpropionamide | 3.07 | 451.3 [M + H]+ |

TABLE 15-continued

| Ex | Structure | Name | RT[4] (min) | m/z (ES[+]) |
|---|---|---|---|---|
| 163 | 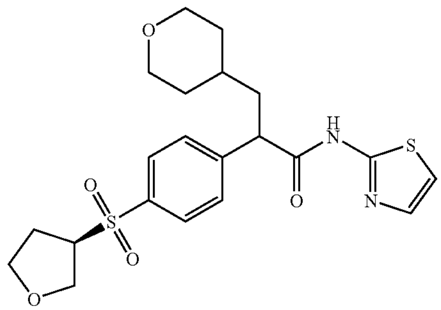 | 2-[4-((3R)-Tetrahydrofuran-3-sulfonyl)phenyl]-3-(tetrahydropyran-4-yl)-N-thiazol-2-ylpropionamide | 2.96 | 451.2 [M + H][+] |
| 164 | 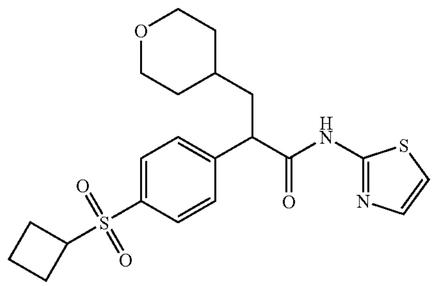 | 2-(4-Cyclobutane-sulfonylphenyl)-3-(tetrahydropyran-4-yl)-N-thiazol-2-ylpropionamide | 3.31 | 476.3 [M + MeCN + H][+] |

Example 165

2-[4-(2-Oxopropane-1-sulfonyl)phenyl]-3-(tetrahydropyran-4-yl)-N-thiazol-2-ylpropionamide

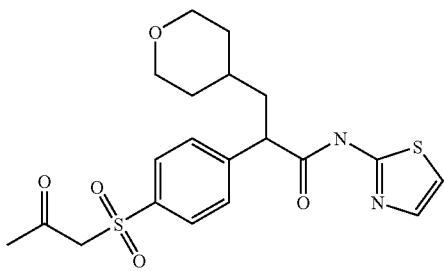

Reaction of 2-(4-mercaptophenyl)-3-(tetrahydropyran-4-yl)-N-thiazol-2-ylpropionamide (see EXAMPLE 146, 363 mg, 1.04 mmol) with chloroacetone (90 μL, 1.10 mmol) employing a procedure similar to that described in EXAMPLE 146, furnished 2-[4-(2-oxopropylsulfanyl)phenyl]-3-(tetrahydropyran-4-yl)-N-thiazol-2-ylpropionamide: m/z (ES[+])=405.3 [M+H][+]. TBA-OX (2.46 g, 2.44 mmol) was added to a stirred solution of the abovementioned thioether (399 mg, 0.99 mmol) in $CH_2Cl_2$ (20 mL). After 19 h, the reaction mixture was treated with more TBA-OX (0.97 g, 0.96 mmol). An additional quantity of TBA-OX (1.09 g, 1.07 mmol) was added 20 h later, then the mixture was stirred further for 3 d. Solvent evaporation and flash chromatography (IH-EtOAc, 3:2 to 0:1) afforded the title compound: RT[4]=3.12 min; m/z (ES[+])=437.2 [M+H][+].

The compounds listed in TABLE 16 were obtained from 2-(4-mercaptophenyl)-3-(tetrahydropyran-4-yl)-N-thiazol-2-ylpropionamide (see EXAMPLE 146) by combining the procedure used to make EXAMPLE 147 with that used to prepare EXAMPLES 141 and 142.

TABLE 16

| Ex | Structure | Name | RT[4] (min) | m/z (ES[+]) |
|---|---|---|---|---|
| 166 | 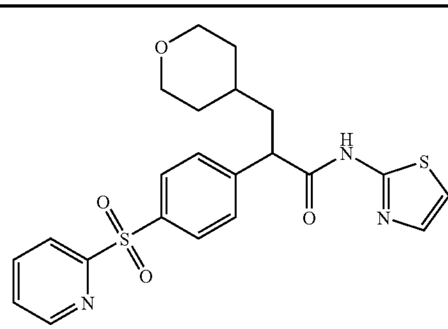 | 2-[4-(Pyridine-2-sulfonyl)phenyl]-3-(tetrahydropyran-4-yl)-N-thiazol-2-ylpropionamide | 3.20 | 458.3 [M + H][+] |

TABLE 16-continued

| Ex | Structure | Name | RT^A (min) | m/z (ES+) |
|---|---|---|---|---|
| 167 | 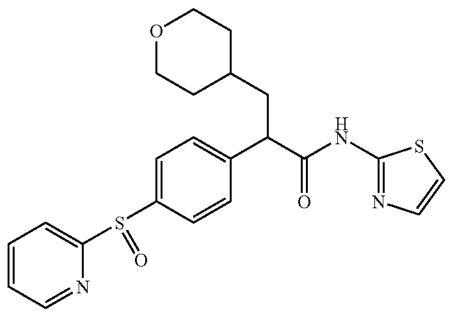 | 2-[4-(Pyridine-2-sulfinyl)phenyl]-3-(tetrahydropyran-4-yl)-N-thiazol-2-ylpropionamide | 3.07 | 442.3 [M + H]+ |
| 168 | 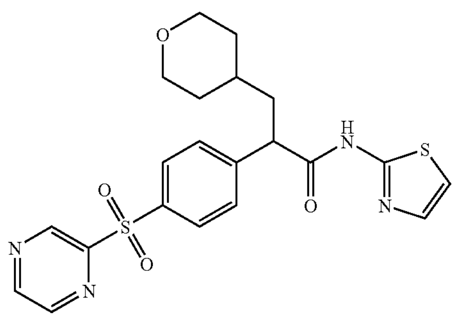 | 2-[4-(Pyrazine-2-sulfonyl)phenyl]-3-(tetrahydropyran-4-yl)-N-thiazol-2-ylpropionamide | 3.19 | 459.3 [M + H]+ |
| 169 | 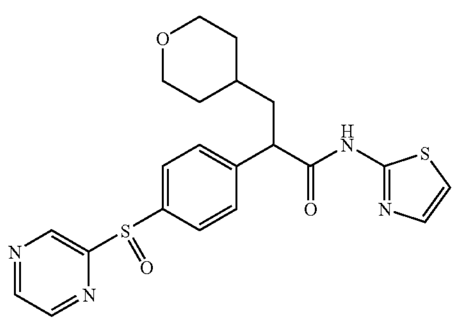 | 2-[4-(Pyrazine-2-sulfinyl)phenyl]-3-(tetrahydropyran-4-yl)-N-thiazol-2-ylpropionamide | 3.00 | 443.3 [M + H]+ |
| 170 | 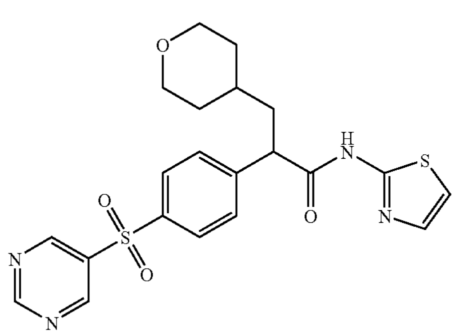 | 2-[4-(Pyrimidine-5-sulfonyl)phenyl]-3-(tetrahydropyran-4-yl)-N-thiazol-2-ylpropionamide | 3.18 | 459.3 [M + H]+ |

Example 171

2-(3-Amino-4-methanesulfonylphenyl)-3-(tetrahydropyran-4-yl)-N-thiazol-2-ylpropionamide

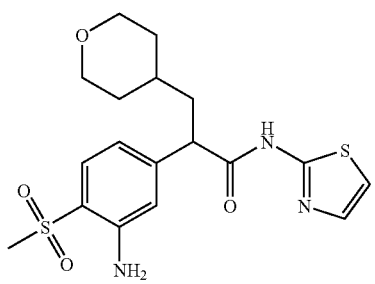

2-(4-Methylsulfanyl-3-nitrophenyl)-3-(tetrahydropyran-4-yl)-N-thiazol-2-ylpropionamide (EXAMPLE 80, 5.84 g, 13.2 mmol) was oxidized with mCPBA following the procedure described in EXAMPLE 148 to give 2-(4-methanesulfonyl-3-nitrophenyl)-3-(tetrahydropyran-4-yl)-N-thiazol-2-ylpropionamide: m/z (ES$^+$)=481.1 [M+MeCN+H]$^+$. This compound (520 mg, 1.2 mmol) was reduced, employing the procedure described in EXAMPLE 145, to give the title compound: RT$^A$=2.95 min; m/z (ES$^+$)=426.1 [M+NH$_4$]$^+$.

Example 172

2-(3-Chloro-4-methanesulfonylphenyl)-3-(tetrahydropyran-4-yl)-N-thiazol-2-ylpropionamide

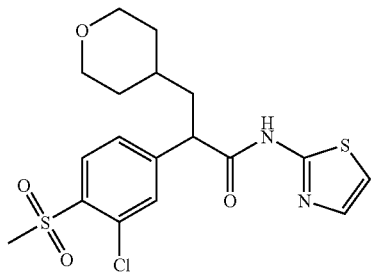

A solution of NaNO$_2$ (34 mg, 498 μmol) in H$_2$O (0.8 mL) was added to a solution of 2-(3-amino-4-methanesulfonylphenyl)-3-(tetrahydropyran-4-yl)-N-thiazol-2-ylpropionamide (EXAMPLE 171, 200 mg, 488 μmol) in 6M HCl (1.6 mL) at 0° C. The reaction was stirred at 0° C. for 35 min, before being added slowly to a stirred mixture of Cu powder (80 mg, 1.26 mmol) and 12M HCl (0.8 mL) at 0° C. The temperature was increased to 20° C., then stirring was continued for 1 h. The mixture was then heated at 60° C. for 1 h, before being cooled down to 20° C. and extracted with CH$_2$Cl$_2$ (3×15 mL). The organic extracts were dried (MgSO$_4$), filtered, and concentrated to give a residue that was purified by RP-HPLC to furnish the title compound: RT$^A$=3.17 min; m/z (ES$^+$)=429.2 [M+H]$^+$.

Example 173

2-[4-(Morpholine-4-sulfonyl)phenyl]-3-(tetrahydropyran-4-yl)-N-thiazol-2-ylpropionamide

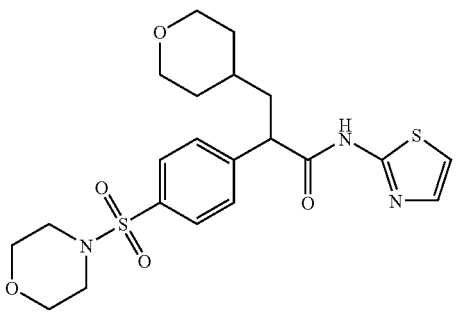

NEt$_3$ (120 μL, 868 μmol) and morpholine (76 μL, 868 μmol) were added to a stirred solution of 4-[2-(tetrahydropyran-4-yl)-1-(thiazol-2-ylcarbamoyl)ethyl]benzenesulfonyl chloride (Preparation 59, 300 mg, 723 μmol) in anhydrous DMF (4 mL). After 10 min, the solvents were removed in vacuo, then the residue was taken up in CH$_2$Cl$_2$ (50 mL). The CH$_2$Cl$_2$ solution was washed with H$_2$O (20 mL), 1M HCl (20 mL), H$_2$O (20 mL), saturated aqueous Na$_2$CO$_3$ (20 mL), and brine (20 mL), before being dried (MgSO$_4$). Filtration, solvent evaporation, and recrystallisation (CH$_2$Cl$_2$-IH) gave the title compound: RT$^A$=3.15 min; m/z (ES$^+$)=466.1 [M+H]$^+$.

The sulfonamides listed in TABLE 17 were synthesised by employing protocols similar to those described in EXAMPLE 173.

TABLE 17

| Ex | Structure | Name | RT$^A$ (min) | m/z (ES$^+$) |
|---|---|---|---|---|
| 174 | ![structure] | 2-(4-Sulfamoylphenyl)-3-(tetrahydropyran-4-yl)-N-thiazol-2-ylpropionamide | 2.93 | 396.1 [M + H]$^+$ |

TABLE 17-continued

| Ex | Structure | Name | RT^A (min) | m/z (ES+) |
|---|---|---|---|---|
| 175 | 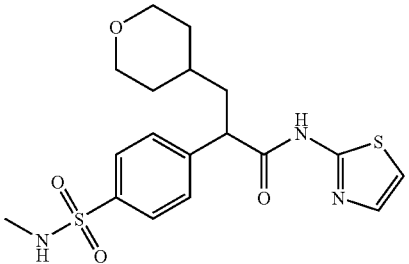 | 2-(4-Methylsulfamoyl-phenyl)-3-(tetrahydro-pyran-4-yl)-N-thiazol-2-ylpropionamide | 3.00 | 410.2 [M + H]+ |
| 176 | 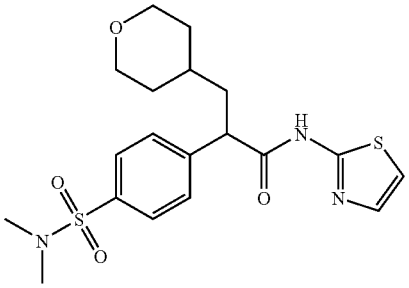 | 2-(4-Dimethylsulfamoyl-phenyl)-3-(tetrahydro-pyran-4-yl)-N-thiazol-2-ylpropionamide | 3.19 | 424.1 [M + H]+ |
| 177 | 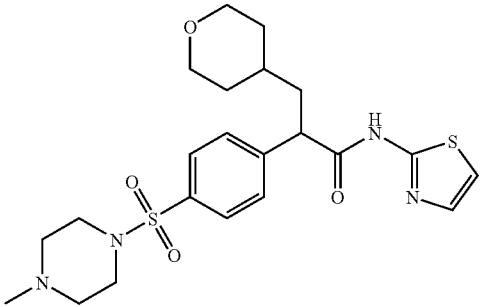 | 2-[4-(4-Methylpiperazine-1-sulfonyl)phenyl]-3-(tetrahydropyran-4-yl)-N-thiazol-2-ylpropionamide | 2.64 | 479.2 [M + H]+ |
| 178 | 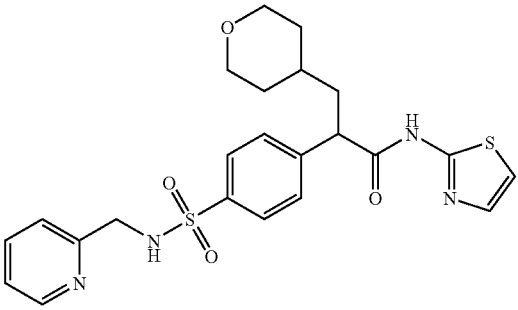 | 2-{4-[(Pyridin-2-ylmethyl)-sulfamoyl]phenyl}-3-(tetrahydropyran-4-yl)-N-thiazol-2-ylpropionamide | 2.82 | 487.1 [M + H]+ |
| 179 | 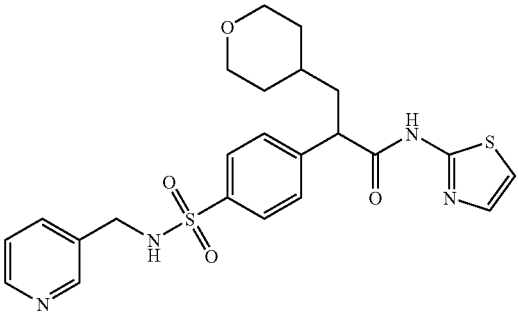 | 2-{4-[(Pyridin-3-ylmethyl)-sulfamoyl]phenyl}-3-(tetrahydropyran-4-yl)-N-thiazol-2-ylpropionamide | 2.70 | 487.1 [M + H]+ |

TABLE 17-continued

| Ex | Structure | Name | RT^A (min) | m/z (ES+) |
|---|---|---|---|---|
| 180 | 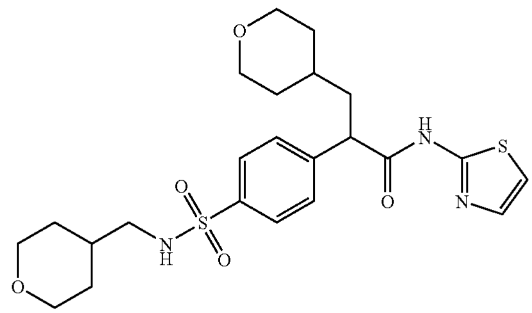 | 3-(Tetrahydropyran-4-yl)-2-{4-[(tetrahydropyran-4-ylmethyl)sulfamoyl]-phenyl}-N-thiazol-2-ylpropionamide | 3.07 | 494.1 [M + H]+ |
| 181 | 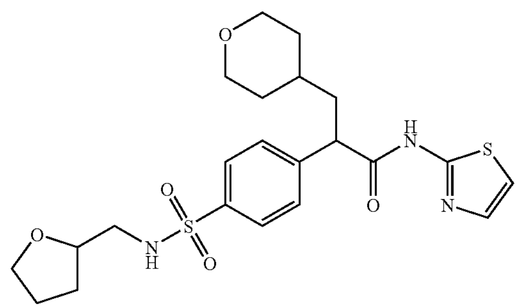 | 2-{4-[(Tetrahydrofuran-2-ylmethyl)sulfamoyl]-phenyl}-3-(tetrahydro-pyran-4-yl)-N-thiazol-2-ylpropionamide | 3.19 | 480.3 [M + H]+ |
| 182 | 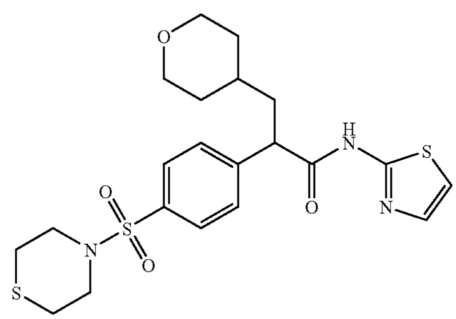 | 3-(Tetrahydropyran-4-yl)-N-thiazol-2-yl-2-[4-(thiomorpholine-4-sulfonyl)phenyl]-propionamide | 3.42 | 482.1 [M + H]+ |
| 183 | 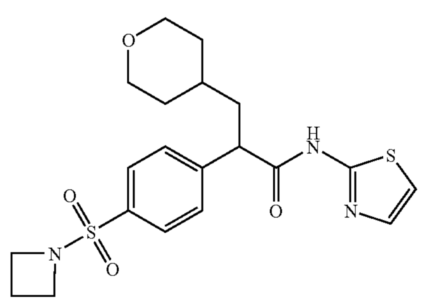 | 2-[4-(Azetidine-1-sulfonyl)phenyl]-3-(tetrahydropyran-4-yl)-N-thiazol-2-ylpropionamide | 3.15 | 436.1 [M + H]+ |
| 184 | 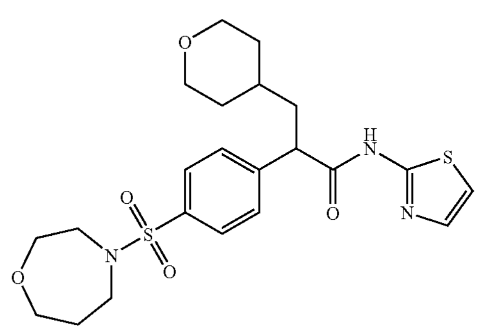 | 2-[4-([1,4]Oxazepane-4-sulfonyl)phenyl]-3-(tetrahydropyran-4-yl)-N-thiazol-2-ylpropionamide | 3.14 | 480.3 [M + H]+ |

TABLE 17-continued

| Ex | Structure | Name | RT^A (min) | m/z (ES+) |
|---|---|---|---|---|
| 185 | 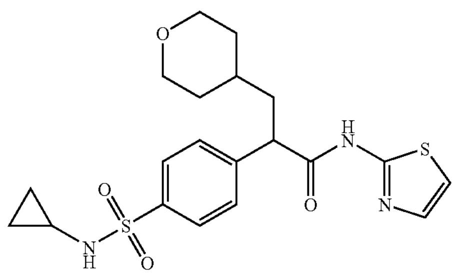 | 2-(4-Cyclopropyl-sulfamoylphenyl)-3-(tetrahydropyran-4-yl)-N-thiazol-2-ylpropionamide | 3.20 | 470.3 [M + MeCN + H]+ |
| 186 | 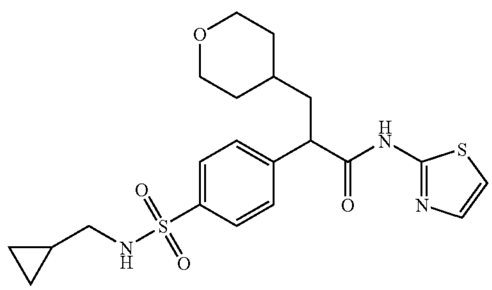 | 2-[4-(Cyclopropylmethyl-sulfamoyl)phenyl]-3-(tetrahydropyran-4-yl)-N-thiazol-2-ylpropionamide | 3.24 | 450.3 [M + H]+ |
| 187 | 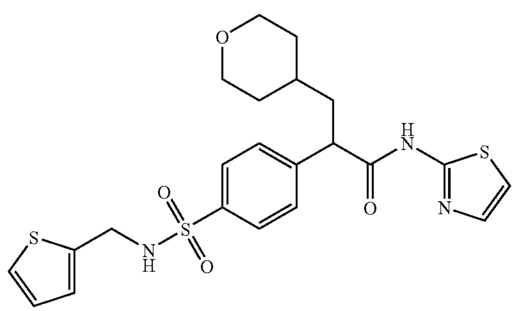 | 3-(Tetrahydropyran-4-yl)-N-thiazol-2-yl-2-{4-[(thiophen-2-ylmethyl)-sulfamoyl]phenyl}-propionamide | 3.31 | 492.1 [M + H]+ |
| 188 | 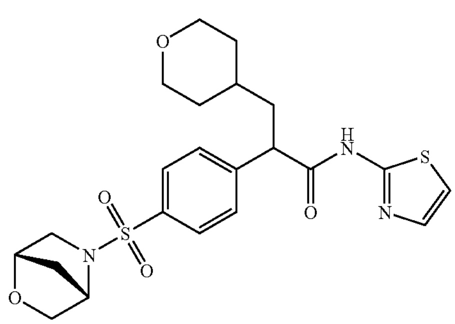 | 2-[4-((1S,4S)-2-Oxa-5-azabicyclo[2.2.1]heptane-5-sulfonyl)phenyl]-3-(tetrahydropyran-4-yl)-N-thiazol-2-ylpropionamide | 3.06 | 478.3 [M + H]+ |
| 189 | 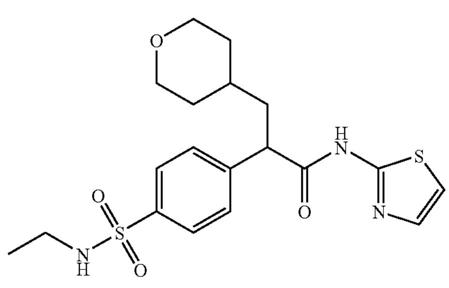 | 2-(4-Ethylsulfamoyl-phenyl)-3-(tetrahydropyran-4-yl)-N-thiazol-2-ylpropionamide | 3.17 | 424.2 [M + H]+ |

TABLE 17-continued

| Ex | Structure | Name | RT^A (min) | m/z (ES+) |
|---|---|---|---|---|
| 190 | 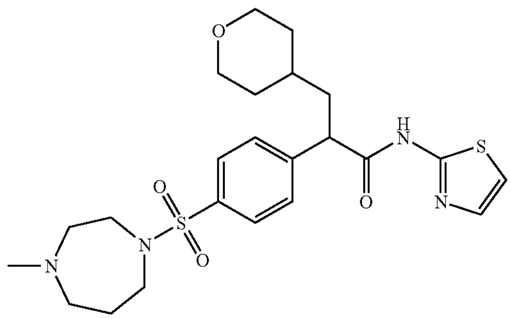 | 2-[4-(4-Methyl-[1,4]diazepane-1-sulfonyl)phenyl]-3-(tetrahydropyran-4-yl)-N-thiazol-2-ylpropionamide | 2.59 | 493.3 [M + H]+ |
| 191 | 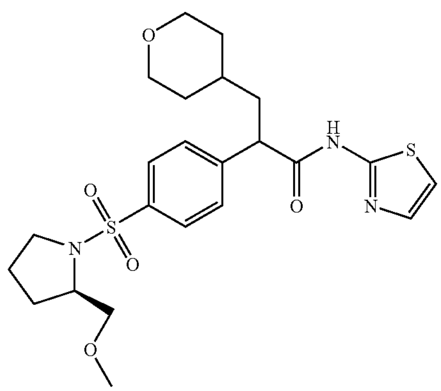 | 2-[4-((2R)-2-Methoxymethyl-pyrrolidine-1-sulfonyl)-phenyl]-3-(tetrahydropyran-4-yl)-N-thiazol-2-ylpropionamide | 3.37 | 494.3 [M + H]+ |
| 192 | 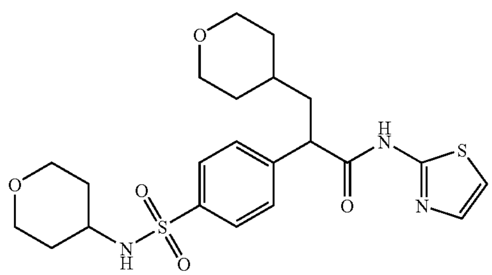 | 3-(Tetrahydropyran-4-yl)-2-[4-(tetrahydropyran-4-ylsulfamoyl)phenyl]-N-thiazol-2-ylpropionamide | 3.03 | 480.3 [M + H]+ |
| 193 | 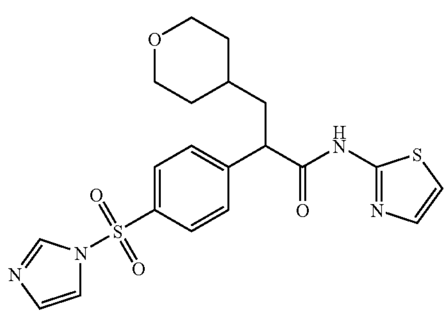 | 2-[4-(Imidazole-1-sulfonyl)phenyl]-3-(tetrahydropyran-4-yl)-N-thiazol-2-ylpropionamide | 3.15 | 447.3 [M + H]+ |
| 194 | 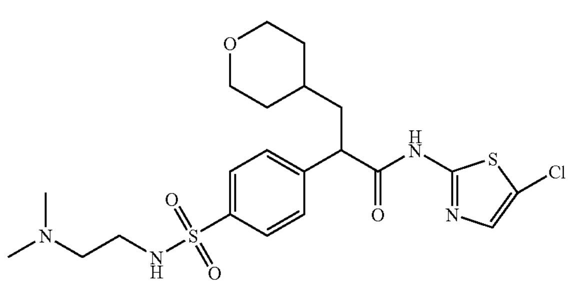 | N-(5-Chlorothiazol-2-yl)-2-[4-(2-dimethylamino-ethylsulfamoyl)phenyl]-3-(tetrahydropyran-4-yl)propionamide | 2.52 | 501.1 [M + H]+ |

TABLE 17-continued

| Ex | Structure | Name | RT^A (min) | m/z (ES+) |
|---|---|---|---|---|
| 195 | 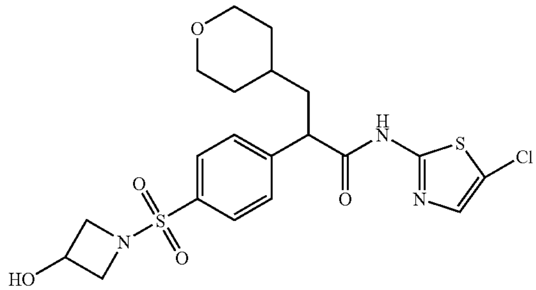 | N-(5-Chlorothiazol-2-yl)-2-[4-(3-hydroxyazetidine-1-sulfonyl)phenyl]-3-(tetrahydropyran-4-yl)propionamide | 3.81 | 545.2 [M + MeCN + NH4]+ |
| 196 | 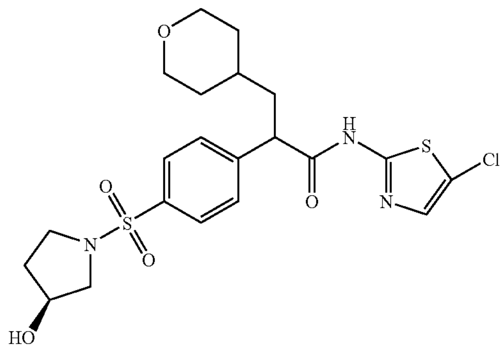 | N-(5-Chlorothiazol-2-yl)-2-[4-((3S)-3-hydroxypyrrolidine-1-sulfonyl)phenyl]-3-(tetrahydropyran-4-yl)propionamide | 3.29 | 500.3 [M + H]+ |
| 197 | 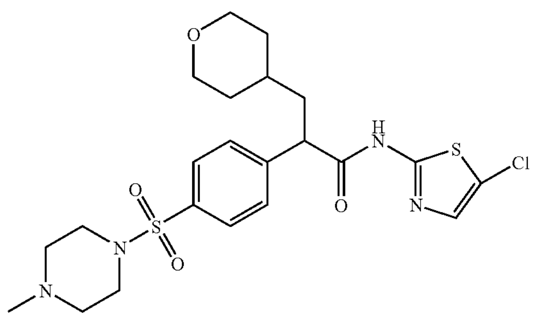 | N-(5-Chlorothiazol-2-yl)-2-[4-(4-methylpiperazine-1-sulfonyl)phenyl]-3-(tetrahydropyran-4-yl)propionamide | 2.76 | 513.4 [M + H]+ |

Example 198

N-(5-Chlorothiazol-2-yl)-2-[4-(piperazine-1-sulfonyl)phenyl]-3-(tetrahydropyran-4-yl)propionamide

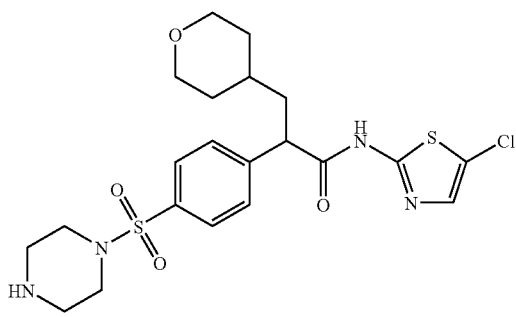

NEt$_3$ (278 µL, 2.0 mmol) and tert-butyl piperazine-1-carboxylate (373 mg, 2.0 mmol) were added to a stirred solution of 4-[1-(5-chlorothiazol-2-ylcarbamoyl)-2-(tetrahydropyran-4-yl)ethyl]benzenesulfonyl chloride (Preparation 60, 449 mg, 1.0 mmol) in anhydrous DMAc (4 mL). The mixture was stirred for 16 h, then the solvents were removed in vacuo. The residue was dissolved in EtOAc (50 mL) to give a solution that was washed with H$_2$O (15 mL), saturated aqueous Na$_2$CO$_3$ (15 mL), and brine (15 mL), before being dried (MgSO$_4$). Filtration, solvent evaporation, and column chromatography (IH-EtOAc, 7:3 to 1:1) gave tert-butyl 4-{4-[1-(5-chlorothiazol-2-ylcarbamoyl)-2-(tetrahydropyran-4-yl)ethyl]benzenesulfonyl}piperazine-1-carboxylate: m/z (ES+)= 599.5 [M+H]+. A solution of this compound (189 mg, 316 µmol) in CH$_2$Cl$_2$-TFA (1:1, 7 mL) was stirred for 1 h. The solvents were evaporated off under reduced pressure, then the residue was triturated with Et$_2$O. The product was collected, washed with Et$_2$O, and air-dried to furnish the trifluoroacetate salt of the title compound: RT$^A$=2.64 min; m/z (ES+)=499.3 [M+H]+.

The compounds listed in TABLE 18 were synthesized as their trifluoroacetate salts employing the procedures described in EXAMPLE 198.

TABLE 18

| Ex | Structure | Name | RT$^A$ (min) | m/z (ES$^+$) |
|---|---|---|---|---|
| 199 | 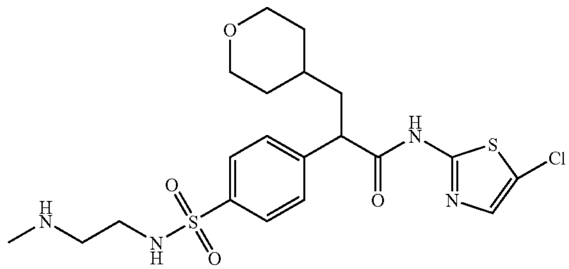 | N-(5-Chlorothiazol-2-yl)-2-[4-(2-methylamino-ethylsulfamoyl)phenyl]-3-(tetrahydropyran-4-yl)propionamide | 2.54 | 487.3 [M + H]$^+$ |
| 200 | 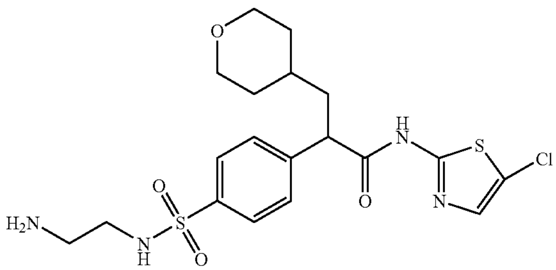 | 2-[4-(2-Amino-ethylsulfamoyl)phenyl]-N-(5-chlorothiazol-2-yl)-3-(tetrahydropyran-4-yl)propionamide | 2.44 | 473.3 [M + H]$^+$ |

Example 201

N-Ethyl-4-[2-(tetrahydropyran-4-yl)-1-(thiazol-2-ylcarbamoyl)ethyl]benzamide

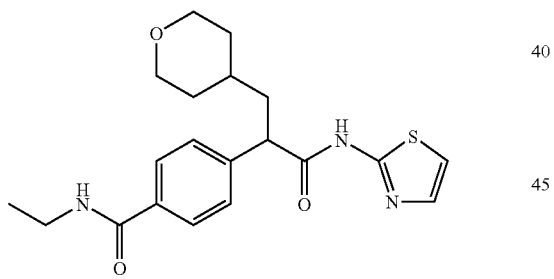

4-[2-(Tetrahydropyran-4-yl)-1-(thiazol-2-ylcarbamoyl)ethyl]benzoic acid (Preparation 62, 150 mg, 420 μmol) was condensed with EtNH$_2$.HCl in the presence of DIPEA, utilising the general procedure described in EXAMPLE 65, to give the title compound: RT$^A$=2.97 min; m/z (ES$^+$)=388.3 [M+H]$^+$.

$^1$H NMR data for several Examples are catalogued in TABLE 19.

TABLE 19

| Ex | Solvent | δ$_H$ |
|---|---|---|
| 34 | CDCl$_3$ | 1.15-1.22(m, 2H), 1.40-1.50(m, 4H), 1.55-1.70(m, 2H), 2.10-2.25(m, 1H), 2.55-2.65(m, 1H), 3.20-3.30(m, 2H), 3.85-3.95(m, 2H), 7.02(d, 1H), 7.13(d, 1H), 7.41(d, 1H), 7.47(d, 2H), 8.05(d, 2H), 8.45-8.53(br, 1H) |
| 68 | CDCl$_3$ | 1.40-1.70(m, 4H), 2.13-2.22(m, 1H), 3.16(s, 3H), 3.21-3.31(m, 2H), 3.85-3.95(m, 2H), 7.01(d, 1H), 7.11(d, 1H), 7.40(d, 1H), 7.48(d, 2H), 8.10(d, 2H) |
| 94 | CDCl$_3$ | 1.00-1.06(m, 2H), 1.25-1.50(m, 5H), 1.55-1.65(m, 2H), 1.75-1.85(m, 1H), 2.15-2.25(m, 1H), 2.42-2.51(m, 1H), 3.25-3.33(m, 2H), 3.76-3.85(m, 1H), 3.88-3.96(m, 2H), 7.02(d, 1H), 7.46(d, 2H), 7.84(d, 2H), 10.49(s, 1H) |
| 98 | CDCl$_3$ | 1.00-1.10(m, 2H), 1.30-1.50(m, 5H), 1.55-1.70(m, 2H), 1.79-1.87(m, 1H), 2.20-2.28(m, 1H), 2.42-2.50(m, 1H), 3.26-3.37(m, 2H), 3.75-3.80(m, 1H), 3.90-4.00(m, 2H), 7.57(d, 2H), 7.76(s, 1H), 7.93(d, 2H), 8.21(d, 1H), 8.38(d, 1H), 9.55(s, 1H) |
| 100 | CDCl$_3$ | 1.00-1.10(m, 2H), 1.30-1.55(m, 5H), 1.60-1.70(m, 2H), 1.75-1.85(m, 1H), 2.15-2.25(m, 1H), 2.40-2.50(m, 1H), 3.25-3.35(m, 2H), 3.68-3.78(m, 1H), |

TABLE 19-continued

| Ex | Solvent | $\delta_H$ |
|---|---|---|
| | | 3.90-3.98(m, 2H), 7.40-7.45(m, 1H), 7.56(d, 2H), 7.89(d, 2H), 7.93(s, 1H), 8.09(s, 1H), 8.19-8.27(m, 1H) |
| 103 | CDCl$_3$ | 0.85-0.95(m, 2H), 1.40-1.65(m, 5H), 1.75-1.85(m, 1H), 1.95-2.05(m, 1H), 2.15-2.30(m, 2H), 2.55-2.60(m, 2H), 3.25-3.35(m, 2H), 3.75-3.95(m, 4H), 7.56(d, 2H), 7.85(d, 2H), 8.17(d, 1H), 8.20-8.25(br, 1H), 8.35(d, 1H), 9.52(s, 1H) |
| 107 | CDCl$_3$ | 0.80-0.90(m, 2H), 1.25-1.45(m, 3H), 1.50-1.65(m, 2H), 1.75-1.85(m, 1H) 1.95-2.05(m, 2H), 2.15-2.25(m, 1H), 2.50-2.62(m, 2H), 3.23-3.32(m, 2H), 3.75-3.95(m, 4H), 7.00(d, 1H), 7.45(d, 2H), 7.81(d, 2H), 9.73(br s, 1H) |
| 114 | CDCl$_3$ | 0.80-0.90(m, 1H), 1.10-1.20(m, 2H), 1.40-1.55(m, 4H), 1.60-1.70(m, 2H), 2.55-2.65(m, 1H), 3.25-3.35(m, 2H), 3.90-4.00(m, 2H), 6.95(d, 1H), 7.40-7.55(m, 3H), 8.00-8.15(m, 4H), 8.35-8.40(m, 1H) |
| 115 | CDCl$_3$ | 1.12-1.20(m, 2H), 1.40-1.55(m, 4H), 1.60-1.70(m, 2H), 2.10-2.21(m, 1H), 2.53-2.62(m, 1H), 3.20-3.30(m, 2H), 3.85-3.95(m, 2H), 7.00(d, 1H), 7.09(d, 1H), 7.43(d, 2H), 8.04(d, 2H), 8.10(s, 1H) |
| 117 | (CD$_3$)$_2$SO | 1.45-1.55(m, 4H), 2.25-2.35(m, 1H), 3.15-3.25(m, 2H), 3.30(s, 3H), 3.75-3.85(m, 2H), 6.75(d, 1H), 7.31(s, 1H), 7.49(d, 2H), 7.93(d, 2H) |

The following compounds may also be synthesised using the procedures described above:

2-(3-Chloro-4-methanesulfonylphenyl)-N-(5-fluorothiazol-2-yl)-3-(tetrahydropyran-4-yl)propionamide;

2-(4-Methanesulfonyl-3-trifluoromethylphenyl)-N-(5-fluorothiazol-2-yl)-3-(tetrahydropyran-4-yl)propionamide; and 2-(3,4-Dichlorophenyl)-N-(5-fluorothiazol-2-yl)-3-(tetrahydropyran-4-yl)propionamide.

Assays

In Vitro GK Activity

Using a protocol similar to that described in WO 00/58293, GK activity was assayed by coupling the production of G6P by GST-GK to the generation of NADPH with G6PDH as the coupling enzyme.

The GK assay was performed at 30° C. in a flat bottom 96-well assay plate from Costar with a final incubation volume of 100 µL. The assay buffer contained: 25 mM Hepes buffer (pH 7.4), 12.5 mM KCl, 5 mM D-Glc, 5 mM ATP, 6.25 mM NADP, 25 mM MgCl$_2$, 1 mM dithiothreitol, test compound or 5% DMSO, 3.0 unit/mL G6PDH, and 0.4 µL/mL GST-GK, derived from human liver GK. ATP, G6PDH, and NADP were purchased from Roche Diagnostics. The other reagents were >98% pure and were purchased from Kanto Chemicals. The test compounds were dissolved in DMSO, before being added to the assay buffer without ATP. This mix was preincubated in the temperature controlled chamber of a SPECTRAmax 250 microplate spectrophotometer (Molecular Devices Corporation, Sunnyvale, Calif.) for 10 min, then the reaction was started by the addition of 10 µL ATP solution.

After starting the reaction, the increase in optical density (OD) at 340 nm was monitored over a 10 min incubation period as a measure of GK activity. Sufficient GST-GK was added to produce an increase in OD$_{340}$ over the 10 min incubation period in wells containing 5% DMSO, but no test compound. Preliminary experiments established that the GK reaction was linear over this period of time, even in the presence of activators that produced a 8-fold increase in GK activity. The GK activity in control wells was compared with the activity in wells containing test GK activators. The compound concentrations that produced a 50% increase in GK activity (i.e. FA 1.5) were calculated. GK activators achieved FA 1.5 at ≦30 µM.

The above EXAMPLES 1-201 produced EC$_{50}$s ranging from 0.1 to 32.6 µM with max FAs from 1.6 to 8.7.

The following compounds did not achieve FA 1.5 at ≦30 µM and hence are not preferred compounds of the invention:

2-(4-Bromophenyl)-3-furan-2-yl-N-[1,3,4]thiadiazol-2-yl-acrylamide;

3-Furan-2-yl-2-(4-methoxyphenyl)-N-(4-trifluoromethyl-thiazol-2-yl)acrylamide;

N-(5-Bromothiazol-2-yl)-3-furan-2-yl-2-(3-methoxyphenyl)acrylamide;

N-(5-Chlorothiazol-2-yl)-3-furan-2-yl-2-(3-methoxyphenyl)acrylamide;

4-[2-(Tetrahydropyran-4-yl)-1-(thiazol-2-ylcarbamoyl) ethyl]benzoic acid;

N-Methyl-4-[2-(tetrahydropyran-4-yl)-1-(thiazol-2-ylcarbamoyl)ethyl]benzamide;

N,N-Dimethyl-4-[2-(tetrahydropyran-4-yl)-1-(thiazol-2-ylcarbamoyl)ethyl]benzamide;

2-(4-Aminophenyl)-N-(5-chlorothiazol-2-yl)-3-(tetrahydropyran-4-yl)-propionamide;

N-(5-Dimethylaminomethylthiazol-2-yl)-2-(4-methanesulfonylphenyl)-3-(tetrahydropyran-4-yl)propionamide;

N-(5-Chlorobenzooxazol-2-yl)-2-(4-methanesulfonylphenyl)-3-(tetrahydropyran-4-yl)propionamide;

2-(4-Methanesulfonylphenyl)-N-(1-methyl-1H-benzoimidazol-2-yl)-3-(tetrahydropyran-4-yl)propionamide;

N-(1H-Benzoimidazol-2-yl)-2-(4-methanesulfonylphenyl)-3-(tetrahydropyran-4-yl)-propionamide;

N-Isoquinolin-1-yl-2-(4-methanesulfonylphenyl)-3-(tetrahydropyran-4-yl)-propionamide;

N-Isoquinolin-3-yl-2-(4-methanesulfonylphenyl)-3-(tetrahydropyran-4-yl)-propionamide;

3-[2-(Tetrahydropyran-4-yl)-1-(thiazol-2-ylcarbamoyl) ethyl]benzoic acid;

3-[2-(Tetrahydropyran-4-yl)-1-(thiazol-2-ylcarbamoyl) ethyl]-N-thiazol-2-yl-benzamide;

3-[2-(Tetrahydropyran-4-yl)-1-(thiazol-2-ylcarbamoyl) ethyl]benzoic acid methyl ester;

2-(4-Mercaptophenyl)-3-(tetrahydro-pyran-4-yl)-N-thiazol-2-ylpropionamide;

2-(4-Aminophenyl)-3-(tetrahydro-pyran-4-yl)-N-thiazol-2-yl-propionamide;

2-[2-(4-Methanesulfonylphenyl)-3-(tetrahydropyran-4-yl) propionylamino]-thiazole-4-carboxylic acid;

4-[2-(Tetrahydropyran-4-yl)-1-(thiazol-2-ylcarbamoyl) ethyl]benzamide;

2-(3-Cyclopropanesulfonylaminophenyl)-3-(tetrahydropyran-4-yl)-N-thiazol-2-yl-propionamide;

2-[2-(4-Methanesulfonylphenyl)-3-(tetrahydropyran-4-yl) propionylamino]-thiazole-4-carboxylic acid ethyl ester;
2-[2-(4-Methanesulfonylphenyl)-3-(tetrahydropyran-4-yl)- propionylamino]-thiazole-5-carboxylic acid ethyl ester;
2-(3-Methanesulfonylaminophenyl)-3-(tetrahydropyran-4-yl)-N-thiazol-2-yl-propionamide;
2-(4-Methanesulfonylphenyl)-3-(tetrahydropyran-4-yl)-N-(5-trifluoromethylthiazol-2-yl)-propionamide;
2-(4-Cyanophenyl)-3-(tetrahydropyran-4-yl)-N-thiazol-2-yl-propionamide;
2-(4-Dimethylaminomethylphenyl)-3-(tetrahydropyran-4-yl)-N-thiazol-2-yl-acrylamide;
2-(4-Methylaminomethylphenyl)-3-(tetrahydropyran-4-yl)-N-thiazol-2-yl-acrylamide;
2-[2-(4-Carboxyphenyl)-3-(tetrahydropyran-4-yl)acryloylamino]-thiazole-5-carboxylic acid;
N-[5-(4-Ethylpiperazine-1-carbonyl)thiazol-2-yl]-2-phenyl-3-(tetrahydropyran-4-yl)acrylamide;
N-[5-(4-Methylpiperazine-1-carbonyl)thiazol-2-yl]-2-phenyl-3-(tetrahydropyran-4-yl)acrylamide;
2-[2-Phenyl-3-(tetrahydro-pyran-4-yl)acryloylamino]thiazole-5-carboxylic acid (2-dimethylaminoethyl)amide;
2-(4-Methanesulfonylphenyl)-4-(tetrahydropyran-4-yl)-N-thiazol-2-yl-butyramide;
2-(4-Methanesulfonylphenyl)-4-(tetrahydropyran-4-yl)-but-2-enoic acid thiazol-2-ylamide;
2-(4-Acetylaminophenyl)-N-(5-chlorothiazol-2-yl)-3-(tetrahydropyran-4-yl)acrylamide;
N-(5-Chlorothiazol-2-yl)-2-(4-methanesulfonylphenyl)-3-piperidin-4-yl-acrylamide;
2-(4-Methanesulfonylphenyl)-3-piperidin-4-yl-N-thiazol-2-yl-acrylamide;
2-(4-Aminophenyl)-3-(tetrahydro-pyran-4-yl)-N-thiazol-2-yl-acrylamide;
2-(4-Aminophenyl)-N-(5-chloro-thiazol-2-yl)-3-(tetrahydro-pyran-4-yl)acrylamide;
2-(4-Methanesulfonylphenyl)-3-piperidin-1-yl-N-thiazol-2-yl-propionamide;
2-(4-Methanesulfonylphenyl)-3-(3-methylthiophen-2-yl)-N-thiazol-2-yl-acrylamide;
2-(4-Methanesulfonylphenyl)-3-pyridin-3-yl-N-thiazol-2-yl-acrylamide;
2-(3-Bromophenyl)-N-(5-chlorothiazol-2-yl)-3-thiophen-2-yl-acrylamide;
2-(3-Bromophenyl)-N-thiazol-2-yl-3-thiophen-2-yl-acrylamide;
N-(4,5-Dimethylthiazol-2-yl)-2-phenyl-3-thiophen-2-yl-acrylamide;
N-(5-Chlorothiazol-2-yl)-2-phenyl-3-thiophen-2-yl-acrylamide;
N-(5-Methylthiazol-2-yl)-2-phenyl-3-thiophen-2-yl-acrylamide;
2-(4-Bromophenyl)-N-pyrazin-2-yl-3-thiophen-2-yl-acrylamide;
3-Furan-2-yl-2-(3-methoxyphenyl)-N-thiazol-2-yl-acrylamide;
2-(4-Bromophenyl)-N-(5-bromopyridin-2-yl)-3-furan-2-yl-acrylamide;
N-(5-Bromothiazol-2-yl)-2-(4-cyanophenyl)-3-phenyl-acrylamide;
2-(4-Cyanophenyl)-3-phenyl-N-[1,3,4]thiadiazol-2-yl-acrylamide;
2-(4-Cyanophenyl)-3-furan-2-yl-N-[1,3,4]thiadiazol-2-yl-acrylamide;
2-(4-Cyanophenyl)-3-phenyl-N-thiazol-2-yl-acrylamide;
3-Furan-2-yl-2-(3-methoxyphenyl)-N-pyridin-2-yl-acrylamide;
2-(4-Bromophenyl)-N-(4,5-dimethylthiazol-2-yl)-3-thiophen-2-yl-acrylamide;
2-(4-Bromophenyl)-N-pyridin-2-yl-3-thiophen-2-yl-acrylamide;
2-(4-Bromophenyl)-N-pyrimidin-4-yl-3-thiophen-2-yl-acrylamide;
2-(4-Bromophenyl)-3-thiophen-2-yl-N-(4-trifluoromethyl-thiazol-2-yl)acrylamide;
N-(5-Bromopyridin-2-yl)-3-furan-2-yl-2-(4-methoxyphenyl)acrylamide;
3-Furan-2-yl-2-(4-methoxyphenyl)-N-pyrimidin-4-yl-acrylamide;
N-(5-Bromothiazol-2-yl)-3-furan-2-yl-2-(4-methoxyphenyl)acrylamide;
N-(5-Chlorothiazol-2-yl)-3-furan-2-yl-2-(4-methoxyphenyl)acrylamide;
N-Benzothiazol-2-yl-3-furan-2-yl-2-(4-methoxyphenyl) acrylamide;
N-Benzothiazol-2-yl-2-(4-bromophenyl)-3-thiophen-2-yl-acrylamide;
3-Furan-2-yl-2-(4-methoxphenyl)-N-[1,3,4]thiadiazol-2-yl-acrylamide;
2-(4-Bromophenyl)-N-(5-bromopyridin-2-yl)-3-thiophen-2-yl-acrylamide; and
N-(4,5-Dimethylthiazol-2-yl)-3-furan-2-yl-2-(4-methoxyphenyl)acrylamide.

In Vivo GK Activity

Following an 18 h fasting period, C57BL/6J mice were dosed orally via gavage with GK activator at 50 mg/kg body weight. Blood Glc determinations were made 5 times during the 6 h post-dose study period.

Mice (n=5) were weighed and fasted for 18 h before oral treatment. GK activators were dissolved in the Gelucire vehicle reported in WO 00/58293 (EtOH-Gelucire44/14: PEG400q.s. 4:66:30 v/v/v) at a concentration of 13.3 mg/mL. Mice were dosed orally with 7.5 mL formulation per kg of body weight to equal a 50 mg/kg dose. Immediately prior to dosing, a pre-dose (time zero) blood Glc reading was acquired by snipping off a small portion of the animals' tails (<1 mm) and collecting 15 µL blood for analysis. After GK activator treatment, further blood Glc readings were taken at 1, 2, 4, and 6 h post-dose from the same tail wound. Results were interpreted by comparing the mean blood Glc values of 5 vehicle treated mice with the 5 GK activator treated mice over the 6 h study duration. Compounds are considered active when they exhibit a statistically significant decrease in blood Glc compared to vehicle for 2 consecutive assay time points.

Several of the GK activators exemplified above showed strong GK activator effects in vivo when administered orally following the abovementioned protocol.

What is claimed is:

1. A compound of Formula (I):

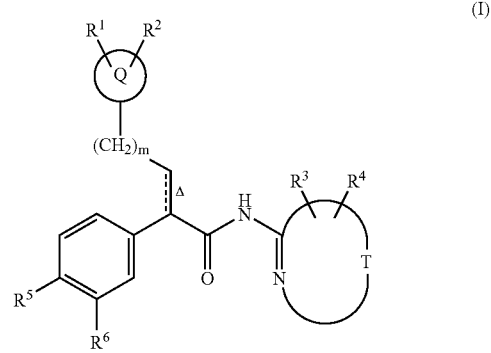

or a pharmaceutically acceptable salt thereof, wherein:

Q is an aryl, a 5- or 6-membered heteroaryl, or a 4-8-membered heterocyclic ring;

T together with the —N═C— to which it is attached forms a heteroaryl ring, or a heterocyclic ring where the N═C bond is the only site of unsaturation;

$R^1$ and $R^2$ each independently are hydrogen, hydroxy, halogen, cyano, nitro, vinyl, ethynyl, methoxy, $OCF_nH_{3-n}$, —N($C_{0-4}$alkyl)($C_{0-4}$alkyl)-, CHO, or $C_{1-2}$alkyl optionally substituted with 1-5 independent halogen, hydroxy, cyano, methoxy, —N($C_{0-2}$alkyl)($C_{0-2}$alkyl), $SOCH_3$, or $SO_2CH_3$ substituents; or $R^1$ and $R^2$ together form a carbocyclic or heterocyclic ring; or $R^1$ and $R^2$ may be taken together to represent an oxygen atom attached to the ring via a double bond;

$R^1$ and $R^4$ each independently are hydrogen, halogen, $OCF_nH_{3-n}$, methoxy, $CO_2R^{77}$, cyano, nitro, CHO, $CONR^{99}R^{100}$, $CON(OCH_3)CH_3$, or $C_{1-2}$alkyl, heteroaryl, or $C_{3-7}$cycloalkyl optionally substituted with 1-5 independent halogen, hydroxy, cyano, methoxy, —$NHCO_2CH_3$, or —N($C_{0-2}$alkyl)($C_{0-2}$alkyl) substituents; or $R_3$ and $R_4$ together form a 5-8-membered aromatic, heteroaromatic, carbocyclic, or heterocyclic ring;

$R^5$ is $SO_2C_{3-4}$cycloalkyl;

$R_6$ is hydrogen, hydroxy, halogen, cyano, nitro, $CO_2R^7$, CHO, $COR^8$, $C(OH)R^7R^8$, $C(═NOR^7)R^8$, $CONR^9R^{10}$, $SR^7$, $SOR^8$, $SO_2R^8$, $SO_2NR^9R^{10}$, $CH_2NR^9R^{10}$, $NR^9R^{10}$, N($C_{0-4}$alkyl)$SO_2R^8$, $NHCOR^7$, or $C_{1-4}$alkyl group, $C_{2-4}$alkenyl group, $C_{2-4}$alkynyl group, $C_{1-4}$alkoxy group, aryl group, or heteroaryl group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $CF_nH_{3-n}$, aryl, heteroaryl, —$COC_{1-2}$alkyl, —CON($C_{0-2}$alkyl)($C_{0-2}$alkyl), $SCH_3$, $SOCH_3$, $SO_2CH_3$, or —$SO_2N(C_{0-2}$alkyl)($C_{0-2}$alkyl) substituents;

$R^7$ and $R^{77}$ each independently are hydrogen, or $C_{1-4}$alkyl group, $C_{2-4}$alkenyl group, $C_{2-4}$alkynyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $C_{3-7}$cycloalkyl, 4-7-membered heterocyclic ring, $CF_nH_{3-n}$, aryl, heteroaryl, $CO_2H$, —$COC_{1-2}$alkyl, —CON($C_{0-2}$alkyl)($C_{0-2}$alkyl), $SOCH_3$, $SO_2CH_3$, or —$SO_2N(C_{0-2}$alkyl-)($C_{0-2}$alkyl) substituents;

$R^8$ is $C_{1-4}$alkyl group, $C_{2-4}$alkenyl group, $C_{2-4}$alkynyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $C_{3-7}$cycloalkyl, 4-7-membered heterocyclic ring, $CF_nH_{3-n}$, aryl, heteroaryl, $CO_2H$, $COC_{1-2}$alkyl, —CON($C_{0-2}$alkyl)($C_{0-2}$alkyl), $SOCH_3$, $SO_2CH_3$, or —$SO_2N(C_{0-2}$alkyl)($C_{0-2}$alkyl) substituents;

$R^9$, $R^{10}$, $R^{99}$, and $R^{100}$ each independently are hydrogen, or $C_{1-4}$alkyl group, $C_{3-7}$cycloalkyl group, aryl group, heteroaryl group, or 4-7-membered heterocyclic group, wherein any group optionally is substituted with 1-6 independent halogen, cyano, nitro, hydroxy, $C_{1-2}$alkoxy, —N($C_{0-2}$alkyl)($C_{0-2}$alkyl), $C_{1-2}$alkyl, $C_{3-7}$cycloalkyl, 4-7-membered heterocyclic ring, $CF_nH_{3-n}$, aryl, heteroaryl, $COC_{1-2}$alkyl, —CON($C_{0-2}$alkyl)($C_{0-2}$alkyl)-, $SOCH_3$, $SO_2CH_3$, or —$SO_2N(C_{0-2}$alkyl)($C_{0-2}$alkyl) substituents; or $R^9$ and $R^{10}$ or $R^{99}$ and $R^{100}$ together form a 6-8-membered heterobicyclic ring system or a 4-8-membered heterocyclic ring which optionally is substituted with 1-2 independent $C_{1-2}$alkyl, $CH_2OCH_3$, $COC_{0-2}$alkyl, hydroxy, or $SO_2CH_3$ substituents;

n is 1, 2 or 3;

m is 0 or 1; and the dotted line together with the solid line forms an optional double bond, and A indicates that the double bond has the (L)-configuration;

provided that when Q is 4-tetrahydropyranyl and the dotted line together with the solid line forms a single bond, then T together with the —N═C— to which it is attached is not 2-pyrazinyl or 2-thiazolyl wherein $R^3$ and $R^4$ are each independently hydrogen or fluoro.

2. A compound according to claim 1, or a pharmaceutically acceptable salt thereof, wherein the dotted line together with the solid line forms a double bond.

3. A compound according to claim 1, or a pharmaceutically acceptable salt thereof, wherein the dotted line together with the solid line forms a single bond.

4. A compound according to claim 3, or a pharmaceutically acceptable salt thereof, wherein the dotted line together with the solid line forms a single bond, and the absolute configuration at the asymmetric centre α to the amide carbonyl carbon is (R).

5. A compound according to claim 1, wherein m is 0.

6. The compound according to claim 1, or a pharmaceutically acceptable salt thereof, wherein Q is thienyl, furyl, thiazolyl, pyridyl, tetrahydropyranyl, piperidinyl, tetrahydrothiopyranyl, 1-oxo-tetrahydrothiopyranyl or 1,1-dioxo-tetrahydrothiopyranyl.

7. A compound according to claim 6, or a pharmaceutically acceptable salt thereof, wherein Q is 4-tetrahydropyranyl.

8. The compound according to claim 1, or a pharmaceutically acceptable salt thereof, wherein the group of formula

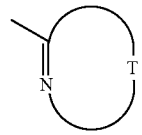

is thiazolyl, thiadiazolyl, oxazolyl, isoxazolyl, pyrimidinyl, pyrazinyl, or pyridyl.

9. A compound according to claim 8, or a pharmaceutically acceptable salt thereof, wherein the group of formula

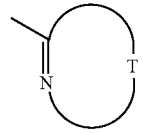

is 2-pyrazinyl or 2-thiazolyl.

10. A compound according to claim 9, or a pharmaceutically acceptable salt thereof, wherein the group of formula

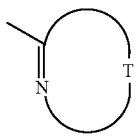

is 2-thiazolyl, $R^3$ is 5-fluoro and $R^4$ is hydrogen.

11. A compound according to claim 1, or a pharmaceutically acceptable salt thereof, wherein $R^3$ and $R^4$ are independently selected from hydrogen, halogen, and methyl.

12. A compound according to claim 1, or a pharmaceutically acceptable salt thereof, wherein $R^6$ is hydrogen.

13. A compound according to claim 1 selected from:
2-(4-Cyclopropanesulfonylphenyl)-N-(3-methyl-[1,2,4]thiadiazol-5-yl)-3-(tetrahydropyran-4-yl)propionamide;
2-(4-Cyclopropanesulfonylphenyl)-3-(tetrahydropyran-4-yl)-N-[1,2,4]thiadiazol-5-ylpropionamide;
(E)-2-(4-Cyclopropanesulfonylphenyl)-3-(tetrahydropyran-4-yl)-N-thiazol-2-ylacrylamide;
2-(4-Cyclopropanesulfonylphenyl)-N-(5-formylthiazol-2-yl)-3-(tetrahydropyran-4-yl)propionamide;
(2R)-2-(4-Cyclopropanesulfonylphenyl)-3-(tetrahydropyran-4-yl)-N-[1,2,4]thiadiazol-5-ylpropionamide;
(2R)-2-(4-Cyclopropanesulfonylphenyl)-N-(5-fluoropyridin-2-yl)-3-(tetrahydropyran-4-yl)propionamide;
(2R)-2-(4-Cyclopropanesulfonylphenyl)-N-(3-methyl-[1,2,4]thiadiazol-5-yl)-3-(tetrahydropyran-4-yl)propionamide;
(2R)-2-(4-Cyclobutanesulfonylphenyl)-N-pyrimidin-4-yl-3-(tetrahydropyran-4-yl)propionamide;
(2R)-2-(4-Cyclobutanesulfonylphenyl)-N-isoxazol-3-yl-3-(tetrahydropyran-4-yl)propionamide;
(2R)-2-(4-Cyclobutanesulfonylphenyl)-N-(1-methyl-1H-pyrazol-3-yl)-3-(tetrahydropyran-4-yl)propionamide;
(E)-2-(4-Cyclopropanesulfonylphenyl)-N-(5-fluoropyridin-2-yl)-3-(tetrahydropyran-4-yl)acrylamide;
(E)-2-(4-Cyclopropanesulfonylphenyl)-N-(5-fluorothiazol-2-yl)-3-(tetrahydropyran-4-yl)acrylamide and
N-(5-Cyanothiazol-2-yl)-2-(4-cyclopropanesulfonylphenyl)-3-(tetrahydropyran-4-yl)propionamide;
or a pharmaceutically acceptable salt thereof.

14. A pharmaceutical composition comprising a compound according to claim 1, or a pharmaceutically acceptable salt thereof, and a pharmaceutically acceptable carrier.

15. A method of therapeutic treatment of a condition wherein activation of GK is desirable comprising a step of administering an effective amount of a compound according to claim 1, or a pharmaceutically acceptable salt thereof.

16. A method according to claim 15 wherein the condition where activation of GK is desirable is hyperglycemia or diabetes.

17. The method according to claim 16 wherein the compound according to claim 1 is administered in combination with one or more other anti-hyperglycemic agents or anti-diabetic agents.

18. A process for the preparation of a compound of Formula (I)

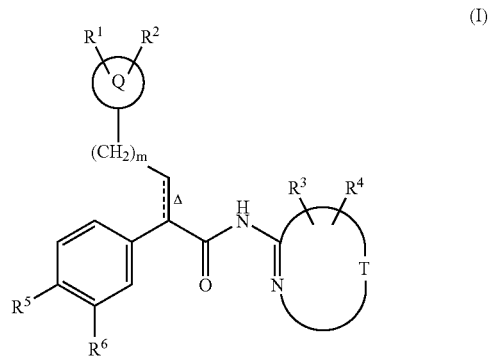

said process comprising a step of the condensation of a compound of a formula below:

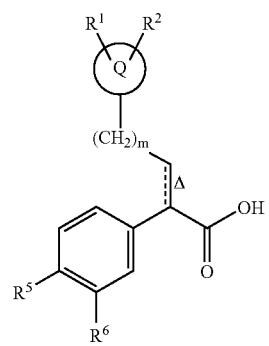

with a compound of Formula (V):

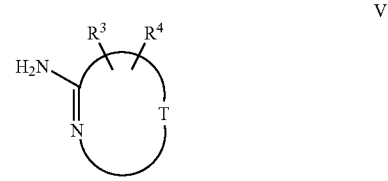

wherein Q, T, $R^1$ to $R^6$, m and Δ are as defined in claim 1; and wherein the dotted line together with the solid line forms an optional double bond, and Δ indicates that the double bond has the (E)-configuration;

provided that when Q is 4-tetrahydropyranyl and the dotted line together with the solid line forms a single bond, then T together with the —N=C— to which it is attached is not 2-pyrazinyl or 2-thiazolyl wherein $R^3$ and $R^4$ are each independently hydrogen or fluoro.

19. A compound according to claim 1, or a pharmaceutically acceptable salt thereof, wherein $R^1$ and $R^2$ are hydrogen.

20. A compound according to claim 1, or a pharmaceutically acceptable salt thereof, wherein $R^6$ is hydrogen, chloro, fluoro, or trifluoromethyl.

21. A compound according to claim 8, or a pharmaceutically acceptable salt thereof, wherein the group of formula

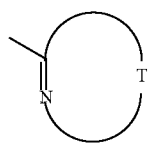

is 2-thiazolyl, 5-[1,2,4]thiadiazolyl, 2-[1,3,4]thiadiazolyl, 4-pyrimidinyl, 2-pyrazinyl, 3-isoxazolyl, or 2-pyridyl.

22. A compound according to claim 8, or a pharmaceutically acceptable salt thereof, wherein the group of formula

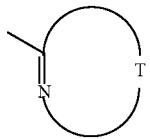

is 2-thiazolyl, 5-[1,2,4]thiadiazolyl, 4-pyrimidinyl, 2-pyrazinyl, or 2-pyridyl.

* * * * *